United States Patent
Wang et al.

(10) Patent No.: US 11,236,094 B2
(45) Date of Patent: Feb. 1, 2022

(54) SUBSTITUTED PYRROLO[2,1-F][1,2,4]TRIAZINES AS FGFR INHIBITORS

(71) Applicant: CSPC ZHONGQI PHARMACEUTICAL TECHNOLOGY (SHIJIAZHUANG) CO., LTD., Hebei (CN)

(72) Inventors: Yikai Wang, Shanghai (CN); Yang Zhang, Shanghai (CN); Zhengxia Chen, Shanghai (CN); Linlin Chen, Shanghai (CN); Tao Feng, Shanghai (CN); Rongxin Huang, Shanghai (CN); Qiu Li, Shanghai (CN); Deyao Li, Shanghai (CN); Jikui Sun, Shanghai (CN); Yangyang Xu, Shanghai (CN); Jie Li, Shanghai (CN); Jian Li, Shanghai (CN); Shuhui Chen, Shanghai (CN)

(73) Assignee: CSPC ZHONGQI PHARMACEUTICALL TECHNOLOGY (SHIJIAZHUANG) CO., LTD., Hebei (CN)

(*) Notice: Subject to any disclaimer, the term of this patent is extended or adjusted under 35 U.S.C. 154(b) by 32 days.

(21) Appl. No.: 16/639,442

(22) PCT Filed: Aug. 15, 2018

(86) PCT No.: PCT/CN2018/100638
§ 371 (c)(1),
(2) Date: Feb. 14, 2020

(87) PCT Pub. No.: WO2019/034076
PCT Pub. Date: Feb. 21, 2019

(65) Prior Publication Data
US 2020/0207773 A1 Jul. 2, 2020

(30) Foreign Application Priority Data

Aug. 15, 2017 (CN) .......................... 201710698086.3

(51) Int. Cl.
*A61K 31/53* (2006.01)
*C07D 487/04* (2006.01)

(52) U.S. Cl.
CPC ................... *C07D 487/04* (2013.01)

(58) Field of Classification Search
CPC ..................... A61K 31/53; C07D 487/04

USPC ........................... 514/243; 544/183
See application file for complete search history.

(56) References Cited

U.S. PATENT DOCUMENTS

2013/0158000 A1 6/2013 Brohm et al.

FOREIGN PATENT DOCUMENTS

| CA | 3072979 A1 * | 2/2019 | ............ A61P 35/00 |
|----|---|---|---|
| WO | 2013087578 | 6/2013 | |
| WO | 2013087647 | 6/2013 | |
| WO | 2013124316 | 8/2013 | |
| WO | 2015008844 | 1/2015 | |

OTHER PUBLICATIONS

Jordan, V. C. Nature Reviews: Drug Discovery, 2, 2003, 205.*
Hackam, et al. JAMA, 296(14), 2006, 1731-1732.*
Collin et al., Discovery of Rogaratinib (BAY 1163877): a pan-FGFR Inhibitor, ChemMedChem, vol. 13, No. 5, Mar. 6, 2018, pp. 1-10.
International Application No. PCT/CN2018/100638, International Preliminary Report on Patentability, dated Feb. 27, 2020, 11 pages (4 pages of Original Document and 7 pages of English Translation).
International Application No. PCT/CN2018/100638, International Search Report and Written Opinion, dated Nov. 22, 2018, 16 pages (9 pages of Original Document and 7 pages of English Translation).

* cited by examiner

*Primary Examiner* — Douglas M Willis
(74) *Attorney, Agent, or Firm* — Kilpatrick Townsend & Stockton LLP

(57) ABSTRACT

Provided is a FGFR inhibitor, designating a compound represented by formula (I) or a pharmaceutically acceptable salt thereof. Also provided is the application of a drug for treating solid tumors, such as FGFR related diseases.

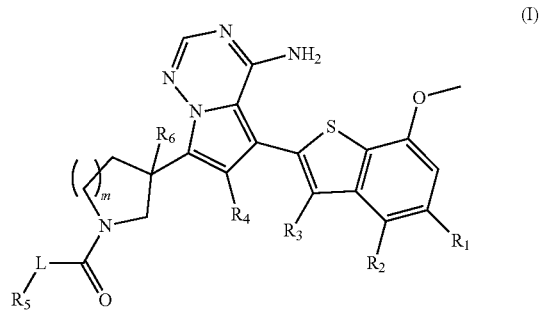

20 Claims, No Drawings

SUBSTITUTED PYRROLO[2,1-F][1,2,4]TRIAZINES AS FGFR INHIBITORS

CROSS-REFERENCE TO RELATED APPLICATIONS

This application is a national phase entry under 35 USC § 371 of International Application PCT/CN2018/100638, filed Aug. 15, 2018, and entitled "FGFR INHIBITOR AND MEDICAL APPLICATION THEREOF", which claims priority to and benefits of Chinese Patent Application No. 201710698086.3 filed on Aug. 15, 2017, the disclosures of which are hereby incorporated in their entireties by this reference.

TECHNICAL FIELD

The present invention relates to an FGFR inhibitor, and its use in the manufacture of a medicament for treating an FGFR-related disease. In particular, the present invention relates to a compound represented by formula (I) and a pharmaceutically acceptable salt thereof.

BACKGROUND

Fibroblast growth factor receptor (FGFR) is a receptor for the signal transduction of the fibroblast growth factor (FGF). Its family consists of four members (FGFR1, FGFR2, FGFR3, FGFR4), and is a glycoprotein composed of an extracellular immunoglobulin (Ig) like structural domain, a hydrophobic cross-membrane region and an intracellular part including a tyrosine kinase region. Fibroblast growth factor (FGF) plays an important role in many physiological regulation processes such as cell proliferation, cell differentiation, cell migration, and angiogenesis through these receptors (FGFR). There is much evidence that abnormalities in FGF signaling pathways (high expression, gene amplification, gene mutation, chromosomal recombination and the like) are directly related to many pathological processes such as tumor cell proliferation, migration, invasion, and angiogenesis. Therefore, FGFR has become an important therapeutic target, attracting a wide range of research and development interests.

Patent Application WO2015008844 reports a series of compounds having inhibitory activity on FGFR, including reference compounds 1 and 2. Patent Applications WO2013124316, WO2013087647, and US20130158000 report a series of compounds having inhibitory activity on FGFR, including the benzothiophene structure used in the present invention, and reference compound 3.

SUMMARY OF THE INVENTION

The present invention provides a compound represented by formula (I) or a pharmaceutically acceptable salt thereof,

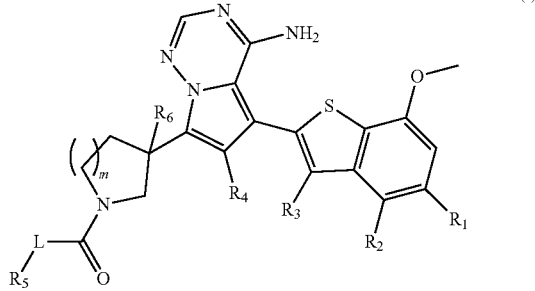

wherein,
m is 1 or 2;
L is selected from a single bond, $C_{2-4}$ alkeneyl, and $C_{2-4}$ alkynyl;
$R_1$ is selected from H, halogen, OH and $NH_2$, or selected from $C_{1-3}$ alkyl and $C_{1-3}$ heteroalkyl, which are optionally substituted with 1, 2 or 3 R groups;
$R_2$ is selected from H, F, Cl, Br, I, OH and $NH_2$;
$R_3$ is selected from H, halogen, OH, $NH_2$ and CN, or selected from $C_{1-3}$alkyl and $C_{1-3}$heteroalkyl, which are optionally substituted with 1, 2 or 3 R groups;
$R_4$ is selected from H, halogen, OH, $NH_2$ and CN, or selected from $C_{1-3}$alkyl and $C_{1-3}$heteroalkyl, which are optionally substituted with 1, 2 or 3 R groups;
$R_5$ is H or selected from $C_{1-3}$ alkyl, $C_{1-3}$heteroalkyl, $C_{3-6}$ cycloalkyl and 4-6 membered heterocycloalkyl, which are optionally substituted with 1, 2 or 3 R groups;
$R_6$ is selected from H, halogen, OH and $NH_2$, or selected from $C_{1-3}$ alkyl optionally substituted with 1, 2 or 3 R groups;
R is selected from F, Cl, Br, I, OH, $NH_2$, CN, Me, $CF_3$, $N(CH_3)_2$ and

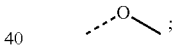

the heteroatom or the hetero group in the $C_{1-3}$ heteroalkyl and the 4-6 membered heterocycloalkyl are independently and separately selected from —NH—, N, —O—, and —S—;
in any of the above circumstances, the number of the heteroatom or the number of the hetero group is independently and separately selected from 1, 2 or 3.

In some embodiments of the present invention, the above-mentioned $R_1$ is selected from H, halogen, OH, and $NH_2$, or selected from $C_{1-3}$alkyl and $C_{1-3}$ alkoxyl, which are optionally substituted with 1, 2 or 3 R groups, and the R groups are defined as in the present invention.

In some embodiments of the present invention, the above-mentioned $R_1$ is selected from H, F, Cl, Br, I, OH, $NH_2$, Me and

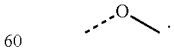

In some embodiments of the present invention, the above-mentioned $R_3$ is selected from H, halogen, OH, $NH_2$ and CN, or selected from $C_{1-3}$ alkyl, $C_{1-3}$ alkoxyl and $C_{1-3}$alkylamino, which are optionally substituted with 1, 2 or 3 R groups, and the R groups are defined as in the present invention.

In some embodiments of the present invention, the above-mentioned $R_3$ is selected from H, F, Cl, Br, I, OH, $NH_2$, CN, Me, $CF_3$,

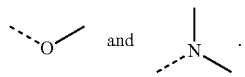

In some embodiments of the present invention, the above-mentioned $R_4$ is selected from H, halogen, OH, $NH_2$ and CN, or selected from $C_{1-3}$ alkyl, $C_{1-3}$ alkoxyl and $C_{1-3}$alkylamino, which are optionally substituted with 1, 2 or 3 R groups, and the R groups are defined as in the present invention.

In some embodiments of the present invention, the above-mentioned $R_4$ is selected from H, F, Cl, Br, I, OH, $NH_2$, CN, Me, $CF_3$,

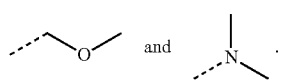

In some embodiments of the present invention, the above-mentioned $R_5$ is H or selected from $C_{1-3}$alkyl, $C_{1-3}$alkylamino, and morpholinyl, which are optionally substituted with 1, 2 or 3 R groups, and the R groups are defined as in the present invention.

In some embodiments of the present invention, the above-mentioned $R_5$ is selected from H, Me, Et,

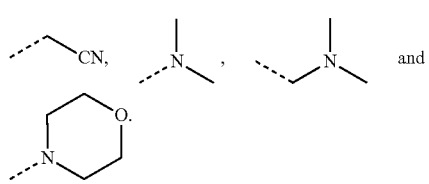

In some embodiments of the present invention, the above-mentioned $R_6$ is selected from H, F, Cl, Br, I, OH, $NH_2$ and Me.

In some embodiments of the present invention, the above-mentioned L is selected from a single bond,

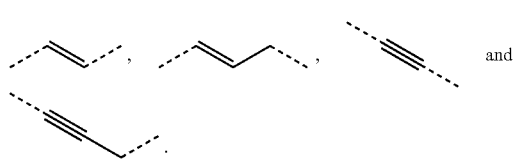

In some embodiments of the present invention, the above-mentioned structure unit

is selected from

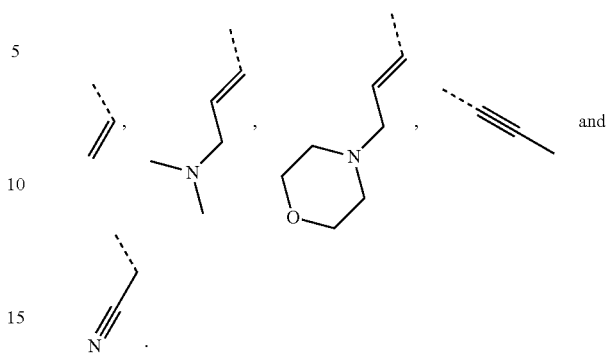

In some embodiments of the present invention, the above-mentioned structure unit

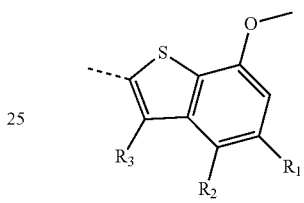

is selected from:

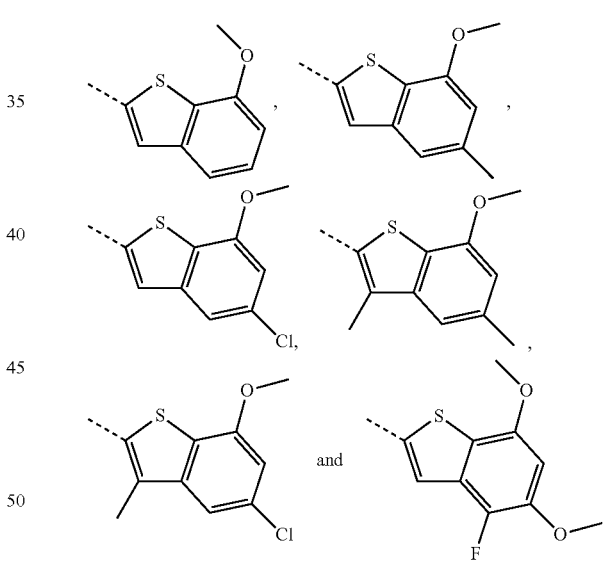

In some embodiments of the present invention, the above-mentioned $R_1$ is selected from H, halogen, OH, and $NH_2$, or selected from $C_{1-3}$alkyl and $C_{1-3}$ alkoxyl, which are optionally substituted with 1, 2 or 3 R groups, and other variables are defined as above.

In some embodiments of the present invention, the above-mentioned $R_1$ is selected from H, F, Cl, Br, I, OH, $NH_2$, Me and

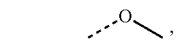

and other variables are defined as above.

In some embodiments of the present invention, the above-mentioned $R_3$ is selected from H, halogen, OH, $NH_2$ and CN, or selected from $C_{1-3}$ alkyl, $C_{1-3}$ alkoxyl and $C_{1-3}$ alkylamino, which are optionally substituted with 1, 2 or 3 R groups, and other variables are defined as above.

In some embodiments of the present invention, the above-mentioned $R_3$ is selected from H, F, Cl, Br, I, OH, $NH_2$, CN, Me, $CF_3$,

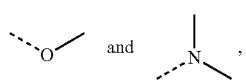

and other variables are defined as above.

In some embodiments of the present invention, the above-mentioned $R_4$ is selected from H, halogen, OH, $NH_2$ and CN, or selected from $C_{1-3}$ alkyl, $C_{1-3}$ alkoxyl and $C_{1-3}$ alkylamino, which are optionally substituted with 1, 2 or 3 R groups, and other variables are defined as above.

In some embodiments of the present invention, the above-mentioned $R_4$ is selected from H, F, Cl, Br, I, OH, $NH_2$, CN, Me, $CF_3$,

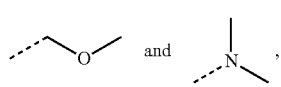

and other variables are defined as above.

In some embodiments of the present invention, the above-mentioned $R_5$ is H or selected from $C_{1-3}$ alkyl, $C_{1-3}$ alkylamino and morpholinyl, which are optionally substituted with 1, 2 or 3 R groups, and other variables are defined as above.

In some embodiments of the present invention, the above-mentioned $R_5$ is selected from H, Me, Et,

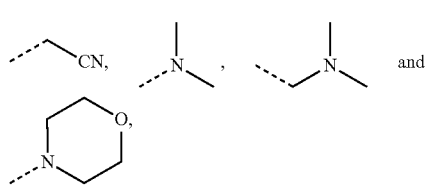

and other variables are defined as above.

In some embodiments of the present invention, the above-mentioned $R_6$ is selected from H, F, Cl, Br, I, OH, $NH_2$ and Me, and other variables are defined as above.

In some embodiments of the present invention, the above-mentioned L is selected from a single bond,

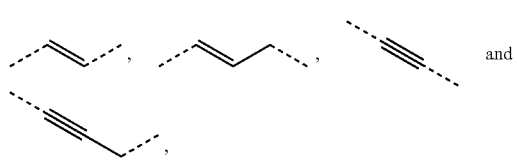

and other variables are defined as above.

In some embodiments of the present invention, the above-mentioned structure unit

is selected from

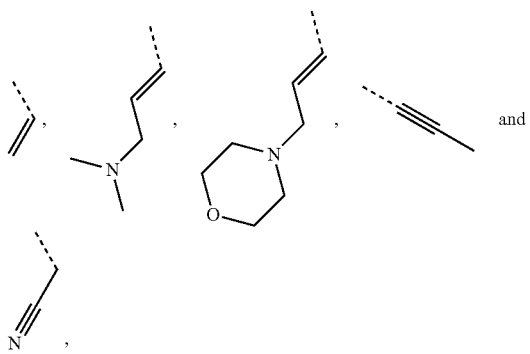

and other variables are defined as above.

In some embodiments of the present invention, the above-mentioned structure unit is

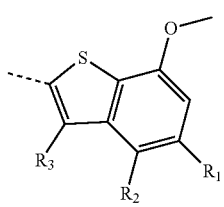

selected from

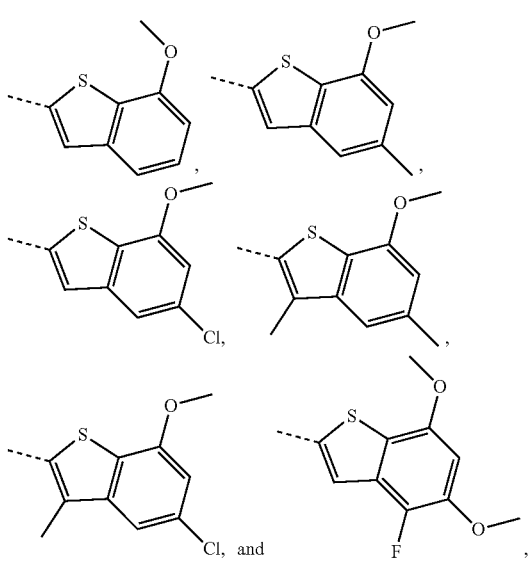

and other variables are defined as above.

In some embodiments of the present invention, it relates to the above-mentioned compound or a pharmaceutically acceptable salt thereof, which compound is selected from:

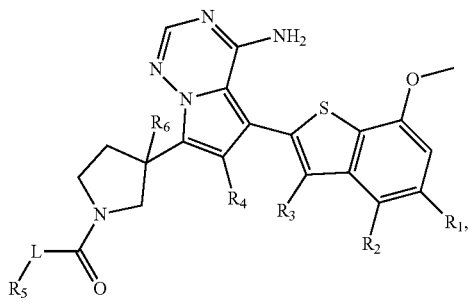

(I-1)

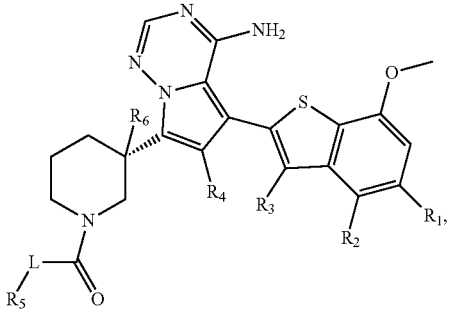

(I-2A)

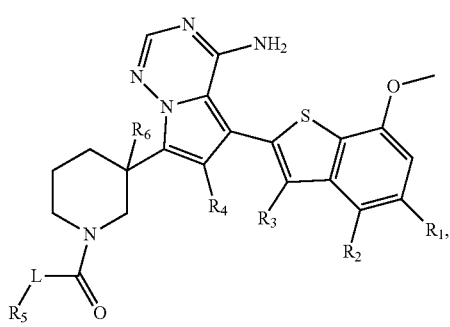

(I-2)

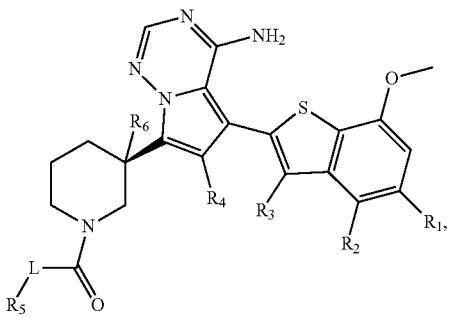

(I-2B)

wherein,

R₁, R₂, R₃, R₄, R₅, R₆ and L are defined as above.

In some embodiments of the present invention, it relates to the above-mentioned compound or a pharmaceutically acceptable salt thereof, which compound is selected from:

wherein,

R₁, R₂, R₃, R₄, R₅, R₆ and L are defined as above.

The present invention also comprises some embodiments, which are obtained from any combination of the above-mentioned variables.

The present invention further provides a compound represented by any of the following formulae or a pharmaceutically acceptable salt thereof:

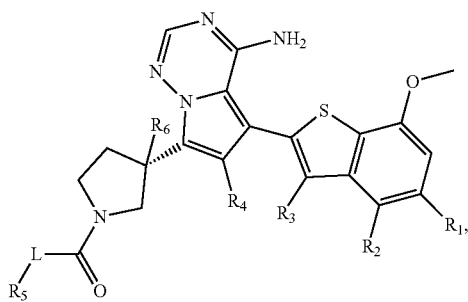

(I-1A)

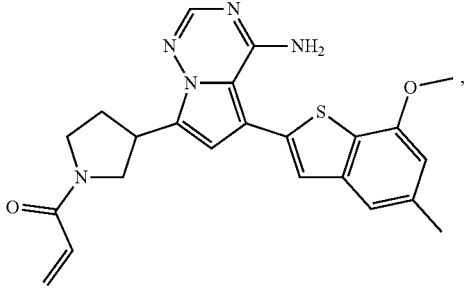

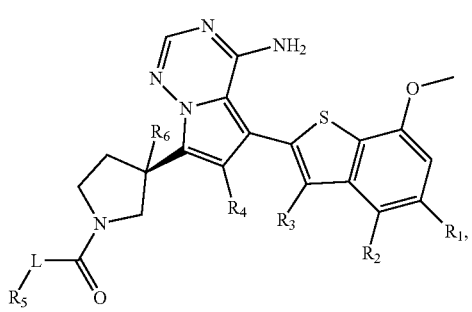

(I-1B)

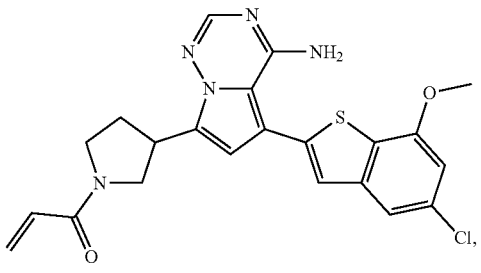

-continued
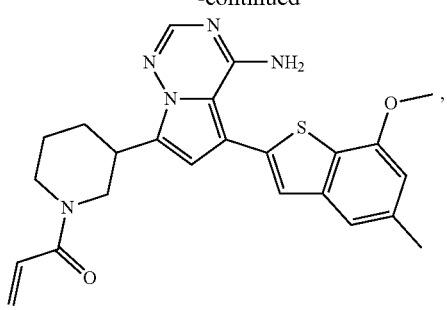
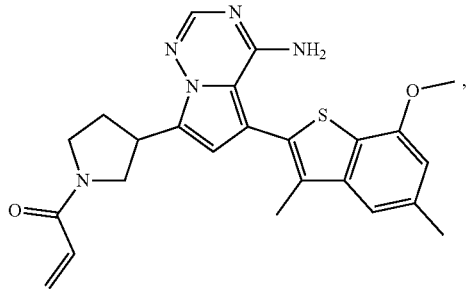
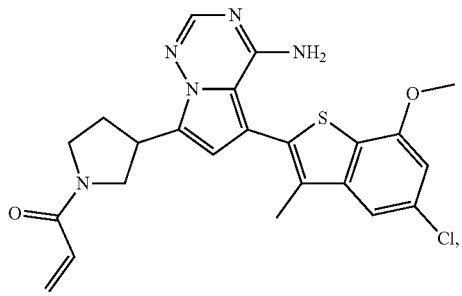
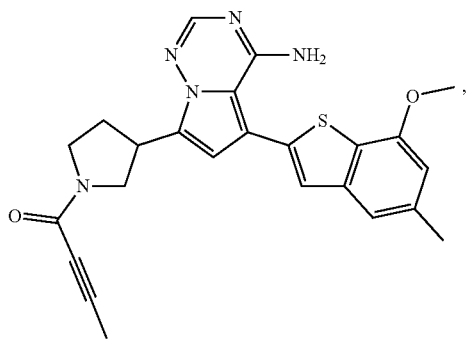
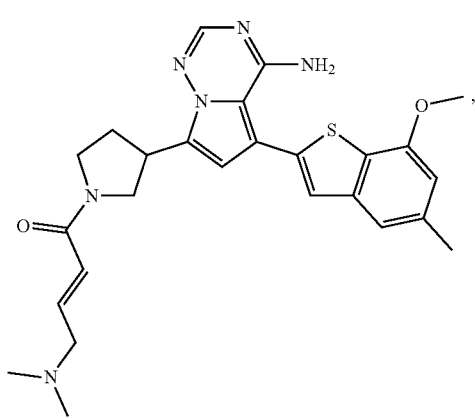
-continued
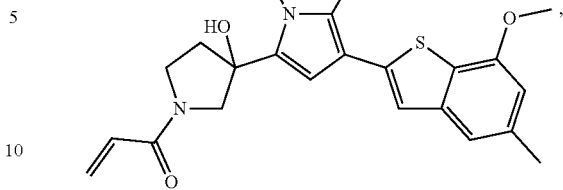
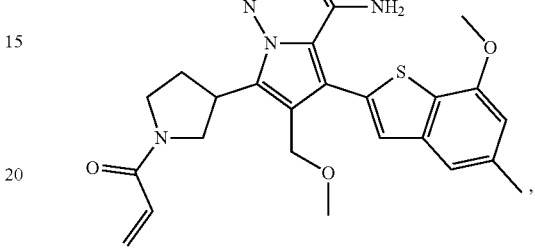
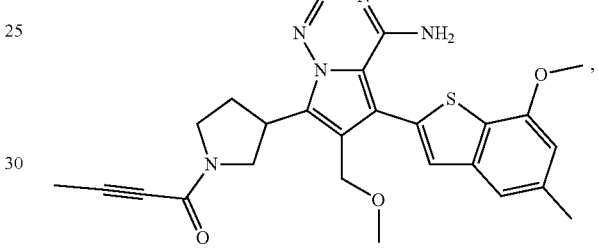
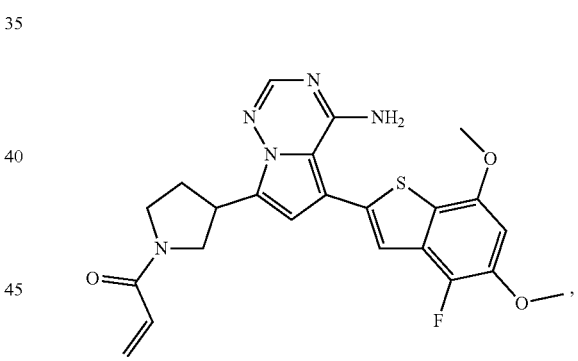
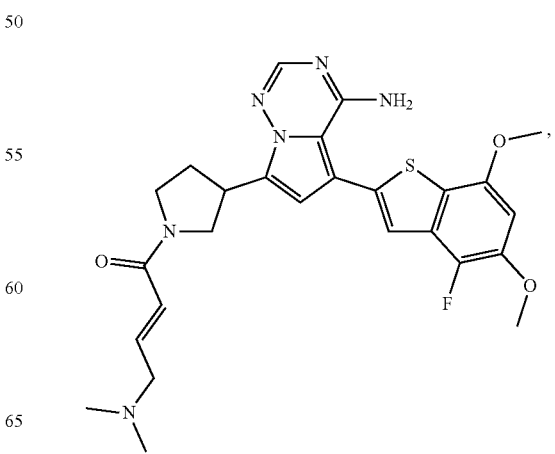

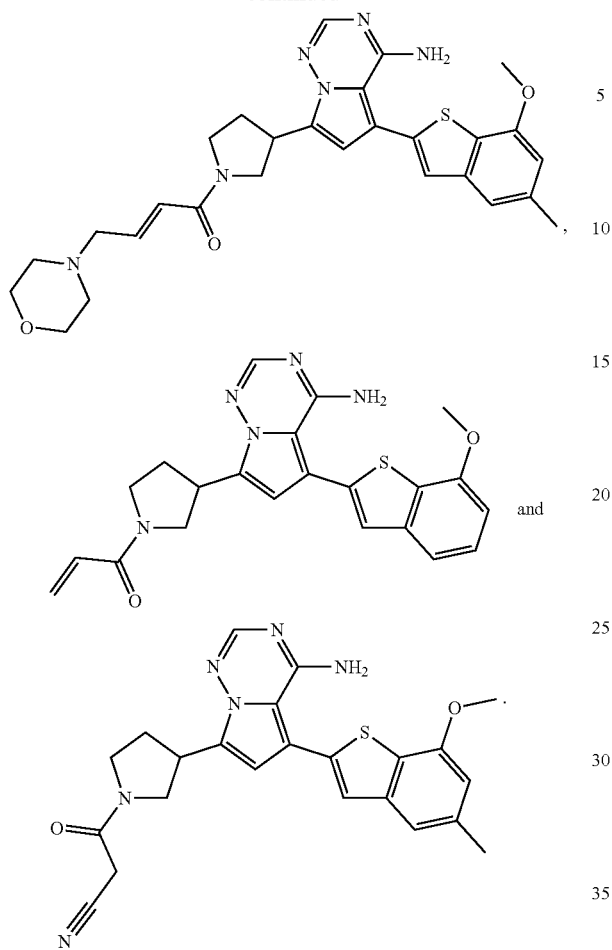
In some embodiments of the present invention, it relates to the above-mentioned compound or a pharmaceutically acceptable salt thereof, which compound is selected from:
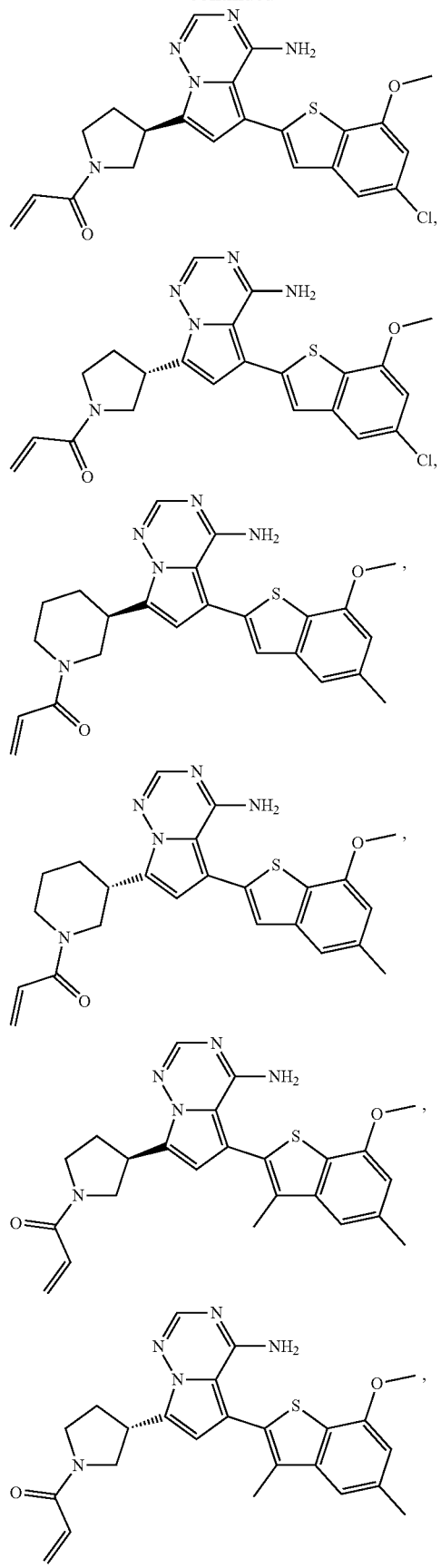

-continued
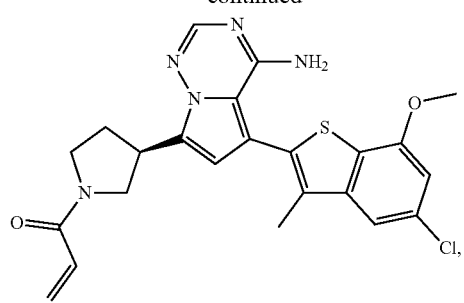
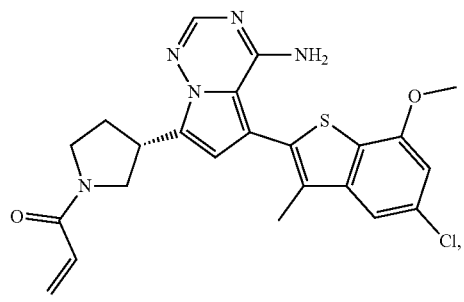
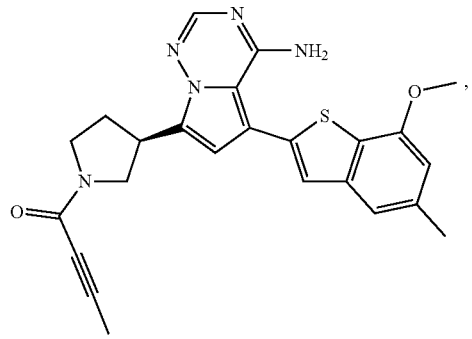
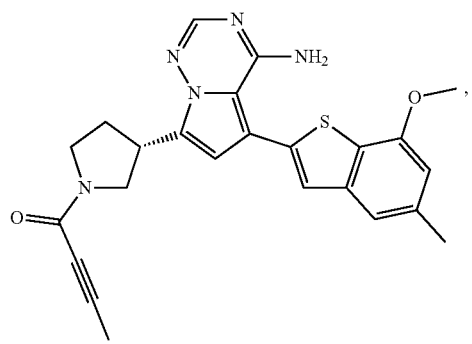
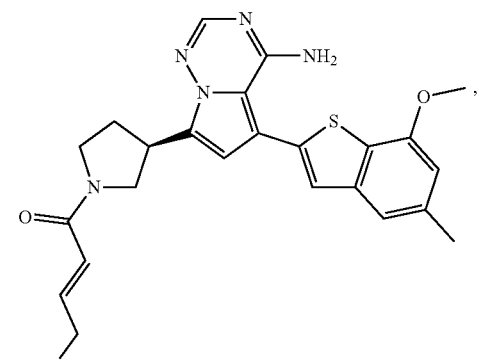
-continued
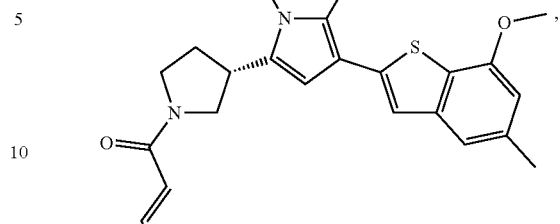
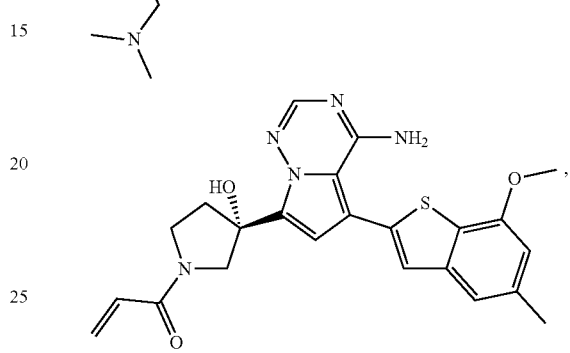
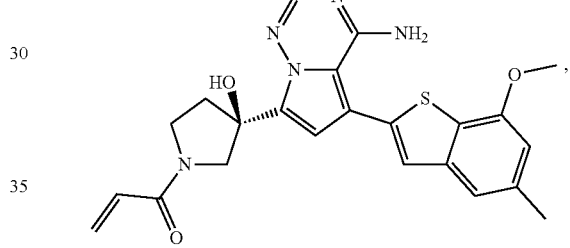
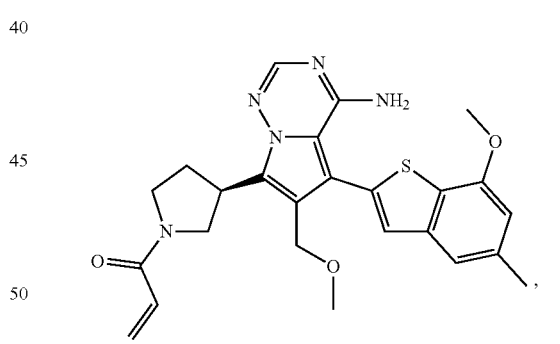
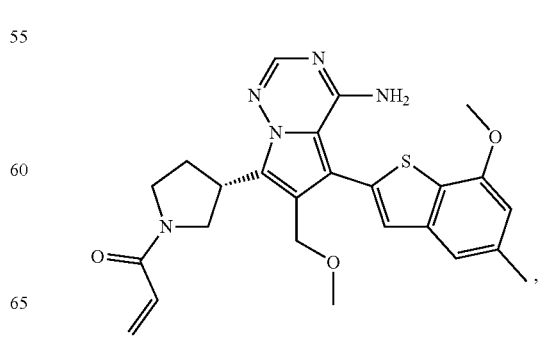

-continued
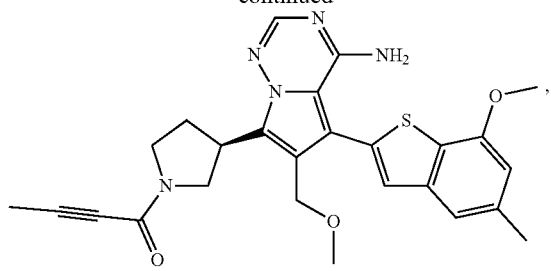
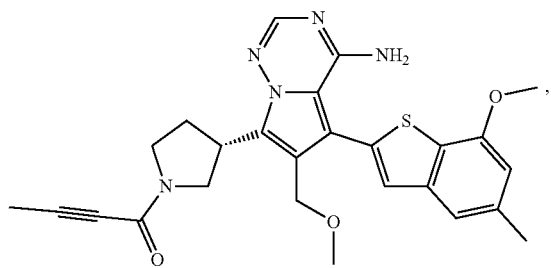
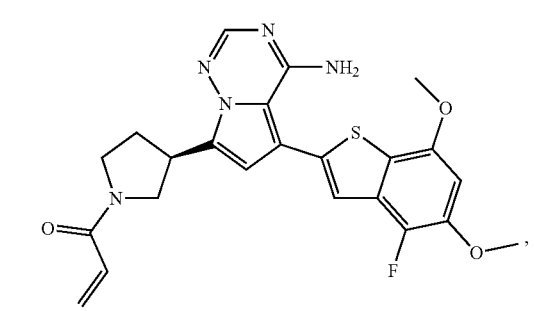
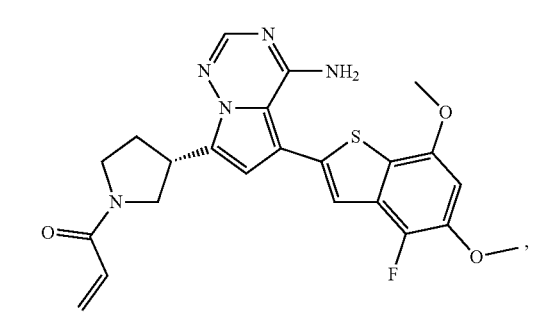
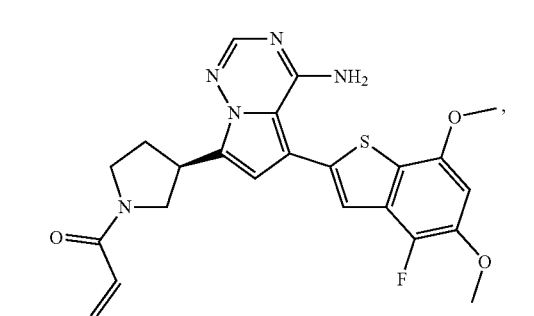
-continued
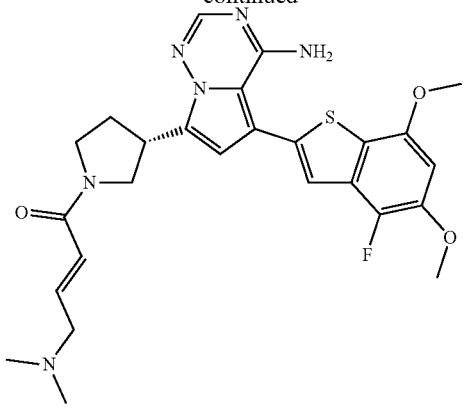
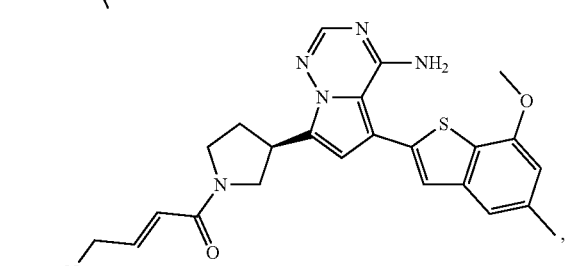
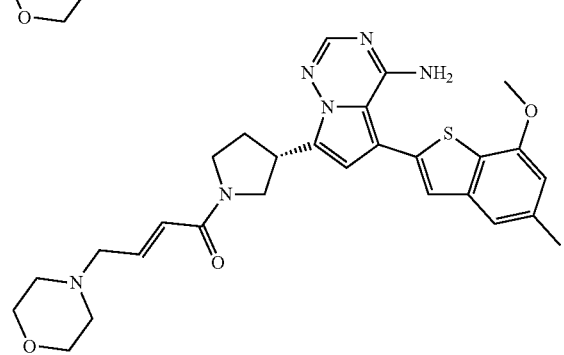
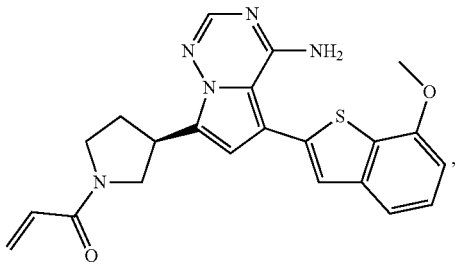
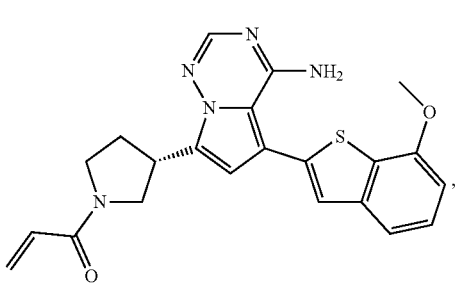

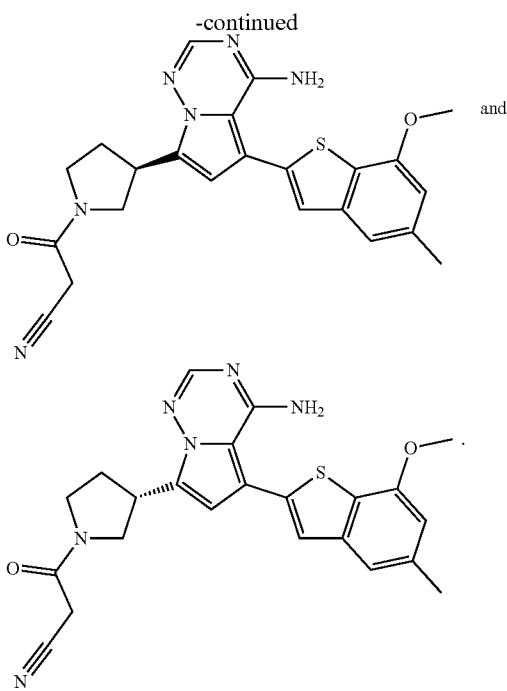

The present invention further provides a pharmaceutical composition, which contains a therapeutically effective amount of the above-mentioned compound or a pharmaceutically acceptable salt thereof, and a pharmaceutically acceptable carrier.

The present invention further provides use of the above-mentioned compound or a pharmaceutically acceptable salt thereof or the above-mentioned composition in the manufacture of a medicament for treating an FGFR-related disease.

In some embodiments of the present invention, the above-mentioned FGFR-related disease refers to a solid tumor.

TECHNICAL EFFECT

Some compounds in the present invention exhibit higher inhibitory activities on wild-type and mutant FGFRs.

Related Definitions

Unless otherwise stated, the following terms and phrases used herein are intended to have the following meanings. A particular term or phrase should not be considered uncertain or undistinct without a special definition but should be understood in its ordinary meaning. When a trading name appears herein, it is intended to refer to its corresponding commercial product or its active ingredient. The term "pharmaceutically acceptable" as used herein refers to those compounds, materials, compositions, and/or dosage forms which are, within the scope of sound medical judgment, suitable for use in contact with the tissues of humans and animals without undue toxicity, irritation, allergic response or other problems or complications, and are commensurate with a reasonable benefit/risk ratio.

The term "pharmaceutically acceptable salt" refers to a salt of the compound of the present invention, prepared from a compound having a specific substituent found in the present invention and a relatively non-toxic acid or base. When the compound of the present invention contains a relatively acidic functional group, a base addition salt can be obtained by contacting a sufficient amount of a base with a neutral form of such a compound in a pure solution or a suitable inert solvent. The pharmaceutically acceptable base addition salts include sodium, potassium, calcium, ammonium, organic ammonia or magnesium salts or similar salts. When the compound of the present invention contains a relatively basic functional group, an acid addition salt can be obtained by contacting a sufficient amount of an acid with a neutral form of such a compound in a pure solution or a suitable inert solvent. Examples of pharmaceutically acceptable acid addition salts include salts of inorganic acids, including, for example, hydrochloric acid, hydrobromic acid, nitric acid, carbonic acid, hydrocarbonate, phosphoric acid, monohydric phosphate, dihydric phosphate, sulfuric acid, hydrosulfate, hydroiodic acid, phosphorous acid, and the like; salts of organic acids, including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; salts of amino acids (such as arginine); and salts of organic acids such as glucuronic acid (see Berge et al., "Pharmaceutical Salts", Journal of Pharmaceutical Science 66: 1-19 (1977)). Certain specific compounds of the present invention contain both basic and acidic functionalities, and therefore can be converted into any of base or acid addition salts thereof.

Preferably, a salt is contacted with a base or an acid in a conventional manner, and then the parent compound is isolated, thereby regenerating the neutral form of the compound. The parent form of a compound differs from its various salt forms in certain physical properties, such as different solubilities in a polar solvent.

As used herein, a "pharmaceutically acceptable salt" is a derivative of the compound of the present invention, wherein the parent compound is modified by forming a salt with an acid or with a base. Examples of pharmaceutically acceptable salts include, but are not limited to, inorganic or organic acid salts of bases such as amines, alkali metal or organic salts of acids such as carboxylic acids, and the like. Pharmaceutically acceptable salts include conventional non-toxic salts or quaternary ammonium salts of the parent compound, such as salts formed from non-toxic inorganic or organic acids. Conventional non-toxic salts include, but are not limited to, those derived from inorganic and organic acids selected from 2-acetoxybenzoic acid, 2-hydroxyethanesulfonic acid, acetic acid, ascorbic acid, benzenesulfonic acid, benzoic acid, bicarbonate, carbonic acid, citric acid, ethylene diamine tetraacetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, iminodiacetic acid, succinic acid, sulfamic acid, sulfanilic acid, sulfuric acid, tannic acid, tartaric acid, and p-toluenesulfonic acid.

The pharmaceutically acceptable salt of the present invention can be synthesized from the parent compound containing an acid group or a base group by a conventional chemical method. Generally, such salts are prepared by reacting these compounds in the form of free acid or base with a stoichiometric amount of an appropriate base or acid in water or an organic solvent or a mixture of the two. Generally, a non-aqueous medium such as ethyl ether, ethyl acetate, ethanol, isopropanol, or acetonitrile is preferred.

The compounds of the present invention may exist in specific geometric or stereoisomeric forms. The present invention contemplates all such compounds, including cis- and trans-isomers, (−)- and (+)-pairs of enantiomers, (R)- and (S)-enantiomers, diastereoisomers, (D)-isomers, (L)-isomers, the racemic mixtures thereof, and other mixtures thereof, such as enantiomer or diastereoisomer-enriched mixtures, all of which fall within the scope of the invention. Additional asymmetric carbon atoms may be present in a substituent such as an alkyl group. All these isomers and their mixtures are included in the scope of the present invention.

Unless otherwise stated, the terms "enantiomers" or "optical isomers" refer to stereoisomers in mirror image relationship to each other.

Unless otherwise stated, the term "cis-trans isomer" or "geometric isomer" is caused by the inability of double bonds or single bonds of ring-forming carbon atoms to rotate freely.

Unless otherwise stated, the term "diastereoisomer" refers to a stereoisomer for which each of the molecules has two or more chiral centers and the molecules are in a non-mirror image relationship between each other.

Unless otherwise stated, "(D)" or "(+)" means the dextrorotation, "(L)" or "(−)" means the levorotation, and "(DL)" or "(±)" means the racemic.

Unless otherwise stated, the absolute configuration of a stereo-center is expressed with a wedge-shape solid line bond ($\nearrow$) and a wedge-shape dashed line bond ($\nearrow$) the relative configuration of a stereo-center is expressed with a straight-shape solid line bond ($\nearrow$) and a straight-shape dashed line bond ($\nearrow$), the wedge-shape solid line bond ($\nearrow$) and/or the wedge-shape dashed line bond ($\nearrow$) are expressed with a wavy line ($\nearrow$), or the straight-shape solid line bond ($\nearrow$) and/or the straight-shape dashed line bond ($\nearrow$) are expressed with a wavy line ($\nearrow$).

The compounds of the present invention may exist in specific forms. Unless otherwise stated, the term "tautomer" or "tautomeric form" means that at room temperature, the isomers having different functional groups are in dynamic equilibrium and can be quickly converted to each other. If tautomers are possible (for example, in solution), the chemical equilibrium of the tautomers can be reached. For example, proton tautomers (also known as prototropic tautomers) include interconversions via proton migration, such as keto-enol isomerization and imine-enamine isomerization. Valence tautomers include the recombination of some bonding electrons for mutual conversion. Among others, a specific example of the keto-enol tautomerization is the interconversion between two tautomers of pentane-2,4-dione and 4-hydroxypent-3-en-2-one.

Unless otherwise stated, the term "enriched in an isomer", "isomerically enriched", "enriched in an enantiomer" or "enantiomerically enriched" refers to the content of an isomer or enantiomer is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee value) is 80%.

Optically active (R)- and (S)-isomers, as well as D and L isomers, may be prepared with chiral synthesis, or chiral reagents, or other conventional techniques. If an enantiomer of the compound of the present invention is desired, it can be prepared by asymmetric synthesis or derivatization with a chiral auxiliary, in which the resulting diastereomeric mixture is separated, and the pure desired enantiomer is provided under the assistance of the group cleavage. Alternatively, when the molecule contains a basic functional group (such as an amino group) or an acidic functional group (such as a carboxyl group), a diastereomeric salt is formed with an appropriate optically active acid or base, and then the diastereomeric resolution is performed with the conventional method well-known in the art, and then the pure enantiomer is recovered and obtained. In addition, the separation of enantiomers and diastereomers is usually accomplished by using chromatography, which employs a chiral stationary phase and is optionally combined with chemical derivatization (such as the generation of carbamate from amine). The compounds of the invention may contain an atomic isotope in an unnatural proportion on one or more of the atoms constituting the compound. For example, compounds can be labeled with radioisotopes, such as tritium ($^3$H), iodine-125 ($^{125}$I), or C-14 ($^{14}$C). Transformations of all isotopic compositions of the compounds of the present invention, whether radioactive or not, are included within the scope of the present invention.

"Optional" or "optionally" refers to events or conditions described later that may, but need not, occur, and this description includes situations in which the events or conditions occur and situations in which the events or conditions do not occur.

The term "substituted" refers to the replacement of any one or more hydrogen atoms that may include deuterium and hydrogen variants on a specific atom with a substituent, as long as the valence of the specific atom is normal and the substituted compound is stable. When the substituent is oxygen (=O), it means that two hydrogen atoms are substituted. Oxygen substitution does not occur on an aromatic group. The term "optionally substituted" means that it may or may not be substituted, and unless otherwise specified, the kind and number of substituents may be arbitrary on the basis of chemically achievable.

When any variable (such as R) appears more than once in the composition or structure of a compound, its definition in each case is independent. Thus, for example, if a group is substituted with 0-2 R substituents, the group may be optionally substituted by at most two R substituents, and for each substituent, R has an independent option. In addition, the combination of substituents and/or variants thereof are permitted only if such combination results in a stable compound.

When the number of a linking group is 0, such as —(CRR)$_0$—, it means that the linking group is a single bond.

When one of the variables is selected from a single bond, the two groups connected thereto are directly connected. For example, when L represents a single bond in A-L-Z, the structure is actually A-Z.

When a substituent is vacant, it represents that the substituent is not present. For example, if X in A-X is vacant, it represents that the structure is actually A. When a substituent may be attached to more than one atom on a ring, this substituent may be bonded to any atom on the ring. For example, the structure unit

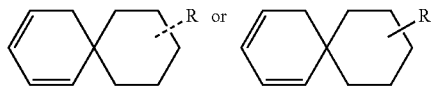

represents that the substitution with the R substituent may appear on any position of the cyclohexyl or cyclohexadiene. In case of not indicating which atom in the listed substituent will be attached to the group to be substituted, this substituent may be attached via any atom thereof. For example, a pyridyl group as a substituent group may be attached to a group to be substituted via any carbon atom on the pyridine ring. In case of not indicating the linking direction of the listed linking group, its linking direction is arbitrary. For example, in

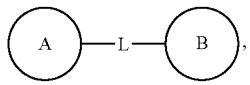

the linking group L is -M-W—; at this time, -M-W— can either link ring A and ring B in the same direction as the reading order from the left to the right to form

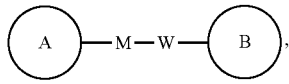

or link ring A and ring B in the direction opposite to the reading order from the left to the right to form

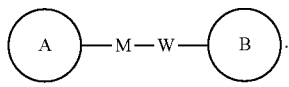

The combination of the linking group, substituents and/or variants thereof are permitted only if such combination results in a stable compound.

Unless otherwise specified, "ring" represents substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a linked ring, a spiro ring, a fused ring or a bridged ring. The number of atoms on a ring is usually defined as the member number of rings. For example, "5-7 membered ring" means 5-7 atoms arranged in a circle. Unless otherwise specified, the ring optionally contains 1-3 heteroatoms. Thus, "5-7 membered ring" includes, for example, phenyl, pyridinyl, and piperidinyl; on the other hand, the term "5-7 membered heterocycloalkyl ring" includes pyridyl and piperidyl, but does not include phenyl.

The term "ring" also includes a ring system containing at least one ring, each of which "ring" independently meets the above definition.

Unless otherwise specified, the term "heterocycle" or "heterocyclyl" means a stable heteroatom or hetero group-containing monocyclic, bicyclic, or tricyclic ring, which may be saturated, partially unsaturated, or unsaturated (aromatic) and contain carbon atoms and 1, 2, 3, or 4 ring heteroatoms independently selected from N, O, and S, wherein any of the above heterocycles can be fused to a benzene ring to form a bicyclic ring. Nitrogen and sulfur heteroatoms can optionally be oxidized (i.e., NO and S(O)p, where p is 1 or 2). The nitrogen atom may be substituted or unsubstituted (i.e., N or NR, where R is H or other substituents as defined herein). The heterocycle can be attached to a side group of any heteroatom or carbon atom to form a stable structure. If the resulting compound is stable, the heterocycle described herein can undergo the substitution at the carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5, 6, 7-membered monocyclic or bicyclic or 7, 8, 9 or 10-membered bicyclic heterocyclic aromatic ring, which contains carbon atoms and 1, 2, 3 or 4 ring heteroatoms independently selected from N, O and S. The nitrogen atom may be substituted or unsubstituted (i.e., N or NR, where R is H or other substituents as defined herein). Nitrogen and sulfur heteroatoms can optionally be oxidized (i.e., NO and S(O)p, where p is 1 or 2). It is worth noting that the total number of S and O atoms on the aromatic heterocycle does not exceed 1. The bridged ring is also included in the definition of the heterocycle. The bridged ring is formed when one or more atoms (i.e., C, O, N, or S) connect two non-adjacent carbon or nitrogen atoms. The preferred bridged ring includes but is not limited to, one carbon atom, two carbon atoms, one nitrogen atom, two nitrogen atoms, and one carbon-nitrogen group. It is worth noting that a bridge always converts a single ring into a tricyclic ring. In the bridged ring, the substituent on the ring may also appear on the bridge.

The example of the heterocycle compound includes, but is not limited to, acridinyl, azocinyl, benzimidazolyl, benzofuranyl, mercapto benzofuranyl, mercapto benzophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridino-oxazole, pyridino-imidazole, pyridino-thiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1, 2,3-triazolyl, 2H-1,2,3-triazolyl, 1H-1,2,4-triazolyl, 4H-1,2,4-triazolyl, and xanthenyl. Also included are the fused-ring compound and the spiro-ring compound.

Unless otherwise specified, the term "hydrocarbyl" or its subordinate concept (e.g. alkyl, alkenyl, alkynyl, aryl and the like), by itself or as part of another substituent, refers to a linear, branched-chain or cyclic hydrocarbon radical or any combination thereof. They can be fully saturated (e.g. alkyl), mono- or polyunsaturated (e.g. alkenyl, alkynyl, and aryl), can be mono-, or poly-substituted, can be monovalent (e.g. methyl), divalent (e.g. methylene) or multivalent (e.g. methynyl), can also include a divalent or multivalent group, have a specified number of carbon atom (for example, $C_1$-$C_{12}$ indicates 1-12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$, and $C_{12}$; $C_{3-12}$ is selected from $C_3$, $C_4$, $C_5$, $C_6$, $C_7$, $C_8$, $C_9$, $C_{10}$, $C_{11}$, and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but is not limited to alkyl, alkenyl, and alkynyl. The aromatic hydrocarbyl includes but is not limited to 6-12 membered aromatic hydrocarbyl such as phenyl, naphthalenyl and the like. In some embodiments, the term "hydrocarbyl" refers to a linear or branched group or a combination thereof which can be fully saturated, mono- or polyunsaturated, and can include a divalent or multivalent group. The example of the saturated hydrocarbyl group includes, but is not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-pentyl, n-hexyl, n-heptyl, n-octyl, and the similar groups. The unsaturated hydrocarbyl has one or more than one double or triple bonds, and the example thereof includes but is not limited to ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its subordinate concept (e.g. heteroalkyl, heteroalkenyl, heteroalkynyl, heteroaryl and the like), by itself or in combination of another term, refers to a stable linear, branched or cyclic hydrocarbon group or any combination thereof, which is composed of a specified number of carbon atoms and at least one heteroatom. In some embodiments, the term "heteroalkyl", by itself or in the combination of another term, refers to a stable linear or branched hydrocarbon group or any combination thereof, which is composed of a specified number of carbon atoms and at least one heteroatom. In a specific embodiment, the heteroatom is selected from B, O, N, and S, wherein the nitrogen and sulfur atoms are optionally oxidized and the nitrogen atom is optionally quaternized. The heteroatom or the hetero group can be located at any interior position of a heterohydrocarbyl, including the position where the hydrocarbyl attaches to the rest part of the molecule. But the terms "alkoxy", "alkylamino" and "alkylthio" (or alkoxyl in which O is replaced with S) belong to the idiomatic expression and refer to an alkyl group connected to the remaining part of the molecule via an oxygen atom, an amino group or a sulfur atom respectively. The example includes, but is not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms can be consecutive, for example, —$CH_2$—NH—$OCH_3$.

Unless otherwise specified, the term "cyclohydrocarbyl", "heterocyclohydrocarbyl" or its subordinate concept (e.g. aryl, heteroaryl, cycloalkyl, heterocycloalkyl, cycloalkenyl, heterocycloalkenyl, cycloalkynyl, heterocycloalkynyl and the like) by itself or in combination with another term refers to cyclized "hydrocarbyl" and "heterohydrocarbyl" respectively. Furthermore, for heterohydrocarbyl or heterocyclohydrocarbyl (e.g. heteroalkyl and heterocycloalkyl), the heteroatom can occupy the position where the heterocycle attaches to the remaining position of the molecule. The example of the cyclohydrocarbyl includes, but is not limited to, cyclopentyl, cyclohexyl, 1-cyclohexenyl, 3-cyclohexenyl, cycloheptyl and the like. The non-limiting example of heterocycloalkyl includes 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuran indole-3-yl, tetrahydro-thiophen-2-yl, tetrahydro-thiophen-3-yl, 1-piperazinyl and 2-piperazinyl.

Unless otherwise specified, the term "alkyl" refers to a straight or branched saturated hydrocarbyl, which can be mono-substituted (e.g. —$CH_2$F) or poly-substituted (e.g. —$CF_3$), and can be monovalent (e.g. methyl), divalent (e.g. methylene) or multivalent (e.g. methenyl). The example of alkyl includes methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, which can be mono-substituted or poly-substituted and can be monovalent, divalent or multivalent. The example of alkenyl includes ethenyl, propenyl, butenyl, pentenyl, hexenyl, 1,3-butadienyl, 1,3-pentadienyl, 1,3-hexadienyl, and the like.

Unless otherwise specified, the term "alkynyl" refers to an alkyl group having one or more than one carbon-carbon triple bonds at any position on the chain, which can be mono-substituted or poly-substituted and can be monovalent, divalent or multivalent. The example of alkynyl includes ethynyl, propynyl, butynyl, pentynyl and the like.

Unless otherwise specified, cycloalkyl includes any stable cyclic or polycyclic hydrocarbyl, any carbon atom of which is saturated, and which can be mono-substituted or poly-substituted and can be monovalent, divalent or multivalent. The example of cycloalkyl includes, but is not limited to, cyclopropyl, norbornanyl, [2.2.2]bicyclooctane, [4.4.0]bicyclodecane and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Unless otherwise specified, the example of haloalkyl includes, but is not limited to trifluoromethyl, trichloromethyl, pentafluoroethyl, and pentachloroethyl.

"Alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. The example of alkoxy includes, but is not limited to methoxy, ethoxy, n-propoxy, isopropoxy, n-butoxy, sec-butoxy, tert-butoxy, n-pentyloxy and S-pentoxy.

The compound of the present invention can be prepared by a variety of synthesis methods well known to those skilled in the art, including the following enumerative embodiments, the embodiments formed by the following enumerative embodiments in combination with other chemical synthesis methods and the equivalent substitute modes well known to those skilled in the art. The preferred embodiment includes but is not limited to the examples of the present invention.

All of the solvents used in the present invention are commercially available. The present invention adopts the following abbreviations: aq represents water; HATU represents O-(7-aza-benzotriazole-1-yl)-N,N,N',N'-tetramethyl-uronium hexafluorophosphate; EDC represents N-(3-dimethylaminopropyl)-N'-ethyl carbodiimide hydrochloride; m-CPBA represents 3-chloroperoxy benzoic acid; eq represents equivalent, equivalent amount; CDI represents carbonyl diimidazole; DCM represents methylene chloride; PE represents petroleum ether; DIAD represents diisopropyl azodiformate; DMF represents N,N-dimethyl formamide; DMSO represents dimethyl sulfoxide; EtOAc represents ethyl acetate; EtOH represents ethanol; MeOH represents methanol; CBz represents benzyloxycarbonyl, an amine protecting group; BOC represents tert-butoxylcarbonyl, an amine protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS2 represents carbon bisulfide; TsOH represents paratoluenesulfonic acid; NFSI represents N-fluoro-N-(benzenesulfonyl)benzenesulfonamide; NCS represents 1-chloro-pyrrolidine-2,5-dione; n-Bu4NF represents tetrabutylammonium fluoride; iPrOH represents 2-propyl alcohol; mp represents melting point; LDA represents lithium diisopropylamide.

Compounds are named manually or by ChemDraw® software, and the commercially available compounds use their supplier's directory names.

DETAILED DESCRIPTION

The present invention will be specifically described below by way of examples, but it does not imply any disadvantageous limitation to the present invention. The present invention has been described in detail herein, and its specific embodiments are also disclosed. It will be obvious to those skilled in the art that various changes and improvements can be made to the specific embodiments of the present invention without departing from the spirit and scope of the present invention.

Reference Example 1: WXR1

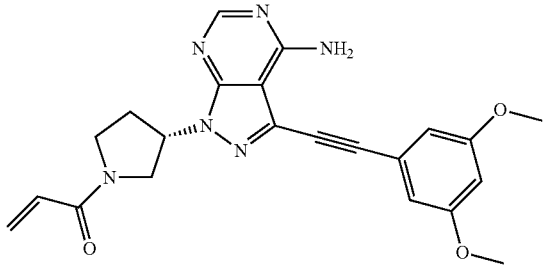 [SMILES: C=CC(=O)N1CC[C@H](n2nc(C#Cc3cc(OC)cc(OC)c3)c3c(N)ncnc32)C1]

Compound WXR1 was synthesized with reference to the route reported in the patent application WO2015008844. $^1$H NMR (400 MHz, DMSO-d$_6$) δ=8.40 (d, J=3.0 Hz, 1H), 6.93 (d, J=2.5 Hz, 2H), 6.74-6.52 (m, 2H), 6.20-6.16 (m, 1H), 5.74-5.69 (m, 1H), 5.45-5.61 (m, 1H), 4.12-3.90 (m, 2H), 3.90-3.79 (m, 8H), 2.47-2.30 (m, 2H). MS m/z: 419.1 [M+H]$^+$.

Reference Example 2: WXR2

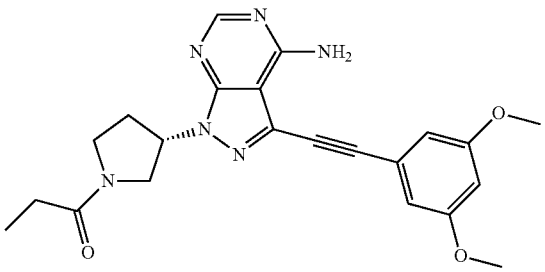 [SMILES: CCC(=O)N1CC[C@H](n2nc(C#Cc3cc(OC)cc(OC)c3)c3c(N)ncnc32)C1]

Compound WXR2 was synthesized with reference to the route reported in the patent application WO2015008844. $^1$H NMR (400 MHz, deuterated methanol) δ=8.28 (s, 1H), 6.83 (br s, 2H), 6.60 (d, J=2.4 Hz, 1H), 5.65-5.44 (m, 1H), 4.12-3.98 (m, 1H), 3.97-3.88 (m, 2H), 3.83 (s, 6H), 3.82-3.74 (m, 1H), 3.74-3.63 (m, 1H), 2.63-2.53 (m, 1H), 2.51-2.35 (m, 3H), 1.22-1.12 (m, 3H). MS m/z: 421.1 [M+H]$^+$.

Reference Example 3: WXR3

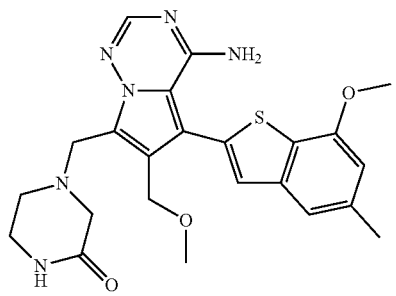 [SMILES: COCc1c(-c2cc3cc(C)cc(OC)c3s2)c2c(N)ncnn2c1CN1CCNC(=O)C1]

Reference Example 4: Synthesis of AZD4547

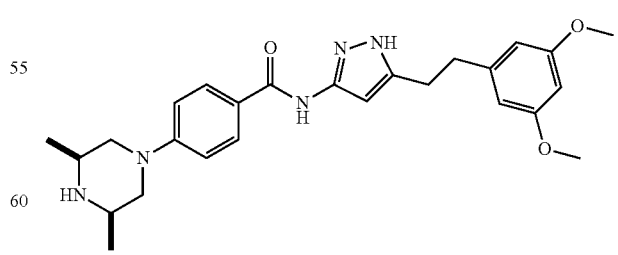

AZD4547 was synthesized with reference to the route reported in the patent application WO2009153592. $^1$H NMR (400 MHz, deuterated methanol) δ: 7.93 (d, J=8.8 Hz, 2H), 7.13 (d, J=8.8 Hz, 2H), 6.37 (s, 2H), 6.33 (s, 1H), 6.31 (s, 1H), 4.12-4.09 (m, 2H), 3.74 (s, 6H), 3.51-3.48 (m, 2H), 2.99-2.93 (m, 4H), 2.84 (t, J=12.4 Hz, 2H), 1.42 (d, J=6.4 Hz, 6H). MS m/z: 464.4 [M+H]$^+$.

Reference Example 5: Synthesis of BGJ398

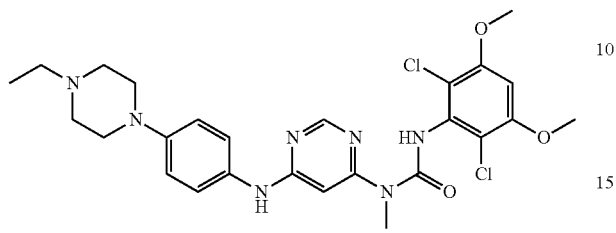

BGJ398 was synthesized with reference to the route reported in the patent application WO2006000420. $^1$H NMR (400 MHz, deuterated methanol) δ: 8.40 (s, 1H), 7.46 (d, J=8.8 Hz, 2H), 7.09 (d, J=8.8 Hz, 2H), 6.82 (s, 1H), 6.49 (s, 1H), 3.96 (s, 6H), 3.86 (d, J=12.0 Hz, 2H), 3.69 (d, J=12.0 Hz, 2H), 3.43 (s, 3H), 3.33-3.20 (m, 4H), 3.08 (t, J=12.4 Hz, 2H), 1.42 (t, J=7.2 Hz, 3H). MS m/z: 560.1 [M+H]$^+$.

Reference Example 6: JNJ493

JNJ493 was purchased from Shanghai Haoyuan Biotechnology Co., Ltd. (CAS: 1346242-81-6). $^1$H NMR (400 MHz, deuterated methanol) δ: 8.86 (s, 1H), 8.41 (s, 1H), 8.24 (s, 1H), 7.77 (d, J=9.2 Hz, 1H), 7.35 (dd, J=2.4, 9.3 Hz, 1H), 7.24 (d, J=2.4 Hz, 1H), 6.53-6.43 (m, 3H), 4.08-3.97 (m, 5H), 3.80 (s, 6H), 2.97 (t, J=7.2 Hz, 2H), 2.90-2.78 (m, 1H), 1.10 (d, J=6.4 Hz, 6H). MS m/z: 447.2 [M+H]$^+$.

Reference Example 7: WXR4

Compound WXR4 was synthesized with reference to the route reported in the patent application US20140142084. $^1$H NMR (400 MHz, deuterated methanol) δ: 8.41 (s, 2H), 8.13 (s, 1H), 7.86 (s, 1H), 6.98 (t, J=8.3 Hz, 1H), 5.25 (s, 2H), 4.34 (t, J=5.0 Hz, 2H), 3.95 (t, J=5.3 Hz, 2H), 3.91 (s, 6H). MS m/z: 408.1 [M+H]$^+$.

Intermediate A1

Synthesis Route

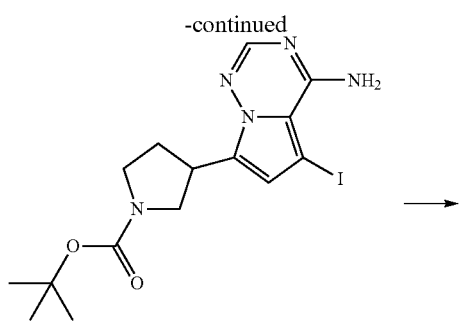

A1

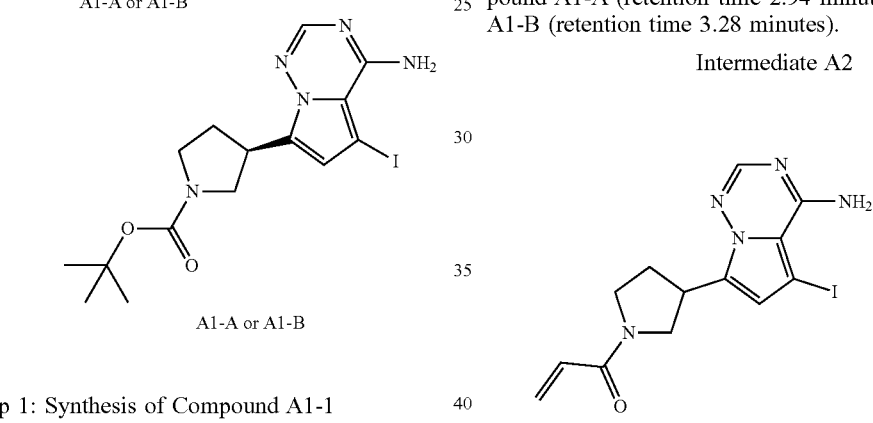

A1-A or A1-B

A1-A or A1-B

Step 1: Synthesis of Compound A1-1

At room temperature, 4-amino-7-bromopyrrolo[2,1-f][1,2,4]triazine (3.00 g, 14.1 mmol, 1.00 eq) was firstly dissolved in a mixed solution of 1,4-dioxane (40 mL) and water (8 mL), and then N-Boc-2,5-dihydro-1H-pyrrole-1-pinacol borate (4.36 g, 14.8 mmol, 1.05 eq), potassium phosphate (8.97 g, 42.2 mmol, 3.00 eq) and 1,1'-bis(diphenylphosphino)ferrocene palladium chloride (1.03 g, 1.41 mmol, 0.10 eq) were successively added to the mixed solution. Under the nitrogen protection, the reaction solution was heated to 80° C. and stirred for 2 hours. After the completion of the reaction, the reaction solution was cooled to 25° C. and poured into 20 mL of water. A black solid was formed. The black solid was collected by filtration, and then dissolved in a mixed solution of dichloromethane/methanol (100 mL, 5/1) and filtered again. The filtrate was dried over anhydrous sodium sulfate, and the organic solvent was removed by rotary evaporation under reduced pressure to obtain a crude product. The crude product was slurried with ethyl acetate (30 mL) and filtered to obtain the Compound A1-1. LCMS (ESI) m/z: 302.1 [M+H]+, 1H NMR (400 MHz, deuterated chloroform) δ=8.05 (s, 1H), 6.98-6.84 (m, 1H), 6.72-6.54 (m, 2H), 4.67-4.49 (m, 2H), 4.44-4.30 (m, 2H).

Step 2: Synthesis of Compound A1-2

At room temperature, palladium hydroxide (615 mg, 438 μmol) was added to a solution of A1-1 (1.20 g, 3.98 mmol, 1.00 eq) in methanol (30 mL). After being replaced with hydrogen 3 times, the reaction solution was heated to 50° C. Under 50 psi hydrogen, the reaction solution was stirred for 2 hours. The reaction solution was cooled to room temperature, and filtered to remove the catalyst. The solvent was removed from the filtrate by rotary evaporation under reduced pressure to obtain A1-2. 1H NMR (400 MHz, deuterated methanol) δ: 7.80 (s, 1H), 6.86 (d, J=4.4 Hz, 1H), 6.53 (d, J=4.4 Hz, 1H), 3.96-3.79 (m, 2H), 3.60-3.51 (m, 1H), 3.49-3.38 (m, 2H), 2.39-2.36 (m, 1H), 2.19-2.13 (m, 1H), 1.49 (d, J=3.6 Hz, 9H).

Step 3: Synthesis of Compound A1

At room temperature, iodosuccinimide (26.7 g, 119 mmol, 3.00 eq) was added in batch to a solution of A1-2 (12.0 g, 39.6 mmol, 1.00 eq) in N,N-dimethyl formamide (150 mL). After the reaction solution was stirred at room temperature for 1 hour, the reaction solution was slowly added to ice water (200 mL), and a solid was formed. The solvent was removed by filtration, and the filter cake was dried by rotary evaporation under reduced pressure to obtain the Compound A1. The Compound A1 was chirally resolved (column: IC (250 mm*50 mm, 10 μm); mobile phase: [0.1% ammonia water/ethanol]; B %: 30%-30%) to obtain Compound A1-A (retention time 2.94 minutes) and Compound A1-B (retention time 3.28 minutes).

Intermediate A2

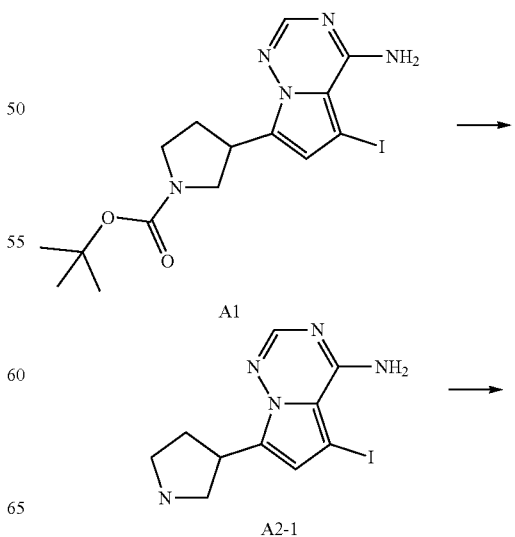

Synthesis Route

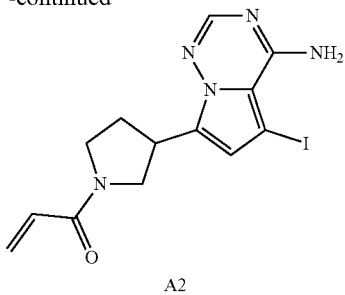

A2

Step 1: Synthesis of Compound A2-1

At room temperature, hydrochloric acid/ethyl acetate (4M, 20.00 mL, 6.87 eq) was slowly added to a solution of A1 (5.00 g, 11.65 mmol, 1.00 eq) in ethyl acetate (30 mL). The reaction solution was stirred for two hours and then filtered. The solvent was removed from the filter cake by rotary evaporation under reduced pressure to obtain A2-1 hydrochloride. LCMS (ESI) m/z: 329.9 [M+H]$^+$, $^1$H NMR (400 MHz, deuterated methanol) δ=8.11 (s, 1H), 7.20 (s, 1H), 4.12 (m, 1H), 3.84 (m, 1H), 3.67-3.54 (m, 1H), 3.51-3.37 (m, 2H), 2.71-2.51 (m, 1H), 2.35-2.27 (m, 1H).

Step 2: Synthesis of Compound A2

At 0° C., triethylamine (3.60 g, 35.55 mmol, 4.93 mL, 5.00 eq) and acryloyl chloride (707.88 mg, 7.82 mmol, 1.10 eq) were successively added to a solution of A2-1 (2.60 g, 7.11 mmol, 1.00 eq, hydrochloride) in a dichloromethane (20.00 mL). After stirring for 1 hour, the reaction solution was poured into 50 mL water. After the phase separation, the aqueous phase was extracted with dichloromethane (20 mL×5). The organic phases were combined, dried over anhydrous sodium sulfate, and filtered. The solvent was removed under reduced pressure to obtain A2. LCMS (ESI) m/z: 384.0 [M+H]$^+$, 406.0 [M+Na]$^+$.

Intermediate A3

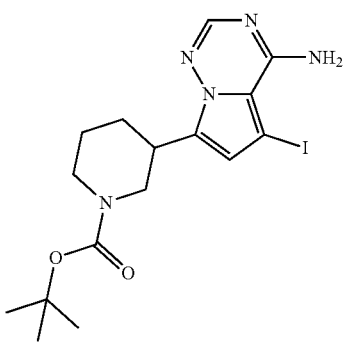 [SMILES: CC(C)(C)OC(=O)N1CCCC(c2cc(I)c3c(N)ncnn23)C1]

It was synthesized with reference to the synthesis method of Intermediate A1.

Intermediate B1

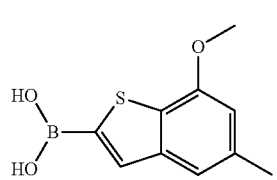

Synthesis Route

A solution of 7-methoxy-5-methylbenzothiophene (2.00 g, 11.22 mmol, 1.00 eq) in tetrahydrofuran (20.00 mL) was cooled to −70° C. A solution of butyllithium in n-hexane (2.5M, 8.98 mL, 2.00 eq) was slowly dropwise to the cooled solution. After the dropwise addition, the stirring lasted for 1 hour. Then triisopropylboronic acid (2.11 g, 11.22 mmol, 1.00 eq) was added. After the addition was complete, the stirring lasted for 1 hour. Water (10 mL) was added dropwise to quench the reaction. The quenched reaction mixture was concentrated to remove tetrahydrofuran. The residue was firstly washed with petroleum ether (50 mL) and then adjusted with dilute hydrochloric acid to a pH value of 5. A white solid was produced. After filtration, the filter cake was washed with water (50 mL) and then dried under vacuum to obtain intermediate B1. $^1$H NMR (400 MHz, deuterated chloroform) δ=7.72 (s, 1H), 7.28 (s, 1H), 6.67 (s, 1H), 4.01 (s, 3H), 2.50 (s, 3H).

Intermediate B2

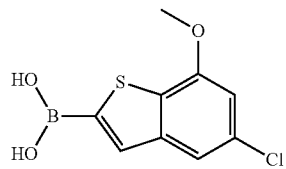

4-chloro-2-methoxythiophenol was prepared from the starting material 2-bromo-5-chloro anisole (with reference to J. O. Jilek et al., Collection of Czechoslovak Chemical Communications, Vol. 43, 1978, p. 1747-1759), and Intermediate B2 was synthesized with reference to the synthesis method of B1. $^1$H NMR (400 MHz, deuterated methanol) δ=7.75 (s, 1H), 7.46 (s, 1H), 6.87 (s, 1H), 4.00 (s, 3H).

Intermediate B3

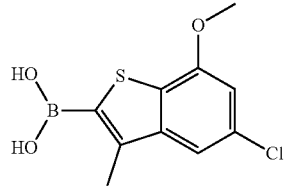 [SMILES: COc1cc(Cl)cc2c(C)c(B(O)O)sc12]

Synthesis Route

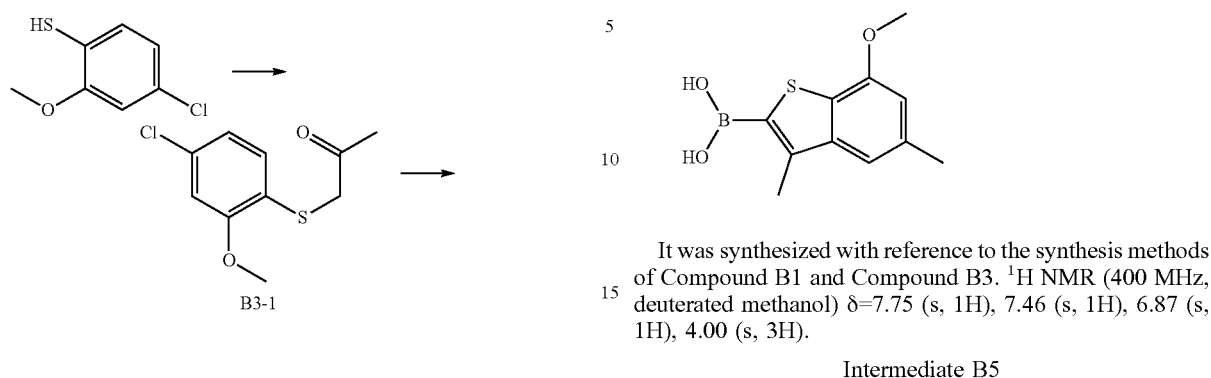

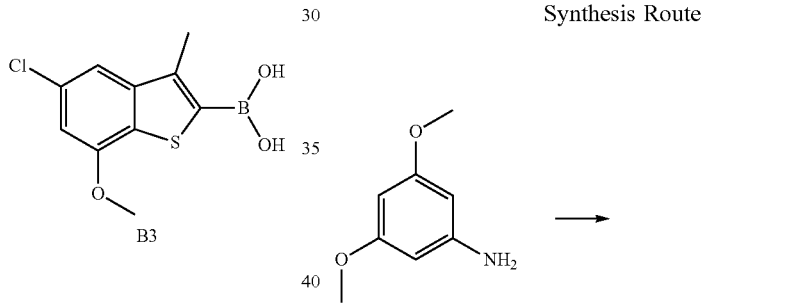

Step 1: Synthesis of Compound B3-1

At room temperature, cesium carbonate (149.24 g, 458.06 mmol, 2.00 eq) was added to a solution of 4-chloro-2-methoxythiophenol (40.00 g, 229.03 mmol, 1.00 eq) and 1-chloroacetone (31.78 g, 343.55 mmol, 1.50 eq) in N,N-dimethyl formamide (500.00 mL). After stirring for 16 hours under the protection of nitrogen, the reaction solution was added to 250 mL of water and the mixture was extracted with ethyl acetate (100 mL) 3 times. The organic phases were combined, washed with a saturated saline solution (250 mL) 3 times, dried over anhydrous sodium sulfate, and filtered. The organic solvent was removed from the filtrate by rotary evaporation under reduced pressure to obtain a crude product. The crude product was purified by column chromatography (petroleum ether to petroleum ether/ethyl acetate=10/1) to obtain Compound B3-1. $^1$H NMR (400 MHz, deuterated chloroform) δ=7.25 (d, J=8.0 Hz, 1H), 7.16 (d, J=8.0 Hz, 1H), 6.84-6.80 (m, 1H), 3.80-3.76 (m, 2H), 3.72 (s, 3H), 1.35 (s, 3H).

Step 2-3: Intermediate B3 was synthesized with reference to the synthesis method of B1. $^1$H NMR (400 MHz, deuterated methanol) δ=7.25 (d, J=1.6 Hz, 1H), 7.16 (d, J=2.0 Hz, 1H), 3.87 (s, 2H), 2.41 (s, 3H).

Intermediate B4

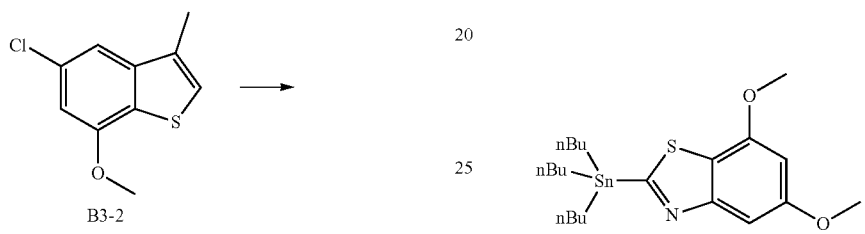

It was synthesized with reference to the synthesis methods of Compound B1 and Compound B3. $^1$H NMR (400 MHz, deuterated methanol) δ=7.75 (s, 1H), 7.46 (s, 1H), 6.87 (s, 1H), 4.00 (s, 3H).

Intermediate B5

Synthesis Route

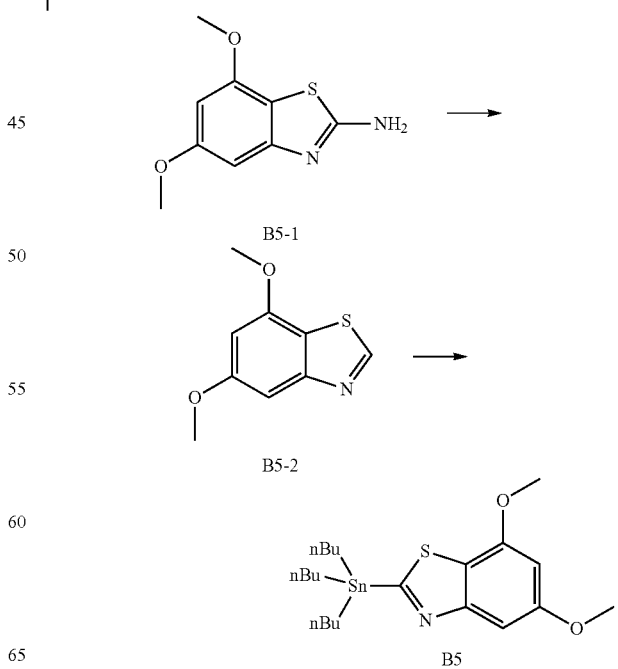

35

Step 1: Synthesis of Compound B5-1

At room temperature, 3,5-dimethoxyaniline (43.00 g, 280.72 mmol, 1.00 eq) and ammonium thiocyanate (47.01 g, 617.58 mmol, 2.20 eq) were firstly dissolved in glacial acetic acid (500 mL). Then the reaction solution was cooled to 10° C. in an ice water bath. Liquid bromine (43.00 g, 280.72 mmol, 1.00 eq) was slowly added dropwise over 1 hour. The reaction was stirred under nitrogen for 16 hours. After the completion of the reaction, the reaction solution was poured into 1000 mL water, neutralized and adjusted with 2M of NaOH solution to the pH of 9, extracted with dichloromethane (500 mL) 5 times. The combined organic phases were dried over anhydrous sodium sulfate, and the solvent was removed by rotary evaporation under reduced pressure to obtain a crude product. The crude product was purified by column chromatography (petroleum ether/ethyl acetate=10/1 to ethyl acetate) to obtain Compound B5-1. LCMS (ESI) m/z: 210.8 [M+H]$^+$, $^1$H NMR (400 MHz, deuterated methanol) δ=6.51 (d, J=2.0 Hz, 1H), 6.22 (d, J=2.0 Hz, 1H), 3.77 (s, 3H), 3.70 (s, 3H).

Step 2: Synthesis of Compound B5-2

At room temperature, Compound B5-1 (5 g, 23.78 mmol, 1 eq) was added to a dioxane solution (50 mL), and at room temperature, isoamyl nitrite (4.18 g, 35.67 mmol, 4.80 mL, 1.5 eq) was added. The reaction solution was heated to 90° C. and stirred under the nitrogen protection for 1 hour. The reaction solution was cooled to room temperature and poured into 100 mL of water. The mixture was extracted with dichloromethane (20 mL) 5 times. The organic phases were combined. The combined organic phases were firstly washed with anhydrous sodium sulfate, and then the solvent was removed by rotary evaporation under reduced pressure to give the crude product. The crude product was purified by column chromatography (petroleum ether to petroleum ether/ethyl acetate=10/1) to obtain Compound B5-2. LCMS (ESI) m/z: 195.9 [M+H]$^+$, $^1$H NMR (400 MHz, deuterated methanol) δ=9.16 (s, 1H), 7.18 (d, J=1.6 Hz, 1H), 6.66 (d, J=2.0 Hz, 1H), 3.98 (s, 3H), 3.90 (s, 3H).

Step 3: Synthesis of Compound B5

In a 100 mL three-necked flask equipped with a stirrer and a low-temperature thermometer, B5-1 (1 g, 5.12 mmol, 1 eq) and tetrahydrofuran (20 mL) were added under the protection of nitrogen. Until the temperature of the system was reduced to −78° C., a solution of n-butyl lithium in n-hexane (2.5M, 2.46 mL, 1.2 eq) was slowly added dropwise, and the reaction system was maintained at −78° C. and stirred for 1 hour. Subsequently, tributyltin chloride (2.4 g, 7.37 mmol, 1.98 mL, 1.44 eq) was slowly added dropwise at −78° C. After the completion of the dropwise addition, the mixture was warmed up to −10° C. and reacted for 1 hour. Subsequently, tetrahydrofuran was removed from the reaction solution by rotary evaporation. 1,4-dioxane was added and dissolved. The insoluble matters were removed by filtration. The solvent was removed from the filtrate by rotary evaporation under reduced pressure to obtain Intermediate B5.

36

Intermediate B6

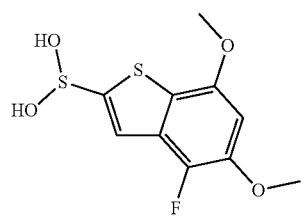

Synthesis Route

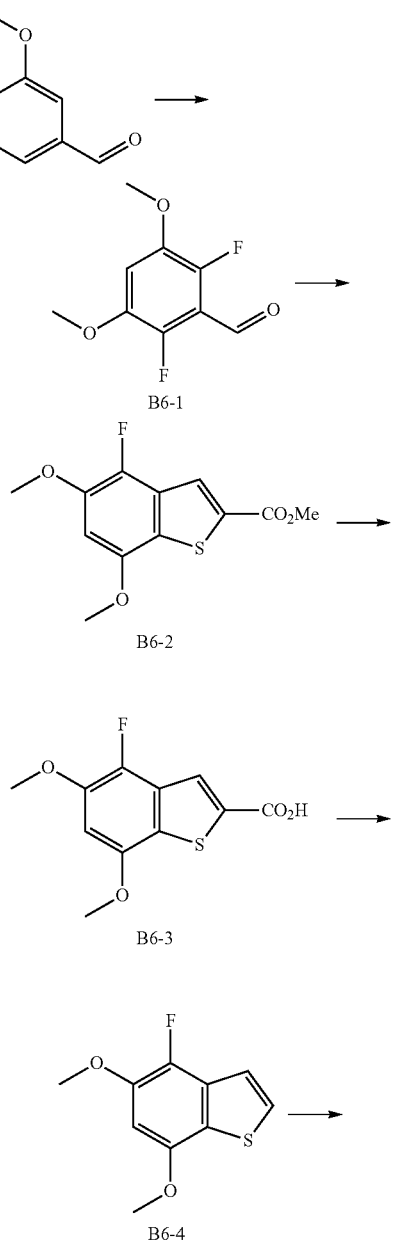

B6-1

B6-2

B6-3

B6-4

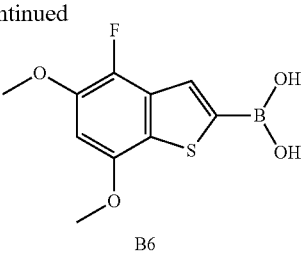

B6

Step 1: Synthesis of Compound B6-1

At 0° C., to a solution of 3,5-dimethoxybenzaldehyde (125 g, 752.23 mmol, 1 eq) in acetonitrile (3000 mL) was added in batch 1-chloromethyl-4-fluoro-1,4-diazabicyclo[2.2.2]octane bis(tetrafluoroborate) (532.97 g, 1.50 mol, 2 eq). After the completion of the addition, the reaction was slowly warmed to room temperature and stirred for 48 hours. After the completion of the reaction, the solid was removed from the reaction solution by filtration. Most of the solvent was removed from the filtrate by rotary evaporation under reduced pressure. The reaction solution was diluted with 1000 mL of ethyl acetate and adjusted with a saturated aqueous sodium bicarbonate solution to a pH of 7-8. Finally, the phases were separated with a separatory funnel, and the aqueous phase was extracted with ethyl acetate (1800 mL) 3 times. The organic phases were combined, washed once with 2000 mL of a saturated saline solution, dried over anhydrous sodium sulfate, and finally filtered. The solvent was removed from the filtrate by rotary evaporation under reduced pressure to obtain a crude product. The crude product was purified by column chromatography (100-200 mesh silica gel, eluent: petroleum ether/ethyl acetate=1/0-3/1) to obtain Compound B6-1.

Step 2: Synthesis of Compound B6-2

At 40° C., the reaction solution of B6-1 (10 g, 49.47 mmol, 1 eq), methyl mercaptoacetate (5.78 g, 54.41 mmol, 4.94 mL, 1.1 eq) and potassium carbonate (6.84 g, 49.47 mmol, 1 eq) in N,N-dimethyl formamide (100 mL) was stirred for 20 hours. After the completion of the reaction, the reaction solution was cooled to room temperature. 400 mL of water was added to the reaction solution. The mixture was extracted with 200 mL of ethyl acetate. The organic phase was dried over anhydrous sodium sulfate. After filtration, the solvent was removed from the filtrate by rotary evaporation under reduced pressure to obtain a crude product. The crude product was purified by a column machine (ISCO®; 200 g SepaFlash® silica gel fast column, mobile phase: 0-100% ethyl acetate/petroleum ether @ 100 mL/min) to obtain Compound B6-2.

Step 3: Synthesis of Compound B6-3

At 90° C., a mixed solution of B6-2 (5 g, 18.50 mmol, 1 eq) and lithium hydroxide monohydrate (7.76 g, 185.00 mmol, 10 eq) in dioxane (50 mL) and water (10 mL) was stirred for 18 hours. After the completion of the reaction, the reaction solution was cooled to room temperature, and then the organic solvent was removed by rotary evaporation under reduced pressure. 1M dilute hydrochloric acid was used to adjust the pH to 6, and the resulting mixture was extracted with 100 mL of ethyl acetate 5 times. The organic phases were combined, dried over anhydrous sodium sulfate, and filtered. The solvent was removed from the filtrate by rotary evaporation under reduced pressure to obtain Compound B6-3. $^1$H NMR (400 MHz, deuterated chloroform) δ=8.18 (s, 1H), 6.68 (d, J=6.0 Hz, 1H), 4.01 (s, 3H), 3.99 (s, 3H).

Step 4: Synthesis of Compound B6-4

At 200° C., a mixture of B6-3 (2.4 g, 9.37 mmol, 1 eq), cuprous oxide (2.68 g, 18.73 mmol, 1.91 mL, 2 eq) and quinoline (20 mL) was stirred for 1 hour. After the completion of the reaction, the reaction was cooled to room temperature. 50 mL of ethyl acetate was added to the reaction solution, and then 1M dilute hydrochloric acid was used to adjust the pH to 6. After the phase separation with a separatory funnel, the organic phase was dried over anhydrous sodium sulfate and filtered. The solvent was removed from the filtrate by rotary evaporation to obtain a crude product. The crude product was purified by a column machine (ISCO®; 24 g SepaFlash® silica gel fast column, mobile phase: 0-100% ethyl acetate/petroleum ether @ 35 mL/min) to obtain Compound B6-4. $^1$H NMR (400 MHz, deuterated chloroform) δ=7.47-7.41 (m, 1H), 7.41-7.35 (m, 1H), 6.57 (d, J=5.6 Hz, 1H), 3.99 (s, 3H), 3.98 (s, 3H).

Step 5: Synthesis of Compound B6

It was synthesized with reference to the synthesis method of Example 1, using Intermediate B6-4 as the starting material. $^1$H NMR (400 MHz, deuterated methanol) δ=7.80 (s, 1H), 6.74 (d, J=6.0 Hz, 1H), 3.97 (s, 3H), 3.95 (s, 3H).

Intermediate B7

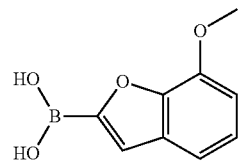

It was synthesized with reference to the synthesis method of Intermediate B1, using 7-methoxybenzofuran as the starting material. $^1$H NMR (400 MHz, deuterated methanol) δ=7.34 (s, 1H), 7.25-7.11 (m, 2H), 6.91 (d, J=7.6 Hz, 1H), 4.12-3.91 (m, 3H).

Intermediate B8

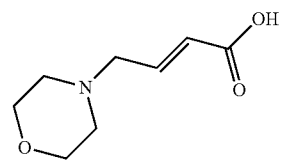 [SMILES: O=C(O)/C=C/CN1CCOCC1]

Synthesis Route

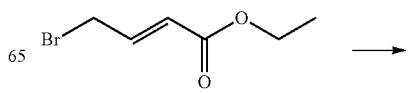

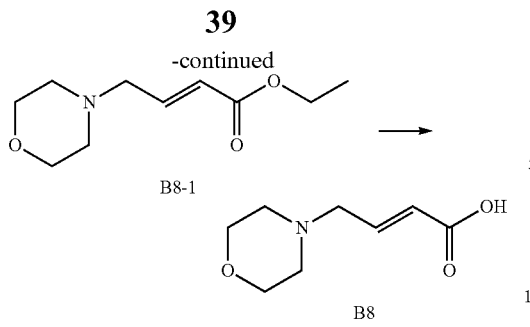

Step 1: Synthesis of Compound B8-1

At room temperature, tetrahydrofuran (100 mL) and ethyl 4-bromocrotonate (10.0 g, 51.80 mmol, 7.14 mL, 1.00 eq) were added in a pre-dried 250 mL flask, and the mixture was stirred at 25° C. $K_2CO_3$ (14.32 g, 103.61 mmol, 2.00 eq) and morpholine (4.74 g, 54.39 mmol, 4.79 mL, 1.05 eq) were added at 25° C., and the mixture was stirred at 25° C. for 12 hours. After the completion of the reaction, the reaction solution was slowly poured into water (50 mL). The mixture was extracted with ethyl acetate (50 ml) 3 times. The organic phases were combined, dried over anhydrous sodium sulfate, filtered, and concentrated to obtain a crude product. The crude product was purified by a column machine (petroleum ether/ethyl acetate=10:1-3:1) to obtain Compound B8-1. $^1$H NMR (400 MHz, deuterated chloroform) δ=7.27-6.88 (m, 1H), 6.00-5.95 (m, 1H), 4.15 (q, J=7.2 Hz, 2H), 3.75-3.59 (m, 4H), 3.12-3.10 (m, 2H), 2.51-2.31 (m, 4H), 1.35-1.09 (m, 3H).

Step 2: Synthesis of Compound B8

A clean 100 ml three-necked flask was prepared. Compound B8-1 (1 g, 5.02 mmol, 1 eq) was dissolved in methanol (20 ml) and water (10 mL) at 25° C., and then the stirring of the mixture was started. The reaction solution was cooled to 0° C. NaOH (602.27 mg, 15.06 mmol, 3 eq) was added to the above reaction solution. The reaction system was heated to 25° C. After stirring for 1 hour, the reaction solution was concentrated by rotary evaporation under reduced pressure. A solid precipitated. The solid was soaked with dichloromethane/methanol (10/1). The mixture was filtered. The filtrate was concentrated to obtain Compound B8. 1H NMR (400 MHz, deuterated methanol) δ=7.04-6.85 (m, 1H), 6.43-6.23 (m, 1H), 4.02-4.00 (m, 4H), 3.94-3.81 (m, 2H), 3.57-3.36 (m, 2H), 3.27-3.17 (m, 2H).

Intermediate B9

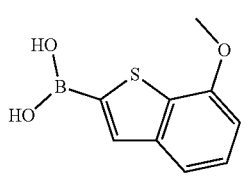

It was synthesized with reference to the synthesis method of Intermediate B1, using 7-methoxybenzothiophene as the starting material. $^1$H NMR (400 MHz, DMSO-$d_6$) δ=7.95-7.79 (m, 1H), 7.61-7.39 (m, 1H), 7.37-7.24 (m, 1H), 6.99-6.83 (m, 1H), 3.96-3.87 (m, 3H).

Examples 1 and 2: Synthesis of Compound WX001 (WX001A and WX001B)

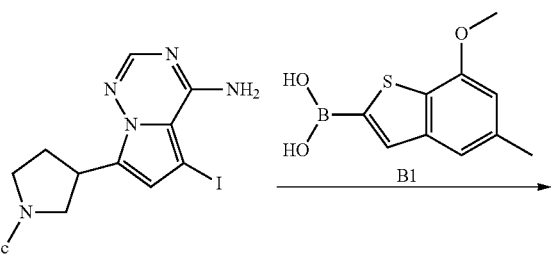

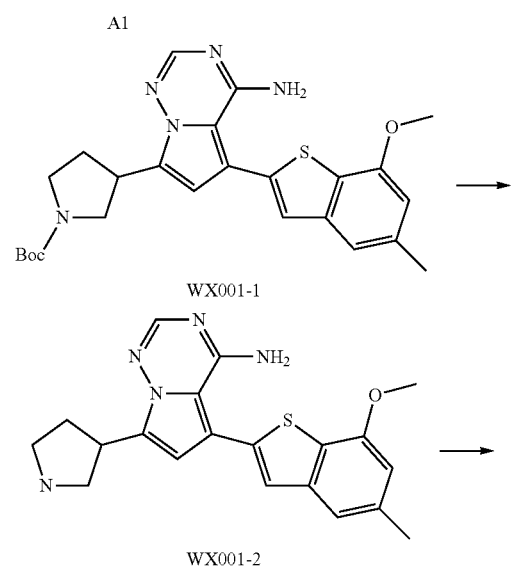

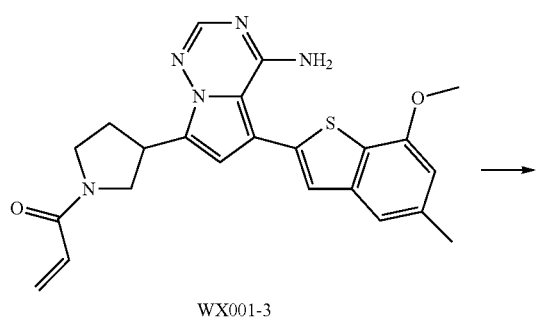

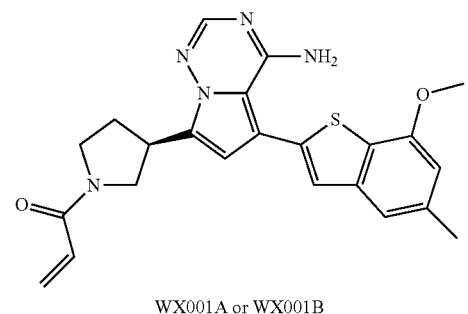

-continued

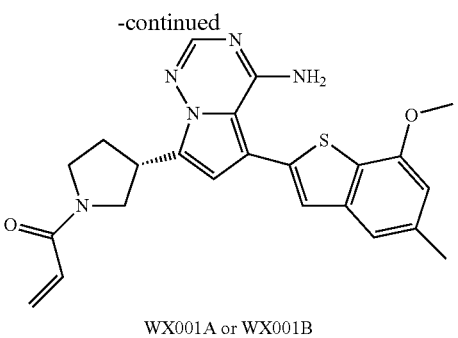

WX001A or WX001B

Step 1: Synthesis of Compound WX001-1

At room temperature, Compound B1 (777.25 mg, 3.50 mmol, 2.50 eq), sodium carbonate (296.77 mg, 2.80 mmol, 2.00 eq) and tetra(triphenylphosphine) palladium (161.78 mg, 140.00 μmol, 0.10 eq) were successively added to a mixed solution of Compound A1 (600.00 mg, 1.40 mmol, 1.00 eq) in ethylene glycol dimethyl ether (9 mL)/ethanol (3 mL)/water (0.5 mL). After being replaced with nitrogen 3 times, the mixture was heated to 90° C., stirred for 5 hours, cooled to room temperature, and poured into 30 mL of water. The resulting mixture was extracted with dichloromethane (10 mL) 5 times. The organic phases were combined, dried over anhydrous sodium sulfate, and filtered. The solvent was removed by rotary evaporation under reduced pressure to obtain a crude product. The crude product was purified by column chromatography (petroleum ether/ethyl acetate=10/1 to 1/3) to obtain WX001-1. LCMS (ESI) m/z: 480.2 [M+H]$^+$, 502.2 [M+Na]$^+$, $^1$H NMR (400 MHz, deuterated methanol) δ=7.91 (s, 1H), 7.27 (s, 2H), 6.77 (s, 1H), 6.70 (s, 1H), 4.00 (s, 3H), 3.96-3.90 (m, 2H), 3.64-3.50 (m, 3H), 2.49 (s, 3H), 2.44-2.36 (m, 2H), 1.50 (s, 9H).

Step 2: Synthesis of Compound WX001-2

At room temperature, a hydrochloric acid ethyl acetate solution (4M, 2.00 mL, 9.51 eq) was slowly added dropwise to a solution of WX001-1 (350.00 mg, 729.79 μmol, 1.00 eq) in ethyl acetate (2 mL). The mixture was stirred for 1 hour and filtered to obtain a solid. The solid was dried under reduced pressure to obtain the hydrochloride salt of Compound WX001-2. LCMS (ESI) m/z: 380.1 [M+H]$^+$, $^1$H NMR (400 MHz, deuterated methanol) δ=8.17 (s, 1H), 7.46 (s, 1H), 7.33 (s, 1H), 7.12-7.06 (m, 1H), 6.84 (s, 1H), 4.12-4.06 (m, 1H), 4.02 (s, 3H), 3.92-3.82 (m, 2H), 3.67-3.58 (m, 2H), 2.66-2.60 (m, 1H), 2.51 (s, 3H), 2.39-2.32 (m, 1H).

Step 3: Synthesis of Compound WX001 (WX001A and WX001B)

At 0° C., diisopropylethylamine (258.56 mg, 2.00 mmol, 349.41 μL, 4.00 eq) and a solution of acryloyl chloride in dichloromethane (0.25M, 1.80 mL, 0.90 eq) were added to a solution of the hydrochloride salt of WX001-2 (200.00 mg, 500.16 μmol, 1.00 eq) in dichloromethane (4.00 mL). The mixture was stirred for 5 minutes. The reaction solution was poured into 2 mL of water. After the phase separation, the aqueous phase was extracted with dichloromethane (1 mL) 3 times. The organic phases were combined. The combined organic phase was dried over anhydrous sodium sulfate and filtered. The solvent was removed from the filtrate by rotary evaporation under reduced pressure to obtain a crude product. The crude product was purified by a thin-layer preparative plate (dichloromethane/methanol=10/1) to obtain Compound WX001. Compound WX001 was chirally resolved (column: AS (250 mm*30 mm, 5 μm); mobile phase: [0.1% ammonia water ethanol]; B %: 40%-40%) to obtain WX001A (retention time: 6.16 minutes) and WX001B (retention time: 6.98 minutes). The retention time was measured with the following analytical column: Column: Chiralpak AS-3 150×4.6 mm I.D., 3 μm, mobile phase: A: carbon dioxide B: methanol (0.05% diethylamine), 40% B, flow rate: 2.5 mL/min, column temperature: 35° C. WX001A, LCMS (ESI) m/z: 434.2 [M+H]$^+$, 456.1[M+Na]$^+$, $^1$H NMR (400 MHz, deuterated methanol) δ=7.75 (d, J=2.8 Hz, 1H), 7.12-7.04 (m, 2H), 6.61 (s, 1H), 6.56-6.40 (m, 2H), 6.20-6.15 (m, 1H), 5.65-5.60 (m, 1H), 4.11-3.94 (m, 1H), 3.85 (s, 3H), 3.81-3.38 (m, 4H), 2.48-2.26 (m, 4H), 2.22-1.93 (m, 1H).

WX001B, LCMS (ESI) m/z: 434.2 [M+H]$^+$, 456.1[M+Na]$^+$, $^1$H NMR (400 MHz, deuterated methanol) $^1$H NMR (400 MHz, deuterated methanol) δ=7.75 (d, J=2.8 Hz, 1H), 7.08 (s, 2H), 6.61 (s, 1H), 6.54 (d, J=6.4 Hz, 1H), 6.41-6.51 (m, 1H), 6.20-6.16 (m, 1H), 5.66-5.42 (m, 1H), 4.09-3.96 (m, 1H), 3.85 (s, 3H), 3.80-3.38 (m, 4H), 2.44-2.25 (m, 4H), 2.21-1.99 (m, 1H).

Example 3: Synthesis of Compound WX001C

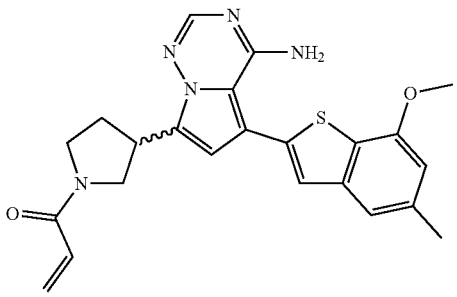 [SMILES: C=CC(=O)N1CCC(c2cc(-c3cc4cc(C)cc(OC)c4s3)c3c(N)ncnn23)C1]

It was synthesized with reference to the synthesis method of Example 1, using Intermediate A1-B and Intermediate B1 as the starting materials. It was combined with WX001A and identified with SFC (the SFC analysis method of Compound WX001, retention time: 6.14 minutes) as WX001A.

Example 4: Synthesis of Compound WX002A

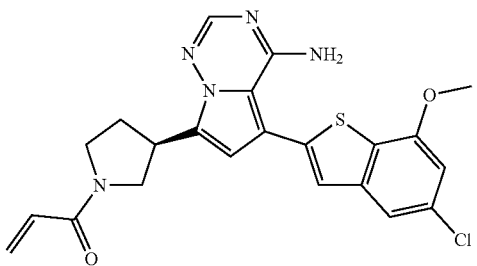 [SMILES: C=CC(=O)N1CC[C@@H](c2cc(-c3cc4cc(Cl)cc(OC)c4s3)c3c(N)ncnn23)C1]

It was synthesized with reference to the synthesis method of Example 1, using Intermediate A1-B and Intermediate B2 as the starting materials. LCMS (ESI) m/z: 454.1 [M+H]$^+$, $^1$H NMR (400 MHz, deuterated methanol) δ=7.81 (d, J=2.0 Hz, 1H), 7.36 (d, J=1.6 Hz, 1H), 7.21 (s, 1H), 6.82 (s, 1H), 6.64 (d, J=9.2 Hz, 1H), 6.58-6.50 (m, 1H), 6.22-6.17 (m, 1H), 5.68-5.63 (m, 1H), 4.20-3.93 (m, 2H), 3.91 (s, 3H), 3.77-3.44 (m, 3H), 2.52-2.31 (m, 1H), 2.27-2.05 (m, 1H).

Example 5: Synthesis of Compound WX002B

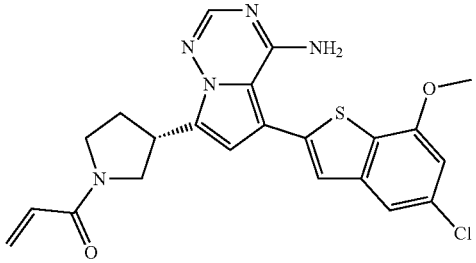 [SMILES: C=CC(=O)N1CC[C@H](c2cc(-c3cc4cc(Cl)cc(OC)c4s3)c3c(N)ncnn23)C1]

It was synthesized with reference to the synthesis method of Example 1, using Intermediate A1-A and Intermediate B2 as the starting materials. LCMS (ESI) m/z: 454.1 [M+H]$^+$, $^1$H NMR (400 MHz, deuterated methanol) δ=7.81 (d, J=2.4 Hz, 1H), 7.36 (d, J=1.6 Hz, 1H), 7.20 (s, 1H), 6.81 (s, 1H), 6.63 (d, J=8.8 Hz, 1H), 6.58-6.50 (m, 1H), 6.22-6.17 (m, 1H), 5.74-5.56 (m, 1H), 4.18-3.92 (m, 2H), 3.90 (s, 3H), 3.81-3.59 (m, 2H), 3.57-3.42 (m, 1H), 2.50-2.30 (m, 1H), 2.28-2.02 (m, 1H).

Example 6: Synthesis of Compound WX003

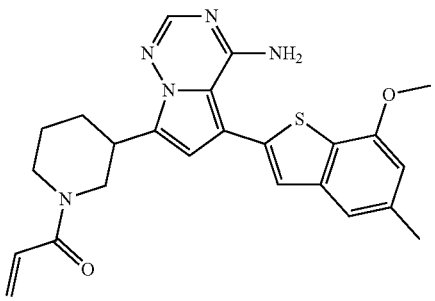 [SMILES: C=CC(=O)N1CCCC(c2cc(-c3cc4cc(C)cc(OC)c4s3)c3c(N)ncnn23)C1]

It was synthesized with reference to the synthesis method of Example 1, using Intermediate A3 and Intermediate B1 as the starting materials. LCMS (ESI) m/z: 448.1 [M+H]$^+$, 470.2 [M+Na]$^+$, $^1$H NMR (400 MHz, deuterated methanol) δ=7.83-7.76 (m, 1H), 7.15 (s, 2H), 6.75-6.68 (m, 1H), 6.66 (s, 1H), 6.61 (s, 1H), 6.14-6.06 (m, 1H), 5.68-5.58 (m, 1H), 4.42-4.27 (m, 1H), 3.88 (s, 3H), 3.40-3.27 (m, 2H), 3.08-2.83 (m, 2H), 2.37 (s, 3H), 2.13-2.02 (m, 1H), 1.86-1.72 (m, 2H), 1.63-1.54 (m, 1H).

Examples 7 and 8: Synthesis of Compound WX004 (WX004A, WX004B)

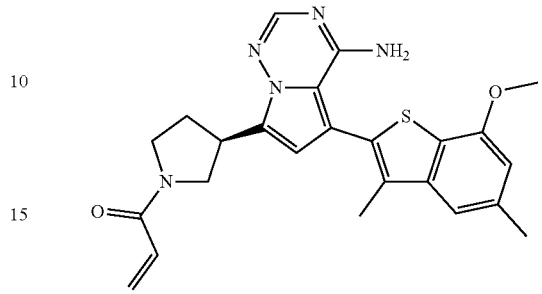
WX004A or WX004B

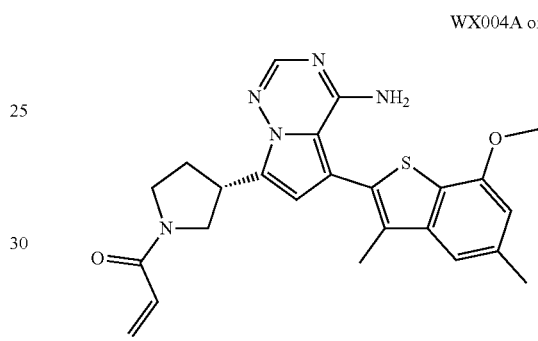
WX004A or WX004B

It was synthesized with reference to the method in step 1, Example 1, using Intermediate A2 and Intermediate B4 as the starting materials. After synthesis, the product was chirally resolved (column: AS (250 mm*30 mm, 10 m); mobile phase: [0.1% ammonia water/methanol]; B %: 40%-40%) to obtain Compounds WX004A (retention time: 5.58 minutes) and WX004B (retention time: 6.14 minutes). The retention time was measured with the following analytical column: Column: Chiralpak AS-3 150×4.6 mm I.D., 3 μm, mobile phase: A: carbon dioxide B: methanol (0.05% diethylamine), 40% B, flow rate: 2.5 mL/min, column temperature: 35° C.

WX004A, LCMS (ESI) m/z: 448.2 [M+H]$^+$, 470.2 [M+Na]$^+$, $^1$H NMR (400 MHz, deuterated methanol) δ=7.90 (d, J=2.0 Hz, 1H), 7.21 (s, 1H), 6.81 (s, 1H), 6.73-6.57 (m, 2H), 6.34-6.33 (m, 1H), 5.80-5.75 (m, 1H), 4.32-4.12 (m, 1H), 4.11-3.95 (m, 4H), 3.93-3.72 (m, 2H), 3.70-3.64 (m, 1H), 2.64-2.42 (m, 4H), 2.39-2.16 (m, 4H).

WX004B, LCMS (ESI) m/z: 448.2 [M+H]$^+$, $^1$H NMR (400 MHz, deuterated methanol) δ=7.78 (d, J=2.0 Hz, 1H), 7.09 (s, 1H), 6.69 (s, 1H), 6.63-6.44 (m, 2H), 6.22-6.17 (m, 1H), 5.73-5.54 (m, 1H), 4.24-4.01 (m, 1H), 4.00-3.89 (m, 1H), 3.87 (s, 3H), 3.80-3.60 (m, 2H), 3.57-3.44 (m, 1H), 2.52-2.32 (m, 4H), 2.30-2.10 (m, 4H).

Example 9: Synthesis of Compound WX005

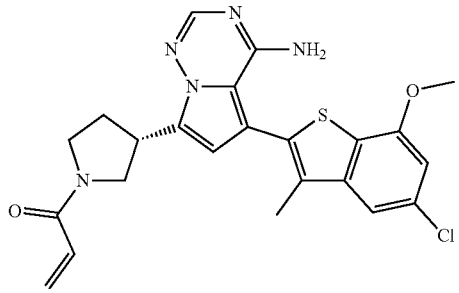 [SMILES: C=CC(=O)N1CC[C@H](c2cc(-c3sc4c(OC)cc(Cl)cc4c3C)c3c(N)ncnn23)C1]

It was synthesized with reference to the synthesis method of Example 1, using Intermediate A1-A and Intermediate B3 as the starting materials. LCMS (ESI) m/z: 490.1 [M+Na]$^+$, $^1$H NMR (400 MHz, deuterated methanol) δ=7.80 (d, J=2.0 Hz, 1H), 7.32 (d, J=1.2 Hz, 1H), 6.87 (s, 1H), 6.67-6.49 (m, 2H), 6.25-6.03 (m, 1H), 5.70-5.59 (m, 1H), 4.24-4.00 (m, 1H), 3.99-3.85 (m, 3H), 3.83-3.60 (m, 2H), 3.58-3.41 (m, 1H), 3.40-3.26 (m, 1H), 2.50-2.34 (m, 1H), 2.32-2.19 (m, 1H), 2.17 (s, 3H).

Example 10: Synthesis of Compound WX006A

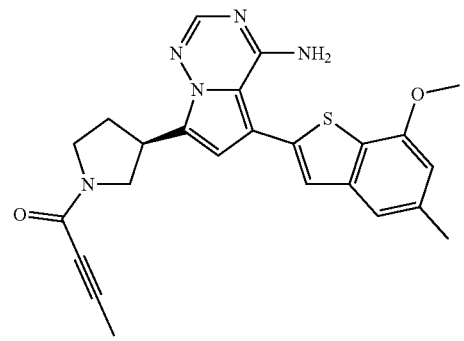 [SMILES: CC#CC(=O)N1CC[C@@H](c2cc(-c3cc4cc(C)cc(OC)c4s3)c3c(N)ncnn23)C1]

Synthesis Route

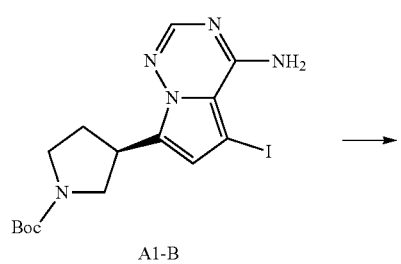

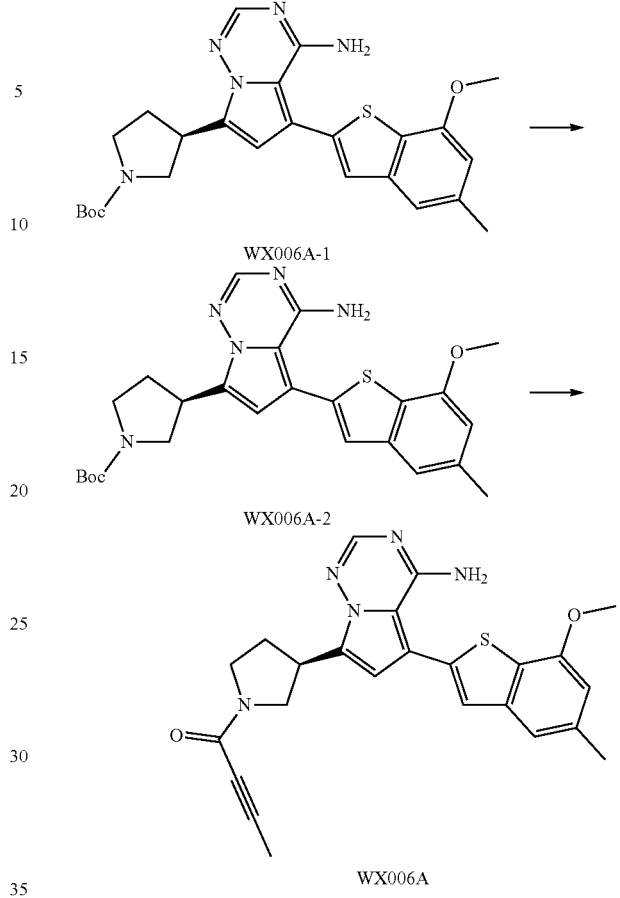

Step 1-2: Synthesis of Compound WX006A-2

It was synthesized with reference to the synthesis method in Step 1 and Step 2 of Example 1, using Intermediate A1-B and Intermediate B1 as the starting materials.

Step 3: Synthesis of Compound WX006A

At 0° C., O-(7-azabenzotriazol-1-yl)-N,N,N',N'-tetramethyluronium hexafluorophosphate (68.56 mg, 180.31 μmol, 1.50 eq) was added to a solution of 2-butynoic acid (10.11 mg, 120.21 μmol, 1.00 eq) in dichloromethane (2.00 mL). The mixture was stirred for 30 minutes. At 0° C., Compound WX006A-2 (50.00 mg, 120.21 μmol, 1.00 eq, HCl) and triethylamine (36.49 mg, 360.63 μmol, 49.994, 3.00 eq) were added to the reaction solution, and the resulting mixture was slowly warmed to 20° C. and stirred for 16 hours. After the completion of the reaction, the reaction solution was diluted with 10 mL of dichloromethane, washed with 15 mL of water 3 times, dried over anhydrous sodium sulfate, and filtered. The solvent was removed from the filtrate by rotary evaporation under reduced pressure to obtain a crude product. The crude product was isolated by a thin layer preparative plate (petroleum ether/ethyl acetate=1/1) to obtain Compound WX006A. LCMS (ESI) m/z: 446.1 [M+H]$^+$, 468.1 [M+Na]$^+$, $^1$H NMR (400 MHz, deuterated methanol) δ=7.78 (d, J=7.2 Hz, 1H), 7.13 (s, 2H), 6.64 (s, 1H), 6.59 (d, J=6.8 Hz, 1H), 3.98-3.74 (m, 5H), 3.69-3.55 (m, 2H), 3.47-3.34 (m, 1H), 2.46-2.31 (m, 4H), 2.22-2.07 (m, 1H), 1.93 (d, J=9.2 Hz, 3H).

Example 11: Synthesis of Compound WX006B

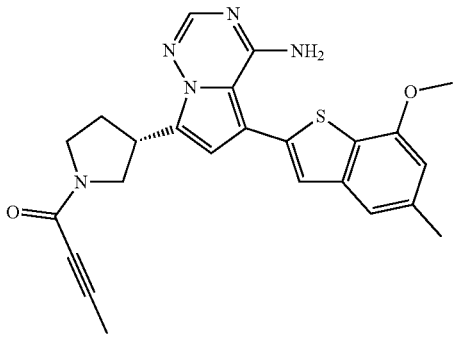 [SMILES: CC#CC(=O)N1CC[C@H](c2cc(-c3cc4cc(C)cc(OC)c4s3)c3c(N)ncnn23)C1]

It was synthesized with reference to the synthesis methods of Examples 1 and 9, using Intermediate A1-A and Intermediate B1 as the starting materials. LCMS (ESI) m/z: 446.1 [M+H]$^+$, 468.0 [M+Na]$^+$, $^1$H NMR (400 MHz, deuterated methanol) δ=7.78 (d, J=7.2 Hz, 1H), 7.13 (s, 2H), 6.64 (s, 1H), 6.59 (d, J=6.4 Hz, 1H), 4.00-3.73 (m, 5H), 3.70-3.51 (m, 2H), 3.45-3.34 (m, 1H), 2.36 (s, 4H), 2.23-2.06 (m, 1H), 1.93 (d, J=9.2 Hz, 3H).

Examples 12 and 13: Synthesis of Compound WX007 (WX007A, WX007B)

WX007A or WX007B

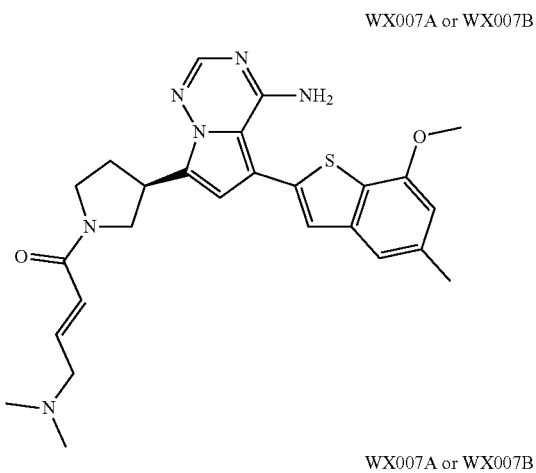

WX007A or WX007B

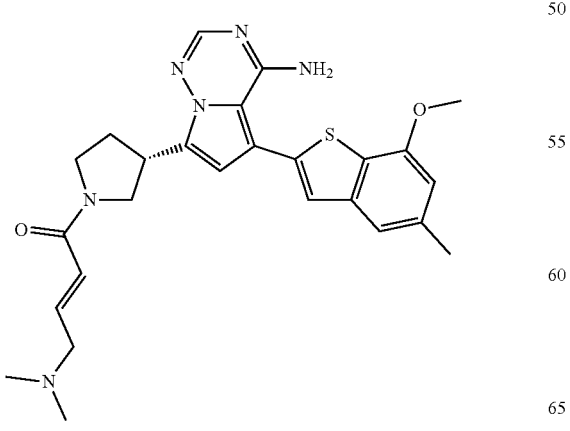

It was synthesized with reference to the method in step 3, Example 9, using Intermediate WX001-2 and oleic acid as the starting materials. After synthesis, the product was chirally resolved (column: AS (250 mm*30 mm, 10 μm); mobile phase: [0.1% ammonia water/ethanol]; B %: 45%-45%) to obtain Compounds WX007A (retention time: 1.70 minutes) and WX007B (retention time: 2.02 minutes). The retention time was measured with the following analytical column: Column: Chiralpak AS-H 150*4.6 mm I.D., 5 μm, mobile phase: 40% ethanol (0.05% diethylamine) in carbon dioxide, flow rate: 3 mL/min, column temperature: 40° C.

WX007A, LCMS (ESI) m/z: 491.2 [M+H]$^+$, 513.1 [M+Na]$^+$, $^1$H NMR (400 MHz, deuterated methanol) δ=7.76 (d, J=3.6 Hz, 1H), 7.09 (s, 2H), 6.79-6.67 (m, 1H), 6.62 (s, 1H), 6.55 (d, J=8.8 Hz, 1H), 6.37-6.32 (m, 1H), 4.12-3.92 (m, 1H), 3.86 (s, 3H), 3.81-3.72 (m, 1H), 3.70-3.39 (m, 3H), 3.07-2.99 (m, 2H), 2.39-2.25 (m, 4H), 2.16 (s, 3H), 2.15 (s, 3H), 2.12-1.99 (m, 1H).

WX007B, LCMS (ESI) m/z: 491.2 [M+H]$^+$, 513.1 [M+Na]$^+$, $^1$H NMR (400 MHz, deuterated methanol) δ=7.76 (d, J=3.2 Hz, 1H), 7.10 (s, 2H), 6.79-6.68 (m, 1H), 6.63 (s, 1H), 6.56 (d, J=9.2 Hz, 1H), 6.38-6.33 (m, 1H), 4.15-3.94 (m, 1H), 3.86 (s, 3H), 3.83-3.71 (m, 1H), 3.69-3.40 (m, 3H), 3.06-3.03 (m, 2H), 2.40-2.32 (m, 4H), 2.17 (s, 3H), 2.15 (s, 3H), 2.12-1.97 (m, 1H).

Example 14: Synthesis of Compound WX008

WX008

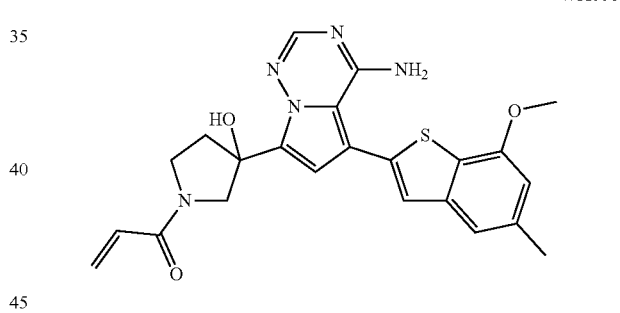

Synthesis Route

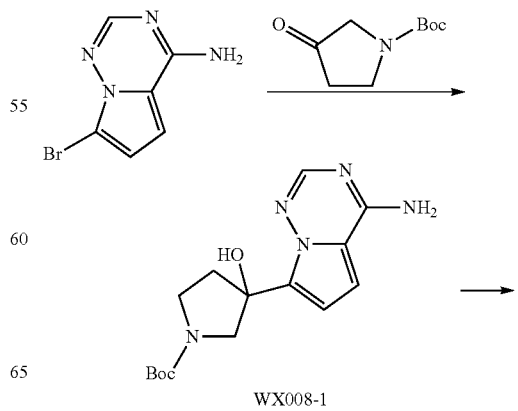

WX008-1

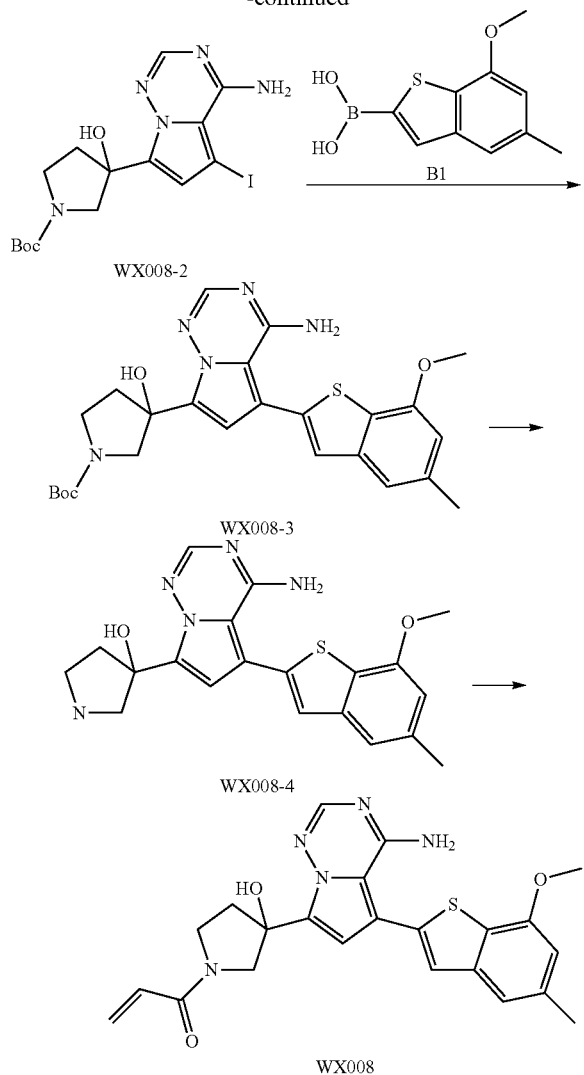

Step 2: Synthesis of WX008-2

It was synthesized with reference to the synthesis method of A1, using Intermediate WX008-1 as the starting material. LCMS (ESI) m/z: 446.0 [M+H]+.

Step 3-5: Synthesis of WX008

It was synthesized with reference to the synthesis method of Example 1, using Intermediate WX008-2 as the starting material. LCMS (ESI) m/z: 432.1 [M+H]+, 450.1 [M+Na]+, $^1$H NMR (400 MHz, deuterated methanol) δ=7.81 (d, J=3.6 Hz, 1H), 7.15 (d, J=2.4 Hz, 2H), 6.77 (d, J=3.6 Hz, 1H), 6.65 (s, 1H), 6.63-6.44 (m, 1H), 6.24-6.19 (m, 1H), 5.72-5.57 (m, 1H), 4.17-3.93 (m, 2H), 3.88 (s, 3H), 3.85-3.56 (m, 2H), 2.86-2.61 (m, 1H), 2.37 (s, 3H), 2.34-2.20 (m, 1H).

Examples 15 and 16: Synthesis of Compounds WX009A and WX009B

WX009A or WX009B

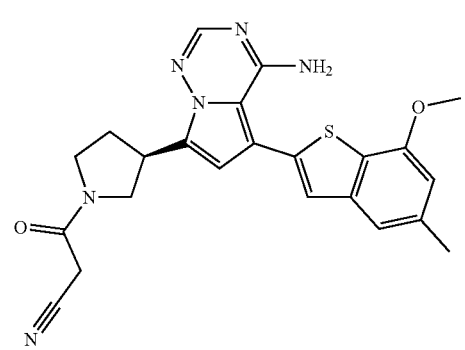

WX009A or WX009B

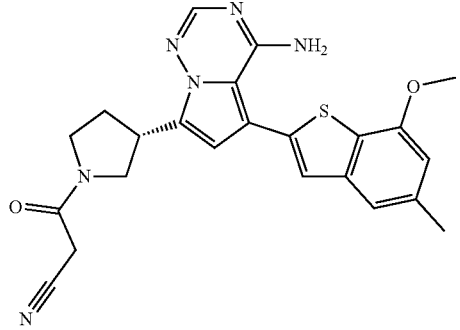

Compound WX009 was synthesized with reference to the synthesis methods of Examples 1 and 9, using Intermediate A1, Intermediate B1 and cyanoacetic acid as the starting materials. The separation through SFC (column: AD (250 mm*30 mm, 10 m); mobile phase: [0.1% ammonia water isopropanol]; B %: 55%-55%) obtained Compound WX009A (retention time: 5.08 minutes) and Compound WX009B (retention time: 7.89 minutes). The retention time was measured with the following analytical column: Column: Chiralpak AD-3 50*4.6 mm I.D., 3 µm, mobile phase: 40% isopropanol (0.05% ethylene diamine) in carbon dioxide, flow rate: 4 mL/min, column temperature: 40° C.

WX009A: LCMS (ESI) m/z: 447.2[M+H]+, 469.1[M+Na]+, $^1$H NMR (400 MHz, deuterated methanol) δ=7.79 (d, J=1.2 Hz, 1H), 7.16 (d, J=1.6 Hz, 2H), 6.75-6.54 (m, 2H),

Step 1: Synthesis of Compound WX008-1

At −60° C., under the nitrogen protection, methyl lithium (1.6M, 616.104, 1.05 eq) was added dropwise to a solution of 4-amino-7-bromo-pyrrolo[2,1-f][1,2,4]triazine (0.2 g, 938.81 µmol, 1 eq) in tetrahydrofuran (15 mL) solution within 15 minutes. 30 minutes after the reaction, n-butyl lithium (2.5M, 413.084, 1.1 eq) was slowly added dropwise to the reaction solution. The reaction solution was stirred for 1 hour between −60° C. and −40° C., and then N—BOC-3-pyrrolidone (347.77 mg, 1.88 mmol, 2 eq) was added to the reaction solution. The reaction solution was slowly warmed to 20° C. and stirred for 16 hours. The reaction solution was cooled to 0° C., and 1 mL of water was added to the reaction solution to quench the reaction. The reaction solution was diluted with 5 mL of water and extracted with ethyl acetate (5 mL) 3 times. The organic phases were washed with 10 mL of a saturated saline solution, dried over anhydrous sodium sulfate, and filtered. The filtrate was rotary evaporated under reduced pressure to obtain Compound WX008-1 as a crude product. The crude product was used directly in the next reaction. LCMS (ESI) m/z: 319.9 [M+H]+.

4.05-3.93 (m, 2H), 3.88 (s, 3H), 3.70-3.59 (m, 1H), 3.56-3.39 (m, 2H), 2.48-2.33 (m, 4H), 2.25-2.01 (m, 1H).

WX009B: LCMS (ESI) m/z: 447.2 [M+H]⁺, 469.4[M+Na]⁺, ¹H NMR (400 MHz, deuterated methanol) δ=7.79 (d, J=1.6 Hz, 1H), 7.16 (d, J=1.6 Hz, 2H), 6.74-6.51 (m, 2H), 4.10-3.91 (m, 2H), 3.88 (s, 3H), 3.71-3.59 (m, 1H), 3.58-3.40 (m, 2H), 2.50-2.27 (m, 4H), 2.26-1.99 (m, 1H).

Example 17: Synthesis of Compound WX010

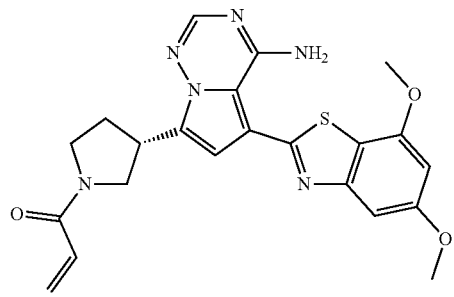

WX010

Synthesis Route

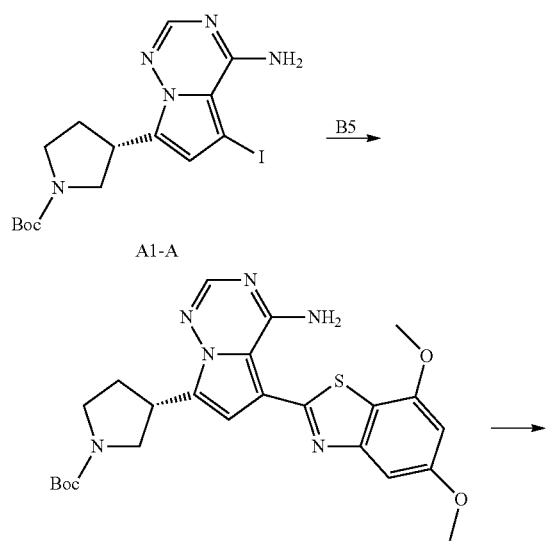

A1-A

WX010-1

WX010-2

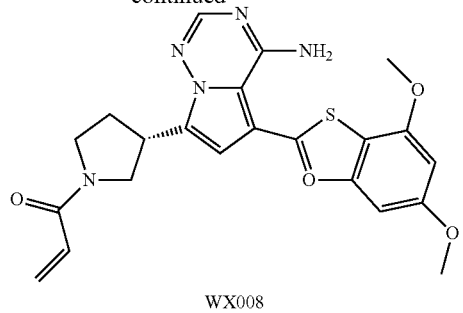

WX008

Step 1: Synthesis of Compound WX010-1

In a 100 mL three-necked flask equipped with a stirrer, under the protection of nitrogen, Compound A1 (1.10 g, 2.56 mmol, 1 eq), cuprous iodide (97.53 mg, 512.00 µmol, 0.2 eq), bis(triphenylphosphine)palladium dichloride (359.44 mg, 512.00 µmol, 0.2 eq), triethylamine (1.04 g, 10.24 mmol, 1.43 mL, 4 eq) and 1,4-dioxane (5 mL) were successively added, and then the freshly prepared Compound B5 (2.48 g, 5.12 mmol, 2 eq) was added. After being replaced with nitrogen 3 times, the reaction solution was placed in a 100° C. oil bath and reacted for 12 hours. After the completion of the reaction, the insoluble matters were removed by filtration, and the filtrate was rotary evaporated under reduced pressure to obtain a crude product. The crude product was subjected to column chromatography (petroleum ether/ethyl acetate=3/1 to ethyl acetate) to obtain the product WX010-1. LCMS (ESI) m/z: 467.1 [M+H]⁺.

Steps 2 and 3: Synthesis of Compound WX010

Compound WX010 was synthesized with reference to the method in steps 2 and 3, Example 1, using Intermediate WX010-1 as the starting material. LCMS (ESI) m/z: 473.1 [M+Na]⁺, ¹H NMR (400 MHz, deuterated methanol) δ=7.86 (s, 1H), 7.09-6.93 (m, 2H), 6.70-6.64 (m, 1H), 6.55 (s, 1H), 6.37-6.31 (m, 1H), 5.82-5.79 (m, 1H), 4.34-4.09 (m, 1H), 3.97 (s, 3H), 3.89-3.83 (m, 5H), 3.82-3.69 (m, 1H), 3.68-3.55 (m, 1H), 2.62-2.41 (m, 1H), 2.38-2.12 (m, 1H).

Examples 18 and 19: Synthesis of WX011 (WX011A and WX011B)

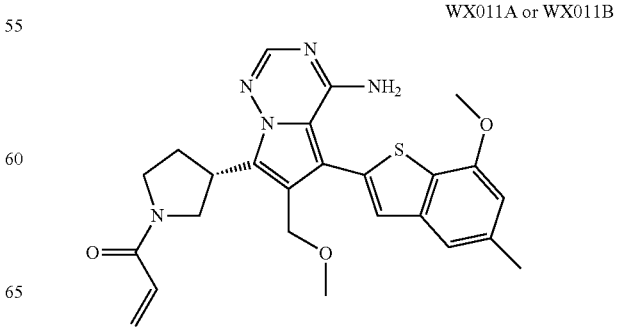

WX011A or WX011B

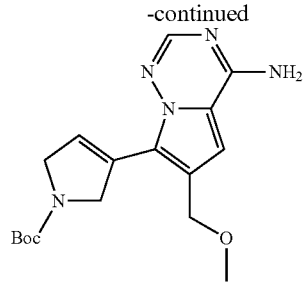
WX011A or WX011B
Synthesis Route
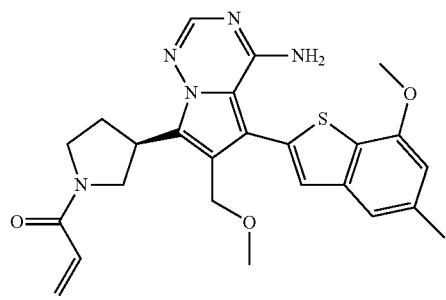
WX011-1
WX011-2
WX011-3
WX011-4
WX011-5
WX011-6
WX011-7
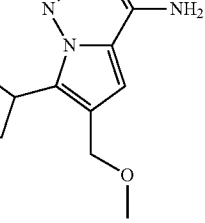
WX011-8
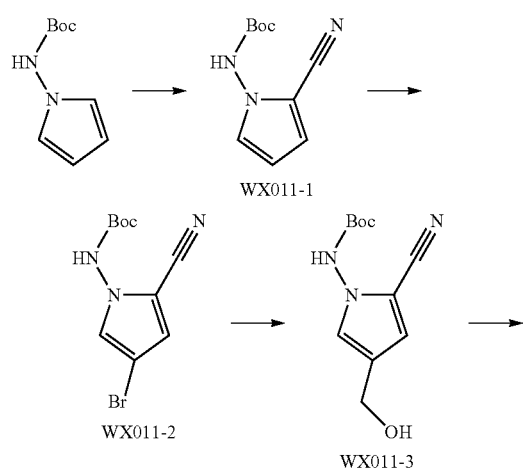
WX011-9
WX011-10

-continued

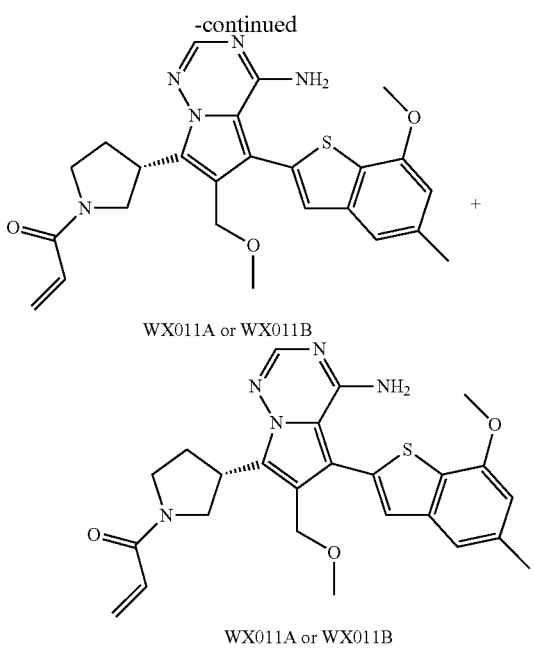

WX011A or WX011B

WX011A or WX011B

Step 1: Synthesis of Compound WX011-1

A solution of tert-butyl (1H-pyrrol-1-yl)carbamate (25.00 g, 137.20 mmol, 1.00 eq) in acetonitrile (200.00 mL) was cooled to 0° C., and chlorosulphonylisocyanate (20.39 g, 144.06 mmol, 12.51 mL, 1.05 eq) was slowly added dropwise with a syringe to the reaction solution. A precipitate formed after stirring for 30 minutes. After continuing to stir for 45 minutes at 0° C., N,N-dimethyl formamide (14.84 g, 203.05 mmol, 15.62 mL, 2.50 eq) was added dropwise with a syringe to the reaction solution, and the precipitate in the reaction solution disappeared. After continuing to stir at this temperature for 45 minutes, the reaction solution was slowly warmed to 25° C., and the reaction was completed. The reaction solution was slowly poured into 200 mL of ice water. The mixture was extracted with 200 mL of ethyl acetate. The organic phase was firstly dried over anhydrous magnesium sulfate and then filtered with a sand-core funnel filled with silica gel. The solvent was removed from the filtrate by rotary evaporation under reduced pressure to obtain Compound WX011-1.

Step 2: Synthesis of Compound WX011-2

At −30° C., dibromohydantoin (10.69 g, 37.40 mmol, 0.50 eq) was added in batch to a solution of WX011-1 (15.50 g, 74.80 mmol, 1.00 eq) in acetonitrile (150 mL). The reaction solution was slowly warmed to 25° C. and stirred for 2 hours. After the completion of the reaction, the reaction solution was added to 100 mL of water, and the aqueous phase was extracted with ethyl acetate (100 mL×3). The organic phases were combined. The combined organic phase was washed once with 100 mL of a saturated saline solution, dried over anhydrous sodium sulfate, and filtered. The filtrate was rotary-evaporated under reduced pressure to obtain a crude product. The crude product was purified by column chromatography (petroleum ether/ethyl acetate=9/1-1/1) to obtain Compound WX011-2. 1H NMR (400 MHz, CDCl$_3$) δ=7.23 (brs, 1H), 6.85 (d, J=2.0 Hz, 1H), 6.71 (d, J=2.0 Hz, 1H), 1.44 (s, 9H).

Step 3: Synthesis of Compound WX011-3

Under a nitrogen atmosphere, a solution of WX011-2 (5.30 g, 18.52 mmol, 1.0 eq) in tetrahydrofuran (100 mL) was cooled to −60° C. Methyl magnesium bromide (3 mol/L tetrahydrofuran solution, 6.80 mL, 20.38 mmol, 1.1 eq) was slowly added dropwise to the reaction solution, and the resulting mixture was stirred for 30 minutes. Then n-butyl lithium (2.0 mol/L n-hexane solution, 14.80 mL, 37.05 mmol, 2.0 eq) was added dropwise to the reaction solution. The reaction solution was kept at an internal temperature between −40° C. and −60° C. and stirred for 1 hour. Paraformaldehyde (1.67 g, 18.52 mmol, 1.0 eq) was added to the reaction solution. Then the resulting mixture was warmed to room temperature and stirred overnight. After the completion of the reaction, the reaction solution was slowly poured into 100 mL of a saturated saline solution. The resulting mixture was extracted with ethyl acetate (100 mL×3). The organic phases were combined. The combined organic phase was washed once with 100 mL of a saturated saline solution, dried over anhydrous sodium sulfate, and filtered. Then the filtrate was rotary-evaporated under reduced pressure to obtain a crude product. The crude product was purified by a column machine (ISCO®; 220 g SepaFlash® Silica Flash Column, mobile phase 0-50% ethyl acetate/petroleum ether @ 100 mL/min) to obtain Compound WX011-3. $^1$H NMR (400 MHz, DMSO-d6): δ=10.77 (brs, 1H), 7.09 (d, J=1.6 Hz, 1H), 6.86 (d, J=1.6 Hz, 1H), 4.97 (t, J=5.6 Hz, 1H), 4.28 (d, J=5.6 Hz, 2H), 1.45 (s, 9H).

Step 4: Synthesis of Compound WX011-4

At room temperature, a hydrogen chloride/dioxane solution (12 mL) was added to Compound WX011-3 (4.70 g, 19.81 mmol, 1 eq). The mixture was stirred for 5 hours, and then methanol (60 mL) was added to the reaction solution. The resulting mixture was stirred overnight. Finally, potassium phosphate (42.05 g, 198.10 mmol, 10 eq) and formamidine acetate (10.31 g, 99.05 mmol, 5 eq) were added to the reaction solution, and then the resulting mixture was warmed to 65° C. and stirred for 20 hours. After the completion of the reaction, the reaction solution was cooled to room temperature and filtered. The filtrate was concentrated and purified by a column machine (ISCO®; 220 g SepaFlash® Silica Flash Column, mobile phase 0-3% methanol/dichloromethane @ 100 mL/min) to obtain Compound WX011-4. LCMS (ESI) m/z: 178.9 [M+H]$^+$, $^1$H NMR (400 MHz, DMSO-d6) δ=7.78 (s, 1H), 7.69 (brs, 2H), 7.58 (d, J=1.2 Hz, 1H), 6.82 (d, J=1.6 Hz, 1H), 4.42 (s, 2H), 3.26 (s, 3H).

Step 5: Synthesis of Compound WX011-5

At −30° C., dibromohydantoin (1.85 g, 6.46 mmol, 0.50 eq) was added in batch to a solution of WX011-4 (2.30 g, 12.91 mmol, 1.00 eq) in tetrahydrofuran (20 mL). The reaction solution was stirred at 15° C. for 16 hours. Then the reaction solution was concentrated and purified by a column machine (ISCO®; 40 g SepaFlash® Silica Flash Column, mobile phase 0-10% dichloromethane/methanol @ 60 mL/min) to obtain WX011-5 as a white solid. LCMS (ESI) m/z: 256.8 [M+H]$^+$, 1H NMR (400 MHz, DMSO-d6) δ=7.92 (s, 1H), 7.88 (brs, 1H), 7.04 (s, 1H), 4.42 (s, 2H), 3.27 (s, 3H).

Step 6: Synthesis of Compound WX011-6

At room temperature, WX011-5 (6.40 g, 24.89 mmol, 1.00 eq) was dissolved in a mixed solution of 1,4-dioxane (100 mL) and water (20 mL). Then N-Boc-2,5-dihydro-1H-pyrrole-1-pinacol borate (7.35 g, 24.89 mmol, 1.00 eq), potassium phosphate (15.85 g, 74.68 mmol, 3.00 eq) and 1,1'-bis(diphenylphosphine) ferrocene palladium chloride (1.82 g, 2.49 mmol, 0.10 eq) were successively added to the mixed solution. Under the nitrogen protection, the reaction solution was heated to 80° C. and stirred for 16 hours. After the completion of the reaction, the reaction solution was cooled to room temperature and slowly poured into 100 mL of water. The mixture was extracted with ethyl acetate (100 mL×3). The organic phases were combined, and the combined organic phase was dried over anhydrous sodium sulfate, and filtered. The filtrate was rotary-evaporated under reduced pressure to obtain Compound WX011-6. LCMS (ESI) m/z: 346.0 $[M+H]^+$.

Step 7: Synthesis of Compound WX011-7

At room temperature, palladium hydroxide (65.05 mg, 463.24 μmol, 0.1 eq) was added to a solution of WX011-6 (1.60 g, 4.63 mmol, 1.00 eq) in methanol (30 mL). After being replaced with hydrogen 3 times, the reaction solution was heated to 50° C. and stirred for 16 hours under 50 psi hydrogen. The reaction solution was cooled to room temperature and filtered to remove the catalyst. The solvent was removed from the filtrate by rotary evaporation under reduced pressure to obtain WX011-7. LCMS (ESI) m/z: 348.1 $[M+H]^+$.

Step 8: Synthesis of Compound WX011-8

At room temperature, bromosuccinimide (563.55 mg, 3.17 mmol, 1.10 eq) was added in batch to a solution of WX011-7 (1.00 g, 2.88 mmol, 1.00 eq) in tetrahydrofuran (20 mL). After the reaction solution was stirred at 20° C. for 1 hour, the reaction solution was added to ethyl acetate (50 mL). The resulting mixture was successively washed once with 30 mL of water and 30 mL of a saturated saline solution, dried over anhydrous sodium sulfate, and rotary-evaporated under reduced pressure to obtain Compound WX011-8. LCMS (ESI) m/z: 425.9 $[M+H]^+$.

Step 9: Synthesis of Compound WX011-9

At room temperature, Compound WX011-8 (1.25 g, 5.63 mmol, 1.50 eq), cesium fluoride (2.85 g, 18.77 mmol, 5.00 eq) and chloro(2-dicyclohexylphosphino-2,4,6-triisopropyl-1,1-biphenyl) [2-(2-amino-1,1-biphenyl)] palladium (II) (295.3 mg, 375.32 μmol, 0.10 eq) was successively added to a mixed solution of Compound WX001-9 (1.60 mg, 3.75 mmol, 1.00 eq) in tetrahydrofuran (20 mL)/water (2 mL). After being replaced with nitrogen 3 times, the mixture was heated to 60° C., stirred for 16 hours, cooled to room temperature, and poured into 30 mL of water. The resulting mixture was extracted with dichloromethane (10 mL) 3 times, and the organic phases were combined. The combined organic phase was washed once with 10 mL of a saturated saline solution, dried over anhydrous sodium sulfate and filtered. The solvent was removed from the filtrate by rotary evaporation under reduced pressure to obtain Compound WX011-9. LCMS (ESI) m/z: 524.1 $[M+H]^+$.

Step 10: Synthesis of Compound WX011-10

At room temperature, a solution of hydrochloric acid in ethyl acetate (4M, 20.00 mL) was added to WX011-9 (1.60 g, 3.06 mmol, 1.00 eq). The mixture was stirred for 1 hour and filtered to obtain a solid. The solid was dried under reduced pressure to obtain a hydrochloride salt of Compound WX011-10. LCMS (ESI) m/z: 424.1 $[M+H]^+$.

Step 11: Synthesis of Compound WX011

At 0° C., acryloyl chloride (216.44 mg, 2.39 mmol, 1.00 eq) was added to a solution of triethylamine (2.42 g, 23.91 mmol, 10.00 eq) and WX011-10 hydrochloride (1.10 g, 2.39 mmol, 1.00 eq) in dichloromethane (10 mL). The mixture was stirred for 60 minutes, and the reaction solution was poured into 25 mL of dichloromethane. The organic phases were washed twice with water (25 mL). The combined organic phase was dried over anhydrous sodium sulfate and filtered. The solvent was removed from the filtrate by rotary evaporation under reduced pressure to obtain a crude product. The crude product was purified with a thin layer preparative plate (ethyl acetate) to obtain Compound WX011. Compound WX011 was chirally resolved (column: AD (250 mm*30 mm, 5 μm); mobile phase: [0.1% ammonia water ethanol]; B %: 45%-45%) to obtain WX011A (retention time: 0.58 minutes) and WX011B (retention time: 0.74 minutes).

The retention time was measured with the following analytical column: column: Chiralpak AD-3 50*4.6 mm I.D., 3 μm, mobile phase: 40% isopropanol (0.05% ethylenediamine) in carbon dioxide, flow rate: 4 mL/min, column temperature: 40° C.

WX011A, LCMS (ESI) m/z: 478.1 $[M+H]^+$, 500.1 $[M+Na]^+$, $^1$H NMR (400 MHz, CDCl$_3$) δ: 7.85 (d, J=8.4 Hz, 1H), 7.20 (s, 1H), 7.16 (s, 1H), 6.62 (s, 1H), 6.51-6.30 (m, 2H), 5.68-5.60 (m, 1H), 5.47 (2H, brs), 4.34 (s, 2H), 4.18-3.78 (m, 7H), 3.65-3.48 (m, 1H), 3.22 (d, J=10.0 Hz, 3H), 2.85-2.65 (m, 1H), 2.44 (s, 3H).

WX011B, LCMS (ESI) m/z: 478.1 $[M+H]^+$, 500.0 $[M+Na]^+$, $^1$H NMR (400 MHz, CDCl$_3$) δ: 7.84 (d, J=8.8 Hz, 1H), 7.20 (s, 1H), 7.16 (s, 1H), 6.62 (s, 1H), 6.51-6.30 (m, 2H), 5.68-5.60 (m, 1H), 5.42 (2H, brs), 4.34 (s, 2H), 4.15-3.72 (m, 7H), 3.62-3.48 (m, 1H), 3.22 (d, J=10.4 Hz, 3H), 2.90-2.65 (m, 1H), 2.44 (s, 3H).

Example 20: Synthesis of Compound WX012

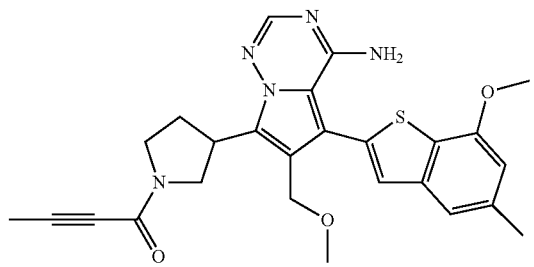 [SMILES: CC#CC(=O)N1CCC(c2c(COC)c(-c3cc4cc(C)cc(OC)c4s3)c3c(N)ncnn23)C1]

Synthesis Route

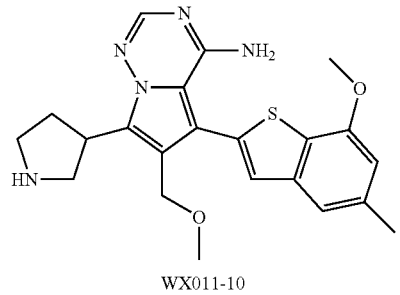

WX011-10

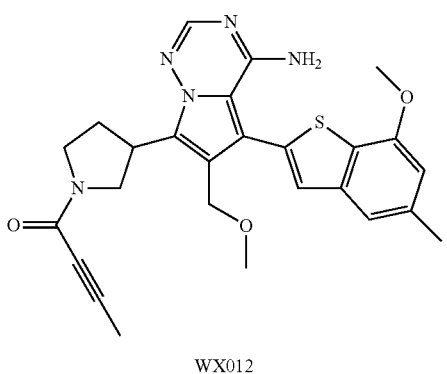

WX012

It was synthesized with reference to the synthesis method of Example 9, using Intermediate WX011-10 as intermediate. LCMS (ESI) m/z: 490.0 [M+H]⁺, 512.0 [M+Na]⁺, ¹H NMR (400 MHz, CDCl₃) δ=7.90-7.80 (m, 1H), 7.22-7.18 (m, 1H), 7.16 (s, 1H), 6.65-6.60 (m, 1H), 6.57 (brs, 2H), 4.38-4.30 (m, 2H), 4.20-3.90 (m, 6H), 3.89-3.70 (m, 1H), 3.68-3.38 (m, 1H), 3.28-3.18 (m, 3H), 2.80-2.65 (m, 1H), 2.44 (s, 3H), 2.18-2.08 (m, 1H), 1.98-1.85 (m, 3H).

Example 21: Synthesis of Compound WX013

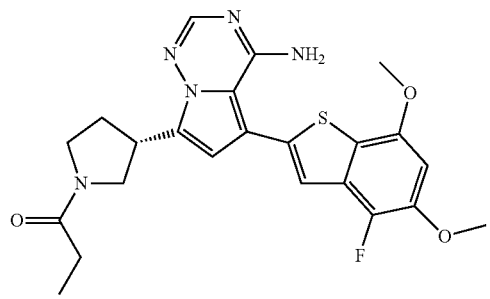 [SMILES: CCC(=O)N1CC[C@H](c2cc(-c3cc4c(F)c(OC)cc(OC)c4s3)c3c(N)ncnn23)C1]

It was synthesized with reference to the synthesis method of WX001, using Intermediate A1-A and Intermediate B6 as the starting materials. LCMS (ESI) m/z: 470.1 [M+H]⁺, ¹H NMR (400 MHz, deuterated methanol) δ=7.79 (d, J=3.2 Hz, 1H), 7.20 (s, 1H), 6.72-6.54 (m, 2H), 4.09-3.91 (m, 1H), 3.88 (s, 3H), 3.87 (s, 3H), 3.85-3.72 (m, 1H), 3.67-3.37 (m, 4H), 2.32-2.25 (m, 2H), 1.05-1.00 (m, 3H).

Example 22: Synthesis of Compound WX014

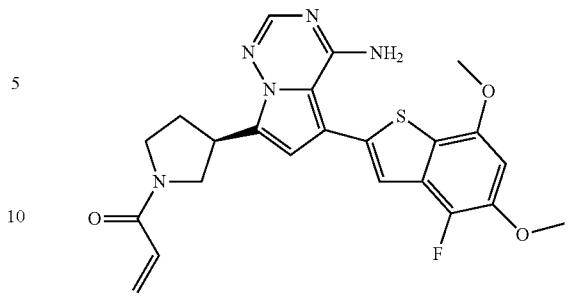

It was synthesized with reference to the synthesis method of WX001, using Intermediate A1-B and Intermediate B6 as the starting materials. LCMS (ESI) m/z: 468.1 [M+H]⁺, ¹H NMR (400 MHz, deuterated methanol) δ=7.90 (br s, 1H), 7.31 (br d, J=10.0 Hz, 1H), 6.83-6.69 (m, 2H), 6.69-6.55 (m, 1H), 6.39-6.21 (m, 1H), 5.83-5.70 (m, 1H), 4.69 (br d, J=2.0 Hz, 1H), 4.28-4.04 (m, 1H), 3.99 (d, J=3.6 Hz, 3H), 3.97 (d, J=2.4 Hz, 4H), 3.89-3.70 (m, 2H), 3.64-3.54 (m, 1H), 2.63-2.42 (m, 1H), 2.33-2.13 (m, 2H).

Example 23: Synthesis of Compound WX015

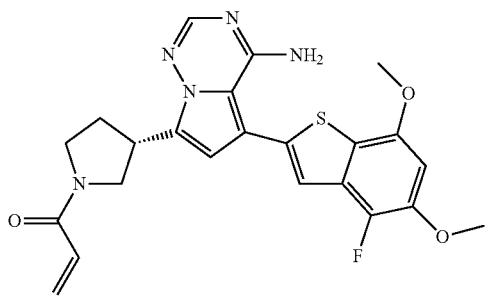 [SMILES: C=CC(=O)N1CC[C@H](c2cc(-c3cc4c(F)c(OC)cc(OC)c4s3)c3c(N)ncnn23)C1]

It was synthesized with reference to the synthesis method of WX001, using Intermediate A1-A and Intermediate B6 as the starting materials. LCMS (ESI) m/z: 468.1 [M+H]⁺, ¹H NMR (400 MHz, deuterated methanol) δ=7.79 (d, J=1.6 Hz, 1H), 7.18 (d, J=1.6 Hz, 1H), 6.65-6.60 (m, 2H), 6.56-6.47 (m, 1H), 6.28-6.03 (m, 1H), 5.74-5.57 (m, 1H), 4.17-3.97 (m, 1H), 3.88 (s, 3H), 3.86 (s, 3H), 3.77-3.59 (m, 2H), 3.50-3.38 (m, 1H), 23.07-2.96 (m, 1H), 2.47-2.31 (m, 1H), 2.20-2.01 (m, 1H).

Example 24: Synthesis of Compound WX016

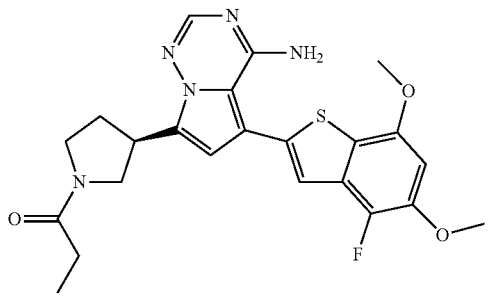 [SMILES: CCC(=O)N1CC[C@@H](c2cc(-c3cc4c(F)c(OC)cc(OC)c4s3)c3c(N)ncnn23)C1]

It was synthesized with reference to the synthesis method of WX001, using Intermediate A1-B and Intermediate B6 as the starting materials. LCMS (ESI) m/z: 470.1 [M+H]$^+$, $^1$H NMR (400 MHz, deuterated methanol) δ=7.79 (d, J=3.2 Hz, 1H), 7.20 (s, 1H), 6.71-6.49 (m, 2H), 4.06-3.78 (m, 8H), 3.68-3.58 (m, 1H), 3.57-3.34 (m, 3H), 3.15-3.05 (m, 1H), 2.24-1.98 (m, 2H), 1.07-1.00 (m, 3H).

Example 25: Synthesis of Compound WX017

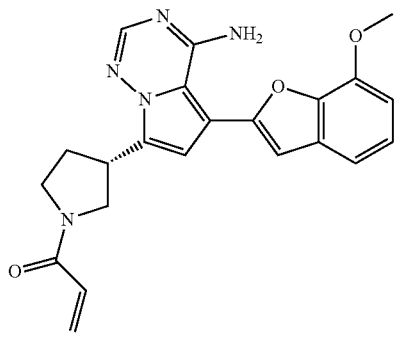 [SMILES: C=CC(=O)N1CC[C@H](c2cc(-c3cc4cccc(OC)c4o3)c3c(N)ncnn23)C1]

It was synthesized with reference to the synthesis method of WX001, using Intermediate A1-A and Intermediate B7 as the starting materials. LCMS (ESI) m/z: 404.2 [M+H]$^+$, 426.1 [M+Na]$^+$, $^1$H NMR (400 MHz, deuterated methanol) δ=7.74 (d, J=2.4 Hz, 1H), 7.12-7.02 (m, 2H), 6.97-6.88 (m, 2H), 6.79 (d, J=7.2 Hz, 1H), 6.59-6.50 (m, 1H), 6.24-6.10 (m, 1H), 5.70-5.64 (m, 1H), 4.28-3.94 (m, 1H), 3.90 (s, 3H), 3.84-3.45 (m, 3H), 3.20-3.18 (m, 1H), 2.49-2.31 (m, 1H), 2.24-2.01 (m, 1H).

Example 26: Synthesis of Compound WX018

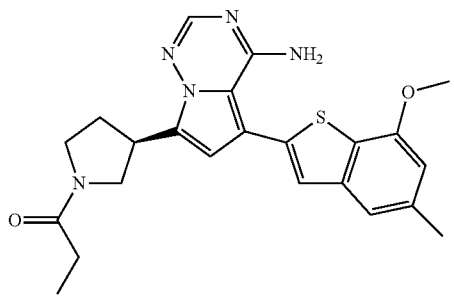 [SMILES: CCC(=O)N1CC[C@@H](c2cc(-c3cc4cc(C)cc(OC)c4s3)c3c(N)ncnn23)C1]

It was synthesized with reference to the synthesis method of WX001, using Intermediate A1-B and Intermediate B1 as the starting materials. LCMS (ESI) m/z: 436.1 [M+H]$^+$, 458.1 [M+Na]$^+$, $^1$H NMR (400 MHz, deuterated methanol) δ=7.76 (d, J=4.4 Hz, 1H), 7.10 (s, 2H), 6.67-6.61 (m, 1H), 6.56 (d, J=13.2 Hz, 1H), 3.97-3.89 (m, 1H), 3.86 (s, 3H), 3.65-3.55 (m, 1H), 3.53-3.30 (m, 2H), 3.20-3.18 (m, 1H), 2.35 (s, 3H), 2.33-2.16 (m, 3H), 2.15-1.98 (m, 1H), 1.07-0.97 (m, 3H).

Example 27: Synthesis of Compound WX019

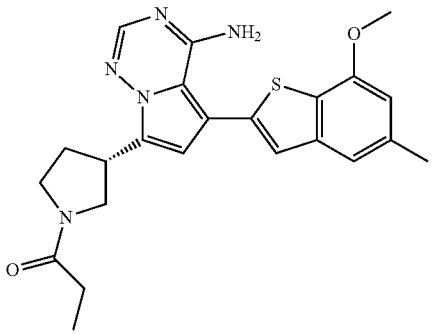 [SMILES: CCC(=O)N1CC[C@H](c2cc(-c3cc4cc(C)cc(OC)c4s3)c3c(N)ncnn23)C1]

It was synthesized with reference to the synthesis method of Example 1, using Intermediate A1-A and Intermediate B1 as the starting materials. LCMS (ESI) m/z: 436.1 [M+H]$^+$, 458.1 [M+Na]$^+$, $^1$H NMR (400 MHz, deuterated methanol) δ=7.78 (d, J=4.4 Hz, 1H), 7.14-7.10 (m, 2H), 6.64 (s, 1H), 6.58 (d, J=13.2 Hz, 1H), 4.03-3.91 (m, 1H), 3.87 (s, 3H), 3.66-3.57 (m, 1H), 3.55-3.32 (m, 2H), 3.21-3.18 (m, 1H), 2.45-2.32 (m, 4H), 2.28 (q, J=7.2 Hz, 2H), 2.19-2.01 (m, 1H), 1.05-1.01 (m, 3H).

Example 28: Synthesis of Compound WX020

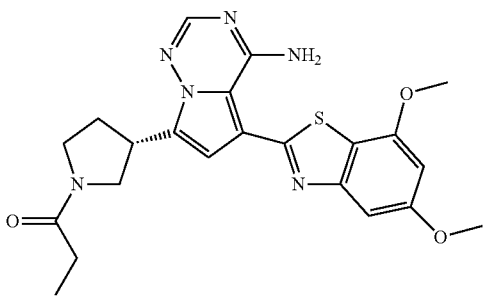 [SMILES: CCC(=O)N1CC[C@H](c2cc(-c3nc4cc(OC)cc(OC)c4s3)c3c(N)ncnn23)C1]

It was synthesized with reference to the synthesis method of Example 1, using Intermediate WX010-2 as the starting material. LCMS (ESI) m/z: 453.1 [M+H]$^+$.

Example 29: Synthesis of Compound WX021

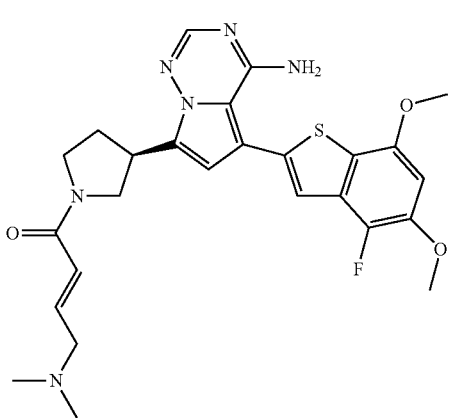 [SMILES: COc1cc(OC)c2sc(-c3cc([C@@H]4CCN(C(=O)/C=C/CN(C)C)C4)n4ncnc(N)c34)cc2c1F]

It was synthesized with reference to the synthesis methods of Example 1 and Example 9, using Intermediate A1-B, Intermediate B6 and oleic acid as the starting materials. LCMS (ESI) m/z: 525.1 [M+H]$^+$, 547.0 [M+Na]$^+$, $^1$H NMR (400 MHz, deuterated methanol) δ=7.91 (d, J=2.4 Hz, 1H), 7.30 (d, J=1.2 Hz, 1H), 6.93-6.80 (m, 1H), 6.79-6.65 (m, 2H), 6.53-6.47 (m, 1H), 4.28-4.06 (m, 1H), 4.06-3.91 (m, 6H), 3.90-3.70 (m, 2H), 3.69-3.52 (m, 1H), 3.32-3.28 (m, 1H), 3.27-3.09 (m, 2H), 2.59-2.40 (m, 1H), 2.38-2.28 (m, 6H), 2.28-2.16 (m, 1H).

Example 30: Synthesis of Compound WX022

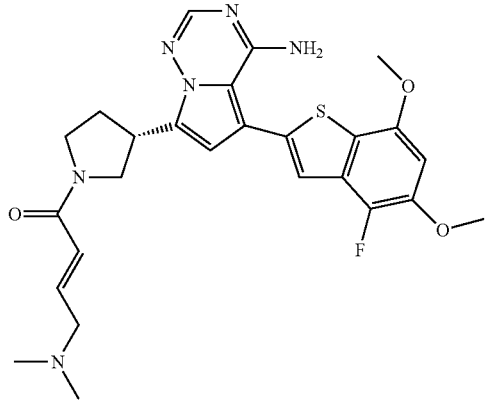 [SMILES: COc1cc(OC)c2sc(-c3cc([C@H]4CCN(C(=O)/C=C/CN(C)C)C4)n4ncnc(N)c34)cc2c1F]

It was synthesized with reference to the synthesis methods of Example 1 and Example 9, using Intermediate A1-A, Intermediate B6 and oleic acid as the starting materials. LCMS (ESI) m/z: 525.2 [M+H]$^+$, $^1$H NMR (400 MHz, deuterated methanol) δ=7.78 (d, J=2.4 Hz, 1H), 7.17 (s, 1H), 6.80-6.66 (m, 1H), 6.65-6.53 (m, 2H), 6.50-6.39 (m, 1H), 4.18-3.94 (m, 1H), 3.87 (s, 3H), 3.86 (s, 3H), 3.83-3.58 (m, 3H), 3.56-3.42 (m, 1H), 3.10 (q, J=7.2 Hz, 2H), 2.48-2.36 (m, 1H), 2.34 (s, 3H), 2.33 (s, 3H), 2.25-2.03 (m, 1H).

Example 31: Synthesis of Compound WX023A

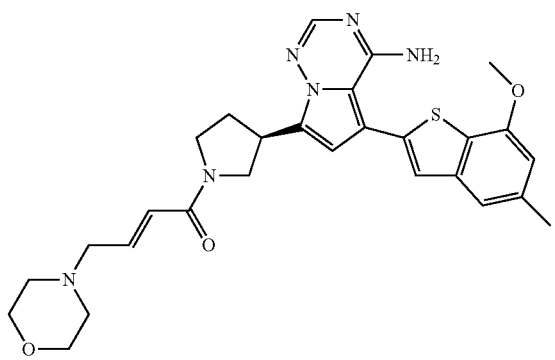 [SMILES: COc1cc(C)cc2cc(-c3cc([C@@H]4CCN(C(=O)/C=C/CN5CCOCC5)C4)n4ncnc(N)c34)sc12]

It was synthesized with reference to the synthesis methods of Example 1 and Example 9, using Intermediate A1-B, Intermediate B6 and Intermediate B8 as the starting materials. LCMS (ESI) m/z: 533.5[M+H]$^+$, $^1$H NMR (400 MHz, deuterated chloroform) δ=7.97 (d, J=5.2 Hz, 1H), 7.25-7.17 (m, 2H), 7.04-6.82 (m, 1H), 6.73-6.55 (m, 2H), 6.37-6.31 (m, 1H), 5.81 (br s, 2H), 4.34-4.11 (m, 1H), 4.10-3.94 (m, 4H), 3.91-3.86 (m, 1H), 3.81-3.59 (m, 6H), 3.17 (t, J=7.2 Hz, 2H), 2.60-2.38 (m, 8H), 2.30-2.14 (m, 1H).

Example 32: Synthesis of Compound WX023B

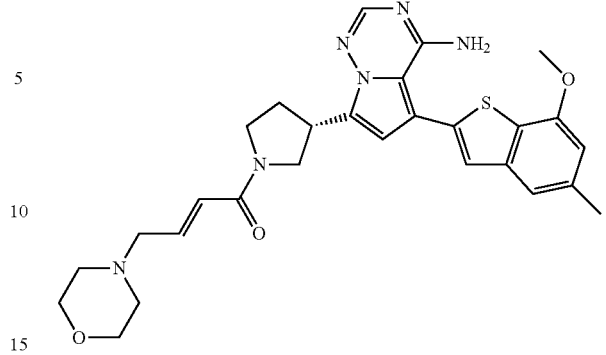

It was synthesized with reference to the synthesis methods of Example 1 and Example 9, using Intermediate A1-A, Intermediate B1 and Intermediate B8 as the starting materials. LCMS (ESI) m/z: 533.2[M+H]$^+$, $^1$H NMR (400 MHz, deuterated chloroform) δ=7.96 (d, J=5.6 Hz, 1H), 7.25-7.17 (m, 2H), 7.00-6.84 (m, 1H), 6.73-6.60 (m, 2H), 6.42-6.28 (m, 1H), 5.87 (br s, 2H), 4.25-4.10 (m, 1H), 4.09-3.95 (m, 4H), 3.90-3.78 (m, 1H), 3.77-3.59 (m, 6H), 3.26-3.12 (m, 2H), 2.62-2.39 (m, 8H), 2.31-2.15 (m, 1H).

Example 33: Synthesis of Compound WX024

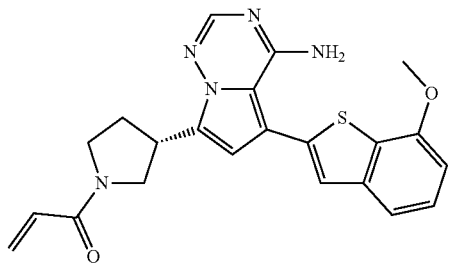 [SMILES: C=CC(=O)N1CC[C@H](c2cc(-c3cc4cccc(OC)c4s3)c3c(N)ncnn23)C1]

It was synthesized with reference to the synthesis method of Example 1, using Intermediate A1-A and Intermediate B9 as the starting materials. LCMS (ESI) m/z: 420.1 [M+H]$^+$, $^1$H NMR (400 MHz, deuterated methanol) δ=8.12 (d, J=1.6 Hz, 1H), 7.56-7.45 (m, 2H), 7.43-7.31 (m, 1H), 7.04-6.87 (m, 2H), 6.72-6.54 (m, 1H), 6.35-6.21 (m, 1H), 5.80-5.68 (m, 1H), 4.25-4.02 (m, 2H), 4.00 (s, 3H), 3.95-3.71 (m, 2H), 3.68-3.56 (m, 1H), 2.64-2.43 (m, 1H), 2.41-2.17 (m, 1H).

Example 34: Synthesis of Compound WX025

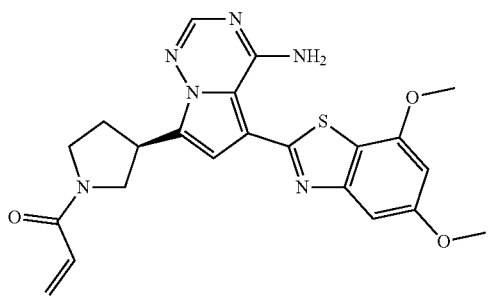 [SMILES: C=CC(=O)N1CC[C@@H](c2cc(-c3nc4cc(OC)cc(OC)c4s3)c3c(N)ncnn23)C1]

It was synthesized with reference to the synthesis methods of Examples 15 and 16 as well as Example 1, using Intermediate A1-B and Intermediate B5 as the starting materials. LCMS (ESI) m/z: 451.0 [M+H]$^+$, $^1$H NMR (400 MHz, deuterated chloroform) δ=7.94 (d, J=3.2 Hz, 1H), 7.01 (s, 1H), 6.90 (s, 1H), 6.60-6.38 (m, 3H), 5.76-5.69 (m, 1H), 4.31-4.13 (m, 1H), 4.11-3.86 (m, 7H), 3.80-3.54 (m, 3H), 2.70-2.38 (m, 1H), 2.31-2.22 (m, 1H).

NMR and MS Data for Each Example

| Example | Compound | NMR | MS m/z: |
|---|---|---|---|
| 1 | WX001A | $^1$H NMR (400 MHz, deuterated methanol) δ: 7.75 (d, J = 2.8 Hz, 1H), 7.12-7.04 (m, 2H), 6.61 (s, 1H), 6.56-6.40 (m, 2H), 6.20-6.15 (m, 1H), 5.65-5.60 (m, 1H), 4.11-3.94 (m, 1H), 3.85 (s, 3H), 3.81-3.38 (m, 4H), 2.48-2.26 (m, 4H), 2.22-1.93 (m, 1H). | 434.2 456.1 |
| 2 | WX001B | $^1$H NMR (400 MHz, deuterated methanol) $^1$H NMR (400 MHz, deuterated methanol) δ: 7.75 (d, J = 2.8 Hz, 1H), 7.08 (s, 2H), 6.61 (s, 1H), 6.54 (d, J = 6.4 Hz, 1H), 6.41-6.51 (m, 1H), 6.20-6.16 (m, 1H), 5.66-5.42 (m, 1H), 4.09-3.96 (m, 1H), 3.85 (s, 3H), 3.80-3.38 (m, 4H), 2.44-2.25 (m, 4H), 2.21-1.99 (m, 1H). | 434.2 456.1 |
| 4 | WX002A | $^1$H NMR (400 MHz, deuterated methanol) δ: 7.81 (d, J = 2.0 Hz, 1H), 7.36 (d, J = 1.6 Hz, 1H), 7.21 (s, 1H), 6.82 (s, 1H), 6.64 (d, J = 9.2 Hz, 1H), 6.58-6.50 (m, 1H), 6.22-6.17 (m, 1H), 5.68-5.63 (m 1H), 4.20-3.93 (m, 2H), 3.91 (s, 3H), 3.77-3.44 (m, 3H), 2.52-2.31 (m, 1H), 2.27-2.05 (m, 1H). | 454.1 |
| 5 | WX002B | $^1$H NMR (400 MHz, deuterated methanol) δ: 7.81 (d, J = 2.4 Hz, 1H), 7.36 (d, J = 1.6 Hz, 1H), 7.20 (s, 1H), 6.81 (s, 1H), 6.63 (d, J = 8.8 Hz, 1H), 6.58-6.50 (m, 1H), 6.22-6.17(m, 1H), 5.74-5.56 (m, 1H), 4.18-3.92 (m, 2H), 3.90 (s, 3H), 3.81-3.59 (m, 2H), 3.57-3.42 (m, 1H), 2.50-2.30 (m, 1H), 2.28-2.02 (m, 1H). | 454.1 |
| 6 | WX003 | $^1$H NMR (400 MHz, deuterated methanol) δ: 7.83-7.76 (m, 1H), 7.15 (s, 2H),6.75-6.68 (m, 1H), 6.66 (s, 1H), 6.61 (s, 1H), 6.14-6.06 (m, 1H), 5.68-5.58 (m, 1H), 4.42-4.27 (m, 1H), 3.88 (s, 3H), 3.40-3.27 (m, 2H), 3.08-2.83 (m, 2H), 2.37 (s, 3H), 2.13-2.02 (m, 1H), 1.86-1.72 (m, 2H), 1.63-1.54 (m, 1H). | 448.1, 470.2 |
| 7 | WX004A | $^1$H NMR (400 MHz, deuterated methanol) δ: 7.90 (d, J = 2.0 Hz, 1H), 7.21 (s, 1H), 6.81 (s, 1H), 6.73-6.57 (m, 2H), 6.34-6.33 (m, 1H), 5.80-5.75 (m, 1H), 4.32-4.12 (m, 1H), 4.11-3.95 (m, 4H), 3.93-3.72 (m, 2H), 3.70-3.64 (m, 1H), 2.64-2.42 (m, 4H), 2.39-2.16 (m, 4H). | 448.2 470.2 |
| 8 | WX004B | $^1$H NMR (400 MHz, deuterated methanol) δ: 7.78 (d, J = 2.0 Hz, 1H), 7.09 (s, 1H), 6.69 (s, 1H), 6.63-6.44 (m, 2H), 6.22-6.17 (m, 1H), 5.73-5.54 (m, 1H), 4.24-4.01 (m, 1H), 4.00-3.89 (m, 1H), 3.87 (s, 3H), 3.80-3.60 (m, 2H), 3.57-3.44 (m, 1H), 2.52-2.32 (m, 4H), 2.30-2.10 (m, 4H). | 448.2 |
| 9 | WX005 | $^1$H NMR (400 MHz, deuterated methanol) δ: 7.80 (d, J = 2.0 Hz, 1H), 7.32 (d, J = 1.2 Hz, 1H), 6.87 (s, 1H), 6.67-6.49 (m, 2H), 6.25-6.03 (m, 1H), 5.70-5.59 (m, 1H), 4.24-4.00 (m, 1H), 3.99-3.85 (m, 3H), 3.83-3.60 (m, 2H), 3.58-3.41 (m, 1H), 3.40-3.26 (m, 1H), 2.50-2.34 (m, 1H), 2.32-2.19 (m, 1H), 2.17 (s, 3H). | 490.1 |
| 10 | WX006A | $^1$H NMR (400 MHz, deuterated methanol) δ = 7.78 (d, J = 7.2 Hz, 1H), 7.13 (s, 2H), 6.64 (s, 1H), 6.59 (d, J = 6.8 Hz, 1H), 3.98-3.74 (m, 5H), 3.69-3.55 (m, 2H), 3.47-3.34 (m, 1H), 2.46-2.31 (m, 4H), 2.22-2.07 (m, 1H), 1.93 (d, J = 9.2 Hz, 3H). | 446.1, 468.1 |
| 11 | WX006B | $^1$H NMR (400 MHz, deuterated methanol) δ = 7.78 (d, J = 7.2 Hz, 1H), 7.13 (s, 2H), 6.64 (s, 1H), 6.59 (d, J = 6.4 Hz, 1H), 4.00-3.73 (m, 5H), 3.70-3.51 (m, 2H), 3.45-3.34 (m, 1H), 2.36 (s, 4H), 2.23-2.06 (m, 1H), 1.93 (d, J = 9.2 Hz, 3H). | 446.1, 468.0 |
| 12 | WX007A | $^1$H NMR (400 MHz, deuterated methanol) δ: 7.76 (d, J = 3.6 Hz, 1H), 7.09 (s, 2H), 6.79-6.67 (m, 1H), 6.62 (s, 1H), 6.55 (d, J = 8.8 Hz, 1H), 6.37-6.32 (m, 1H), 4.12-3.92 (m, 1H), 3.86 (s, 3H), 3.81-3.72 (m, 1H), 3.70-3.39 (m, 3H), 3.07-2.99 (m, 2H), 2.39-2.25 (m, 4H), 2.16 (s, 3H), 2.15 (s, 3H), 2.12-1.99 (m, 1H). | 491.2, 513.1 |
| 13 | WX007B | $^1$H NMR (400 MHz, deuterated methanol) δ: 7.76 (d, J = 3.2 Hz, 1H), 7.10 (s, 2H), 6.79-6.68 (m, 1H), 6.63 (s, 1H), 6.56 (d, J = 9.2 Hz, 1H), 6.38-6.33 (m, 1H), 4.15-3.94 (m, 1H), 3.86 (s, 3H), 3.83-3.71 (m, 1H), 3.69-3.40 (m, 3H), 3.06-3.03 (m, 2H), 2.40-2.32 (m, 4H), 2.17 (s, 3H), 2.15 (s, 3H), 2.12-1.97 (m, 1H). | 491.2, 513.1 |
| 14 | WX008 | $^1$H NMR (400 MHz, deuterated methanol) δ: 7.81 (d, J = 3.6 Hz, 1H), 7.15 (d, J = 2.4 Hz, 2H), 6.77 (d, J = 3.6 Hz, 1H), 6.65 (s, 1H), 6.63-6.44 (m, 1H), 6.24-6.19 (m, 1H), 5.72-5.57 (m, 1H), 4.17-3.93 (m, 2H), 3.88 (s, 3H), 3.85-3.56 (m, 2H), 2.86-2.61 (m, 1H), 2.37 (s, 3H), 2.34-2.20 (m, 1H). | 432.1, 450.1 |
| 15 | WX009A | $^1$H NMR (400 MHz, deuterated methanol) δ: 7.79 (d, J = 1.2 Hz, 1H), 7.16 (d, J = 1.6 Hz, 2H), 6.75-6.54 (m, 2H), 4.05-3.93 (m, 2H), 3.88 (s, 3H), 3.70-3.59 (m, 1H), 3.56-3.39 (m, 2H), 2.48-2.33 (m, 4H), 2.25-2.01 (m, 1H). | 447.2, 469.1 |
| 16 | WX009B | $^1$H NMR (400 MHz, deuterated methanol) δ: 7.79 (d, J = 1.6 Hz, 1H), 7.16 (d, J = 1.6 Hz, 2H), 6.74-6.51 (m, 2H), 4.10-3.91 (m, 2H), 3.88 (s, 3H), 3.71-3.59 (m, 1H), 3.58-3.40 (m, 2H), 2.50-2.27 (m, 4H), 2.26-1.99 (m, 1H). | 447.2, 469.4 |

-continued

| Example | Compound | NMR | MS m/z: |
|---|---|---|---|
| 17 | WX010 | ¹H NMR (400 MHz, deuterated methanol) δ = 7.86 (s, 1H), 7.09-6.93 (m, 2H), 6.70-6.64 (m, 1H), 6.55 (s, 1H), 6.37-6.31 (m, 1H), 5.82-5.79 (m, 1H), 4.34-4.09 (m, 1H), 3.97 (s, 3H), 3.89-3.83 (m, 5H), 3.82-3.69 (m, 1H), 3.68-3.55 (m, 1H), 2.62-2.41 (m, 1H), 2.38-2.12 (m, 1H). | 473.1 |
| 18 | WX011A | ¹H NMR (400 MHz, CDC$_3$) δ: 7.85 (d, J = 8.4 Hz, 1H), 7.20 (s, 1H), 7.16 (s, 1H), 6.62 (s, 1H), 6.51-6.30 (m, 2H), 5.68-5.60 (m, 1H), 5.47 (2H, brs), 4.34 (s, 2H), 4.18-3.78 (m, 7H), 3.65-3.48 (m, 1H), 3.22 (d, J = 10.0 Hz, 3H), 2.85-2.65 (m, 1H), 2.44 (s, 3H). | 478.1, 500.1 |
| 19 | WX011B | ¹H NMR (400 MHz, CDCl$_3$) δ: 7.84 (d, J = 8.8 Hz, 1H), 7.20 (s, 1H), 7.16 (s, 1H), 6.62 (s, 1H), 6.51-6.30 (m, 2H), 5.68-5.60 (m, 1H), 5.42 (2H, brs), 4.34 (s, 2H), 4.15-3.72 (m, 7H), 3.62-3.48 (m, 1H), 3.22 (d, J = 10.4 Hz, 3H), 2.90-2.65 (m, 1H), 2.44 (s, 3H). | 478.1, 500.0 |
| 20 | WX012 | ¹H NMR (400 MHz, CDCl$_3$) δ = 7.90-7.80 (m, 1H), 7.22-7.18 (m, 1H), 7.16 (s, 1H), 6.65-6.60 (m, 1H), 6.57 (brs, 2H), 4.38-4.30 (m, 2H), 4.20-3.90 (m, 6H), 3.89-3.70 (m, 1H), 3.68-3.38 (m, 1H), 3.28-3.18 (m, 3H), 2.80-2.65 (m, 1H), 2.44 (s, 3H), 2.18-2.08 (m, 1H), 1.98-1.85 (m, 3H). | 490.0, 512.0 |
| 21 | WX013 | ¹H NMR (400 MHz, deuterated methanol) δ = 7.79 (d, J = 3.2 Hz, 1H), 7.20 (s, 1H), 6.72-6.54 (m, 2H), 4.09-3.91 (m, 1H), 3.88 (s, 3H), 3.87 (s, 3H), 3.85-3.72 (m, 1H), 3.67-3.37 (m, 4H), 2.32-2.25 (m, 2H), 1.05-1.00 (m, 3H). | 470.1 |
| 22 | WX014 | ¹H NMR (400 MHz, deuterated methanol) δ = 7.90 (br s, 1H), 7.31 (br d, J = 10.0 Hz, 1H), 6.83-6.69 (m, 2H), 6.69-6.55 (m, 1H), 6.39-6.21 (m, 1H), 5.83-5.70 (m, 1H), 4.69 (br d, J = 2.0 Hz, 1H), 4.28-4.04 (m, 1H), 3.99 (d, J = 3.6 Hz, 3H), 3.97 (d, J = 2.4 Hz, 4H), 3.89-3.70 (m, 2H), 3.64-3.54 (m, 1H), 2.63-2.42 (m, 1H), 2.33-2.13 (m, 2H). | 468.1 |
| 23 | WX015 | ¹H NMR (400 MHz, deuterated methanol) δ = 7.79 (d, J = 1.6 Hz, 1H), 7.18 (d, J = 1.6 Hz, 1H), 6.65-6.60 (m, 2H), 6.56-6.47 (m, 1H), 6.28-6.03 (m, 1H), 5.74-5.57 (m, 1H), 4.17-3.97 (m, 1H), 3.88 (s, 3H), 3.86 (s, 3H), 3.77-3.59 (m, 2H), 3.50-3.38 (m, 1H), 23.07-2.96 (m, 1H), 2.47-2.31 (m, 1H), 2.20-2.01 (m, 1H). | 468.1 |
| 24 | WX016 | ¹H NMR (400 MHz, deuterated methanol) δ = 7.79 (d, J = 3.2 Hz, 1H), 7.20 (s, 1H), 6.71-6.49 (m, 2H), 4.06-3.78 (m, 8H), 3.68-3.58 (m, 1H), 3.57-3.34 (m, 3H), 3.15-3.05 (m, 1H), 2.24-1.98 (m, 2H), 1.07-1.00 (m, 3H). | 470.1 |
| 25 | WX017 | ¹H NMR (400 MHz, deuterated methanol) δ = 7.74 (d, J = 2.4 Hz, 1H), 7.12-7.02 (m, 2H), 6.97-6.88 (m, 2H), 6.79 (d, J = 7.2 Hz, 1H), 6.59-6.50 (m, 1H), 6.24-6.10 (m, 1H), 5.70-5.64 (m, 1H), 4.28-3.94 (m, 1H), 3.90 (s, 3H), 3.84-3.45 (m, 3H), 3.20-3.18 (m, 1H), 2.49-2.31 (m, 1H), 2.24-2.01 (m, 1H). | 404.2 426.1 |
| 26 | WX018 | ¹H NMR (400 MHz, deuterated methanol) δ = 7.76 (d, J = 4.4 Hz, 1H), 7.10 (s, 2H), 6.67-6.61 (m, 1H), 6.56 (d, J = 13.2 Hz, 1H), 3.97-3.89 (m, 1H), 3.86 (s, 3H), 3.65-3.55 (m, 1H), 3.53-3.30 (m, 2H), 3.20-3.18 (m, 1H), 2.35 (s, 3H), 2.33-2.16 (m, 3H), 2.15-1.98 (m, 1H), 1.07-0.97 (m, 3H). | 436.1 458.1 |
| 27 | WX019 | ¹H NMR (400 MHz, deuterated methanol) δ = 7.78 (d, J = 4.4 Hz, 1H), 7.14-7.10 (m, 2H), 6.64 (s, 1H), 6.58 (d, J = 13.2 Hz, 1H), 4.03-3.91 (m, 1H), 3.87 (s, 3H), 3.66-3.57 (m, 1H), 3.55-3.32 (m, 2H), 3.21-3.18 (m, 1H), 2.45-2.32 (m, 4H), 2.28 (q, J = 7.2 Hz, 2H), 2.19-2.01 (m, 1H), 1.05-1.01 (m, 3H). | 436.1 458.1 |
| 28 | WX020 | | 453.1 |
| 29 | WX021 | ¹H NMR (400 MHz, deuterated methanol) δ = 7.91 (d, J = 2.4 Hz, 1H), 7.30 (d, J +32 1.2 Hz, 1H), 6.93-6.80 (m, 1H), 6.79-6.65 (m, 2H), 6.53-6.47 (m, 1H), 4.28-4.06 (m, 1H), 4.06-3.91 (m, 6H), 3.90-3.70 (m, 2H), 3.69-3.52 (m, 1H), 3.32-3.28 (m, 1H), 3.27-3.09 (m, 2H), 2.59-2.40 (m, 1H), 2.38-2.28 (m, 6H), 2.28-2.16 (m, 1H). | 525.1, 547.0 |
| 30 | WX022 | ¹H NMR (400 MHz, deuterated methanol) δ = 7.78 (d, J = 2.4 Hz, 1H), 7.17 (s, 1H), 6.80-6.66 (m, 1H), 6.65-6.53 (m, 2H), 6.50-6.39 (m, 1H), 4.18-3.94 (m, 1H), 3.87 (s, 3H), 3.86 (s, 3H), 3.83-3.58 (m, 3H), 3.56-3.42 (m, 3H), 3.10 (q, J = 7.2 Hz, 2H), 2.48-2.36 (m, 1H), 2.34 (s, 3H), 2.33 (s, 3H), 2.25-2.03 (m, 1H). | 525.2 |
| 31 | WX023A | ¹H NMR (400 MHz, deuterated chloroform) δ = 7.97 (d, J = 5.2 Hz, 1H), 7.25-7.17 (m, 2H), 7.04-6.82 (m, 1H), 6.73-6.55 (m, 2H), 6.37-6.31 (m, 1H), 5.81 (br s, 2H), 4.34-4.11 (m, 1H), 4.10-3.94 (m, 4H), 3.91-3.86 (m, 1H), 3.81-3.59 (m, 6H), 3.17 (t, J = 7.2 Hz, 2H), 2.60-2.38 (m, 8H), 2.30-2.14 (m, 1H). | 533.5 |
| 32 | WX023B | ¹H NMR (400 MHz, deuterated chloroform) δ = 7.96 (d, J = 5.6 Hz, 1H), 7.25-7.17 (m, 2H), 7.00-6.84 (m, 1H), 6.73-6.60 (m, 2H), 6.42-6.28 (m, 1H), 5.87 (br s, 2H), 4.25-4.10 (m, 1H), 4.09-3.95 (m, 4H), 3.90-3.78 (m, 1H), 3.77-3.59 (m, 6H), 3.26-3.12 (m, 2H), 2.62-2.39 (m, 8H), 2.31-2.15 (m, 1H). | 533.2 |
| 33 | WX024 | ¹H NMR (400 MHz, deuterated methanol) δ = 8.12 (d, J = 1.6 Hz, 1H), 7.56-7.45 (m, 2H), 7.43-7.31 (m, 1H), 7.04-6.87 (m, 2H), 6.72-6.54 (m, 1H), 6.35-6.21 (m, 1H), 5.80-5.68 (m, 1H), 4.25-4.02 (m, 2H), 4.00 (s, 3H), 3.95-3.71 (m, 2H), 3.68-3.56 (m, 1H), 2.64-2.43 (m, 1H), 2.41-2.17 (m, 1H). | 420.1 |

| Example | Compound | NMR | MS m/z: |
|---|---|---|---|
| 34 | WX025A | $^1$H NMR (400 MHz, deuterated chloroform) δ = 7.94 (d, J = 3.2 Hz, 1H), 7.01 (s, 1H), 6.90 (s, 1H), 6.60-6.38 (m, 3H), 5.76-5.69 (m, 1H), 4.31-4.13 (m, 1H), 4.11-3.86 (m, 7H), 3.80-3.54 (m, 3H), 2.70-2.38 (m, 1H), 2.31-2.22 (m, 1H). | 451.0 |

Assay 1: Evaluation of Wild-Type Kinase Inhibitory Activity In Vitro

The $^{33}$P isotope-labeled kinase activity test (Reaction Biology Corp) was used to determine the IC$_{50}$ value to evaluate the inhibitory ability of the test compound on human FGFR1 and FGFR4.

Buffer conditions: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO.

Assay step: The test compound was dissolved in DMSO at room temperature to prepare a 10 mM solution for use. The substrate was dissolved in a freshly prepared buffer, the test kinase was added thereto, and the resulting reaction solution was uniformly mixed. By using the acoustic technique (Echo 550), the DMSO solution in which the test compound was dissolved was added to the above-mentioned uniformly mixed reaction solution. The compound concentrations in the reaction solutions were 10 μM, 3.33 μM, 1.11 μM, 0.370 μM, 0.123 μM, 41.2 nM, 13.7 nM, 4.57 nM, 1.52 nM, and 0.508 nM respectively, or were 10 μM, 2.50 μM, 0.62 μM, 0.156 μM, 39.1 nM, 9.8 nM, 2.4 nM, 0.61 nM, 0.15 nM, and 0.038 nM respectively. 15 minutes after the incubation, $^{33}$P-ATP (activity 0.01 μCi/μl, the corresponding concentration was shown in Table 1) was added to start the reaction. The information about the supplier's category number, lot number, and the concentration in the reaction solution of FGFR1, FGFR4, and their substrates were listed in Table 1. After the reaction was carried out at room temperature for 120 minutes, the reaction solution was spotted on a P81 ion exchange filter paper (Whatman #3698-915). After repeatedly washing the filter paper with a 0.75% phosphoric acid solution, the radioactivity of the phosphorylated substrate remaining on the filter paper was measured. The kinase activity data was expressed by a comparison of the kinase activity of the test compound and the kinase activity of the blank group (containing only DMSO). IC$_{50}$ values were obtained by curve fitting using Prism4 software (GraphPad). The experimental results were shown in Table 2.

TABLE 2

Results for the in vitro screening test of the compounds of the present invention

| Compound | IC$_{50}$ (nM) FGFR1 | FGFR4 |
|---|---|---|
| Reference Example 1 | 0.9 | 3.1 |
| Reference Example 2 | 570 | 8754 |
| Reference Example 3 | 1.7 | 17.3 |
| Reference Example 4 | 0.7 | 32 |
| Reference Example 5 | 0.6 | 43 |
| Reference Example 6 | 1.2 | 2.1 |
| Reference Example 7 | 0.8 | 4.5 |
| Example 1 | 0.4 | 0.9 |
| Example 2 | 0.2 | 0.2 |
| Example 4 | 0.6 | 4.1 |
| Example 5 | 0.3 | 0.7 |
| Example 6 | 1.7 | 5.4 |
| Example 7 | 0.7 | 8.5 |
| Example 8 | 0.1 | 0.7 |
| Example 9 | 0.7 | 3.3 |
| Example 10 | 0.2 | 1.5 |
| Example 11 | 0.1 | 0.1 |
| Example 12 | 0.2 | 2.6 |
| Example 13 | 0.6 | 8.7 |
| Example 14 | 0.8 | 6.6 |
| Example 15 | 1.5 | 6.2 |
| Example 16 | 0.8 | 5.3 |
| Example 17 | >10,000 | >10,000 |
| Example 18 | 0.1 | 0.2 |
| Example 19 | 0.1 | 0.1 |
| Example 20 | 0.2 | 0.8 |
| Example 21 | 6.6 | 138 |
| Example 22 | 1.5 | 9.9 |
| Example 23 | 0.2 | 0.2 |
| Example 24 | 2.2 | 40 |
| Example 25 | 250 | 477 |
| Example 26 | 1.2 | 4.2 |
| Example 27 | 4.7 | 67 |
| Example 28 | >10,000 | >10,000 |
| Example 29 | 0.5 | 9.2 |
| Example 30 | 1.6 | 20 |
| Example 31 | 1.1 | 9.6 |
| Example 32 | 4.7 | 80 |

TABLE 1

Relevant information about kinase, substrate, and ATP in the in vitro test

| Kinase | supplier | Cat # | Lot # | Kinase concentration in the reaction solution (nM) | ATP concentration (μM) |
|---|---|---|---|---|---|
| FGFR4 | Invitrogen | P3054 | 26967J | 2.5 | 100 |
| FGFR1 | Invitrogen | PV3146 | 28427Q | 1.75 | 5 |

| Substrate | Supplier | Cat# | Lot # | Substrate concentration in the reaction solution (μM) |
|---|---|---|---|---|
| pEY (mg/ml) + Mn | Sigma | P7244-250MG | 062K5104V | 0.2 |
| pEY (mg/ml) + Mn | Sigma | P7244-250MG | 062K5104V | 0.2 |

TABLE 2-continued

Results for the in vitro screening test of the compounds of the present invention

| Compound | IC$_{50}$ (nM) | |
|---|---|---|
| | FGFR1 | FGFR4 |
| Example 33 | 0.5 | 0.9 |
| Example 34 | 126 | 462 |

Conclusion: The compounds of the present invention exhibited good inhibitory activity against wild-type kinases.

Assay 2: Evaluation of Mutant Kinase Inhibitory Activity In Vitro

The $^{33}$P isotope-labeled kinase activity test (Reaction Biology Corp) was adopted to determine the IC$_{50}$ value to evaluate the inhibitory ability of the test compound on FGFR mutant strain.

Buffer conditions: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO.

Assay step: The test compound was dissolved in DMSO at room temperature to prepare a 10 mM solution for use. The substrate was dissolved in a freshly prepared buffer, the test kinase was added thereto, and the resulting reaction solution was uniformly mixed. By using the acoustic technique (Echo 550), the DMSO solution in which the test compound was dissolved was added to the above-mentioned uniformly mixed reaction solution. The compound concentrations in the reaction solutions were 10 μM, 3.33 μM, 1.11 μM, 0.370 μM, 0.123 μM, 41.2 nM, 13.7 nM, 4.57 nM, 1.52 nM, and 0.508 nM respectively, or were 10 μM, 2.50 μM, 0.62 μM, 0.156 μM, 39.1 nM, 9.8 nM, 2.4 nM, 0.61 nM, 0.15 nM, and 0.038 nM respectively. 15 minutes after the incubation, 33P-ATP (activity 0.01 μCi/μl, the corresponding concentration was shown in Table 3) was added to start the reaction. The information about the supplier's category number, lot number, and the concentration in the reaction solution of FGFR1, FGFR4, and their substrates were listed in Table 3. After the reaction was carried out at room temperature for 120 minutes, the reaction solution was spotted on a P81 ion exchange filter paper (Whatman #3698-915). After repeatedly washing the filter paper with a 0.75% phosphoric acid solution, the radioactivity of the phosphorylated substrate remaining on the filter paper was measured. The kinase activity data was expressed by a comparison of the kinase activity of the test compound and the kinase activity of the blank group (containing only DMSO). IC$_{50}$ values were obtained by curve fitting using Prism4 software (GraphPad). The experimental results were shown in Table 4.

TABLE 3

Relevant information about kinase, substrate, and ATP in the in vitro test

| Kinase | Supplier | Cat# | Kinase concentration in the reaction solution (nM) | ATP concentration (μM) |
|---|---|---|---|---|
| FGFR2 (N549H) | Millipore | 14-742 | 0.3 | 50 |
| FGFR1 (V561M) | Signal Chem | F04-13G | 15 | 10 |
| FGFR2 (E565G) | Signal Chem | F05-12CG | 0.5 | 10 |
| FGFR2 (V564F) | SignalChem | F05-12FG | 0.3 | 20 |
| FGFR3 (V555M) | SignalChem | F06-12GG | 4 | 20 |
| FGFR3 (K650M) | Carna Biosciences | Carna 08-199 | 2 | 2.5 |
| FGFR4 (N535K) | Carna Biosciences | Carna 08-524 | 75 | 2.5 |
| FGFR4 (V550M) | Signal Chem | F07-12DG | 6 | 2.5 |

| Kinase | Substrate | Supplier | Cat# | Substrate concentration in the reaction solution (μM) |
|---|---|---|---|---|
| FGFR2 (N549H) | pEY | Sigma | P7244-250MG | 0.2 mg/mL |
| FGFR1 (V561M) | pEY + Mn | Sigma | P7244-250MG | 0.2 mg/mL |
| FGFR2 (E565G) | pEY | Sigma | P7244-250MG | 0.2 mg/mL |
| FGFR2 (V564F) | pEY | Sigma | P7244-250MG | 0.2 mg/mL |
| FGFR3 (V555M) | pEY + Mn | Sigma | P7244-250MG | 0.2 mg/mL |
| FGFR3 (K650M) | pEY + Mn | Sigma | P7244-250MG | 0.2 mg/mL |
| FGFR4 (N535K) | pEY + Mn | Sigma | P7244-250MG | 0.2 mg/mL |
| FGFR4 (V550M) | pEY + Mn | Sigma | P7244-250MG | 0.2 mg/mL |

TABLE 4

Results for the in vitro screening test of the
compounds of the present invention

| Kinase | Reference Example 4 (nM) | Reference Example 5 (nM) | Reference Example 6 (nM) | Reference Example 1 (nM) | Example 2 (nM) |
|---|---|---|---|---|---|
| FGFR2 (N549H) | 4.3 | 8.4 | 30 | 2.4 | 0.5 |
| FGFR1 (V561M) | 491 | 2473 | 1313 | 605 | 38 |
| FGFR2 (E565G) | 3.5 | 3.2 | 7.2 | 1.4 | 0.1 |
| FGFR2 (V564F) | 1.0 | 1770 | 6520 | 255 | 33 |
| FGFR3 (V555M) | 172 | 212 | 888 | 23 | 7.3 |
| FGFR3 (K650M) | 28 | 4.4 | 27 | 2.0 | 0.2 |
| FGFR4 (N535K) | 1431 | 157 | 1345 | 1812 | 34 |
| FGFR4 (V550M) | 2407 | 834 | 3964 | 94 | 5.6 |

Conclusion: Some compounds in the present invention exhibited good inhibitory activity on both wild-type and mutant FGFRs.

Assay 3: Evaluation of Compounds' Pharmacokinetics

Experiment purpose: To test the pharmacokinetics of the compound in mice in vivo.

Experimental Materials:
Balb/c mice (female)

Experimental Procedures:

The pharmacokinetics profile in rodents after the intravenous injection and the oral administration of the compound was tested using a standard protocol. In experiments, the candidate compound was prepared as a clear solution, which was administered to the mice as a single intravenous injection and as an oral administration. The medium for the intravenous injection was 10% DMSO/10% solutol/80% water, and the medium for the oral administration was 0.5% sodium carboxymethylcellulose+0.2% Tween. The whole blood samples within 24 hours were collected. All blood samples were added to the well-labeled plastic centrifuge tubes, to which 0.5M K2-EDTA anticoagulant was added in advance. After the collection of blood samples, the blood samples were centrifuged at 4° C. at 3000 g for 10 minutes. The supernatant plasma was collected, promptly placed in the dry ice, and kept at a temperature of −20° C. or lower. The LC-MS/MS analysis method was used to quantitatively analyze the blood concentration, and the pharmacokinetics parameters, such as peak concentration, peak time, clearance rate, half-life, area under the curve and bioavailability were calculated.

Experimental Result:

TABLE 5

Pharmacokinetics test results

| | Intravenous injection (3 npk) | | | Oral administration (10 npk) | |
|---|---|---|---|---|---|
| Test substance (Compound) | Clearance rate (mL/min/kg) | Half-life $T_{1/2}$ (h) | Area under the curve, AUC (nM · hr) | Area under the curve, AUC (nM · hr) | Bioavailability F (%) |
| WXR1 | 22 | 0.7 | 5287 | 11898 | 69 |
| Example 2 | 22.7 | 1.09 | 5073 | 4440 | 27.5 |
| Example 15 | 52 | 0.8 | 2034 | 4801 | 70 |

Conclusion: The pharmacokinetic index of the compounds of the present invention was good in mice.

The invention claimed is:

1. A compound represented by formula (I):

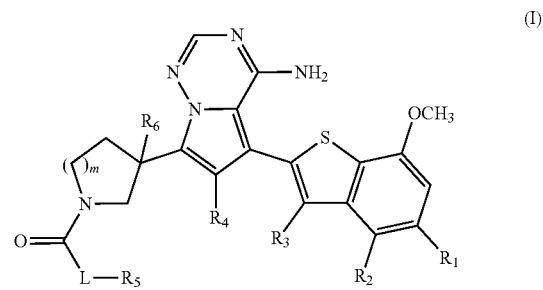

or a pharmaceutically acceptable salt or stereoisomer thereof, wherein:
$R_1$ is H, halogen, $C_{1-3}$ alkyl, $C_{1-3}$ heteroalkyl, $NH_2$, or OH, wherein the $C_{1-3}$ alkyl or $C_{1-3}$ heteroalkyl is optionally substituted with 1, 2, or 3 independently selected R substituents;

$R_2$ is H, F, Cl, Br, I, $NH_2$, or OH;

$R_3$ is H, halogen, CN, $C_{1-3}$ alkyl, $C_{1-3}$ heteroalkyl, $NH_2$, or OH, wherein the $C_{1-3}$ alkyl or $C_{1-3}$ heteroalkyl is optionally substituted with 1, 2, or 3 independently selected R substituents;

$R_4$ is H, halogen, CN, $C_{1-3}$ alkyl, $C_{1-3}$ heteroalkyl, $NH_2$, or OH, wherein the $C_{1-3}$ alkyl or $C_{1-3}$ heteroalkyl is optionally substituted with 1, 2, or 3 independently selected R substituents;

L is a single bond, C$_{2-4}$ alkenylene, or C$_{2-4}$ alkynylene;

R$_5$ is H, C$_{1-3}$ alkyl, C$_{1-3}$ heteroalkyl, C$_{3-6}$ cycloalkyl, or 4- to 6-membered heterocycloalkyl, wherein the C$_{1-3}$ alkyl, C$_{1-3}$ heteroalkyl, C$_{3-6}$ cycloalkyl, or 4- to 6-membered heterocycloalkyl is optionally substituted with 1, 2, or 3 independently selected R substituents;

R$_6$ is H, halogen, C$_{1-3}$ alkyl, NH$_2$, or OH, wherein the C$_{1-3}$ alkyl is optionally substituted with 1, 2, or 3 independently selected R substituents;

each R is independently F, Cl, Br, I, CN, CH$_3$, CF$_3$, NH$_2$, N(CH$_3$)$_2$, OH, or OCH$_3$; and m is 1 or 2;

wherein each heteroatom or each heteroatomic group of each C$_{1-3}$ heteroalkyl and each 4- to 6-membered heterocycloalkyl is 1, 2, or 3 heteroatoms or heteroatomic groups independently selected from the group consisting of N, —NH—, —O—, and —S—.

2. The compound according to claim 1, wherein the compound is represented by formula (I-1) or formula (I-2):

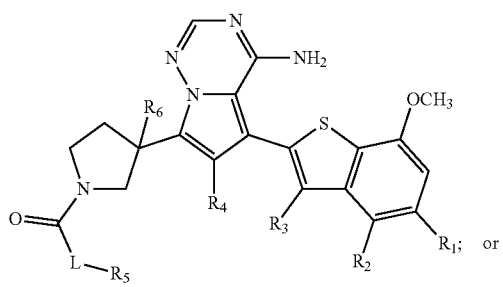
(I-1)

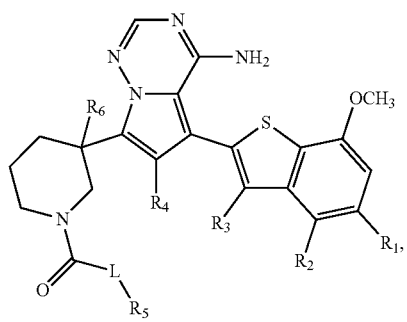
(I-2)

or a pharmaceutically acceptable salt or stereoisomer thereof.

3. The compound according to claim 2, or a stereoisomer thereof, wherein the compound, or stereoisomer thereof, is represented by formula (I-1A), formula (I-1B), formula (I-2A), or formula (I-2B):

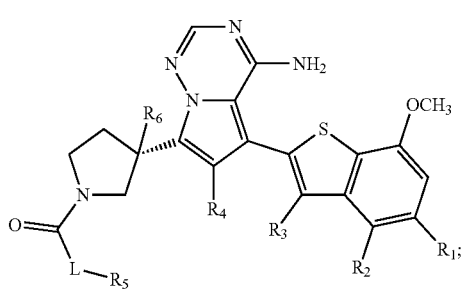
(I-1A)

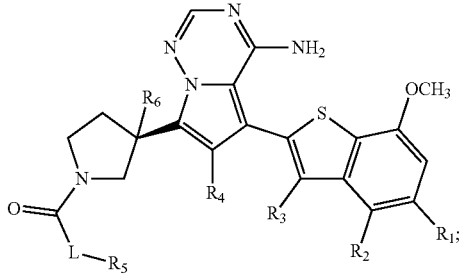
(I-1B)

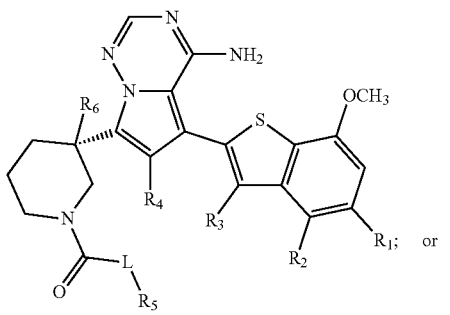
(I-2A)

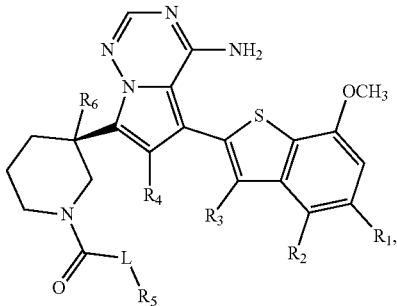
(I-2B)

or a pharmaceutically acceptable salt thereof.

4. The compound according to claim 1, or a pharmaceutically acceptable salt or stereoisomer thereof, wherein R$_1$ is H, halogen, C$_{1-3}$ alkyl, NH$_2$, OH, or OC$_{1-3}$ alkyl, wherein the C$_{1-3}$ alkyl or OC$_{1-3}$ alkyl is optionally substituted with 1, 2, or 3 independently selected R substituents.

5. The compound according to claim 4, or a pharmaceutically acceptable salt or stereoisomer thereof, wherein R$_1$ is H, F, Cl, Br, I, CH$_3$, NH$_2$, OH, or OCH$_3$.

6. The compound according to claim 1, or a pharmaceutically acceptable salt or stereoisomer thereof, wherein R$_3$ is H, halogen, CN, C$_{1-3}$ alkyl, NH$_2$, NHC$_{1-3}$ alkyl, N(C$_{1-3}$ alkyl)$_2$, OH, or OC$_{1-3}$ alkyl, wherein the C$_{1-3}$ alkyl, NHC$_{1-3}$ alkyl, N(C$_{1-3}$ alkyl)$_2$, or OC$_{1-3}$ alkyl is optionally substituted with 1, 2, or 3 independently selected R substituents.

7. The compound according to claim 6, or a pharmaceutically acceptable salt or stereoisomer thereof, wherein R$_3$ is H, F, Cl, Br, I, CN, CH$_3$, CF$_3$, NH$_2$, N(CH$_3$)$_2$, OH, or OCH$_3$.

8. The compound according to claim 1, or a pharmaceutically acceptable salt or stereoisomer thereof, wherein is:

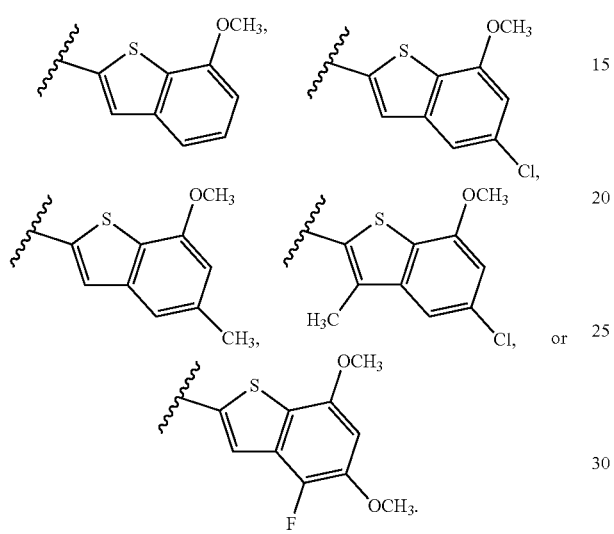

9. The compound according to claim 1, or a pharmaceutically acceptable salt or stereoisomer thereof, wherein $R_4$ is H, halogen, CN, $C_{1-3}$ alkyl, $NH_2$, $NHC_{1-3}$ alkyl, $N(C_{1-3}$ alkyl$)_2$, OH, or $OC_{1-3}$ alkyl, wherein the $C_{1-3}$ alkyl, $NHC_{1-3}$ alkyl, $N(C_{1-3}$ alkyl$)_2$, or $OC_{1-3}$ alkyl is optionally substituted with 1, 2, or 3 independently selected R substituents.

10. The compound according to claim 9, or a pharmaceutically acceptable salt or stereoisomer thereof, wherein $R_4$ is H, F, Cl, Br, I, CN, $CH_3$, $CF_3$, $CH_2OCH_3$, $NH_2$, $N(CH_3)_2$, or OH.

11. The compound according to claim 1, or a pharmaceutically acceptable salt or stereoisomer thereof, wherein L is a single bond, —CH=CH—, —CH=CHCH$_2$—, —C≡C—, or —C≡CCH$_2$—.

12. The compound according to claim 1, or a pharmaceutically acceptable salt or stereoisomer thereof, wherein $R_5$ is H, $C_{1-3}$ alkyl, $NHC_{1-3}$ alkyl, $N(C_{1-3}$ alkyl$)_2$, or morpholinyl, wherein the $C_{1-3}$ alkyl, $NHC_{1-3}$ alkyl, $N(C_{1-3}$ alkyl$)_2$, or morpholinyl is optionally substituted with 1, 2, or 3 independently selected R substituents.

13. The compound according to claim 12, or a pharmaceutically acceptable salt or stereoisomer thereof, wherein $R_5$ is H, $CH_3$, $CH_2CH_3$, $CH_2CN$, $CH_2N(CH_3)_2$, $N(CH_3)_2$, or morpholin-4-yl.

14. The compound according to claim 11, or a pharmaceutically acceptable salt or stereoisomer thereof, wherein $LR_5$ is $CH_2CN$, CH=CH$_2$, CH=CHCH$_2$N(CH$_3$)$_2$, CH=CHCH$_2$-morpholin-4-yl, or C≡CCH$_3$.

15. The compound according to claim 13, or a pharmaceutically acceptable salt or stereoisomer thereof, wherein $LR_5$ is $CH_2CN$, CH=CH$_2$, CH=CHCH$_2$N(CH$_3$)$_2$, CH=CHCH$_2$-morpholin-4-yl, or C≡CCH$_3$.

16. The compound according to claim 1, or a pharmaceutically acceptable salt or stereoisomer thereof, wherein $R_6$ is H, F, Cl, Br, I, $CH_3$, $NH_2$, or OH.

17. The compound according to claim 1, or a stereoisomer thereof, wherein the compound, or stereoisomer thereof, is selected from the group consisting of:

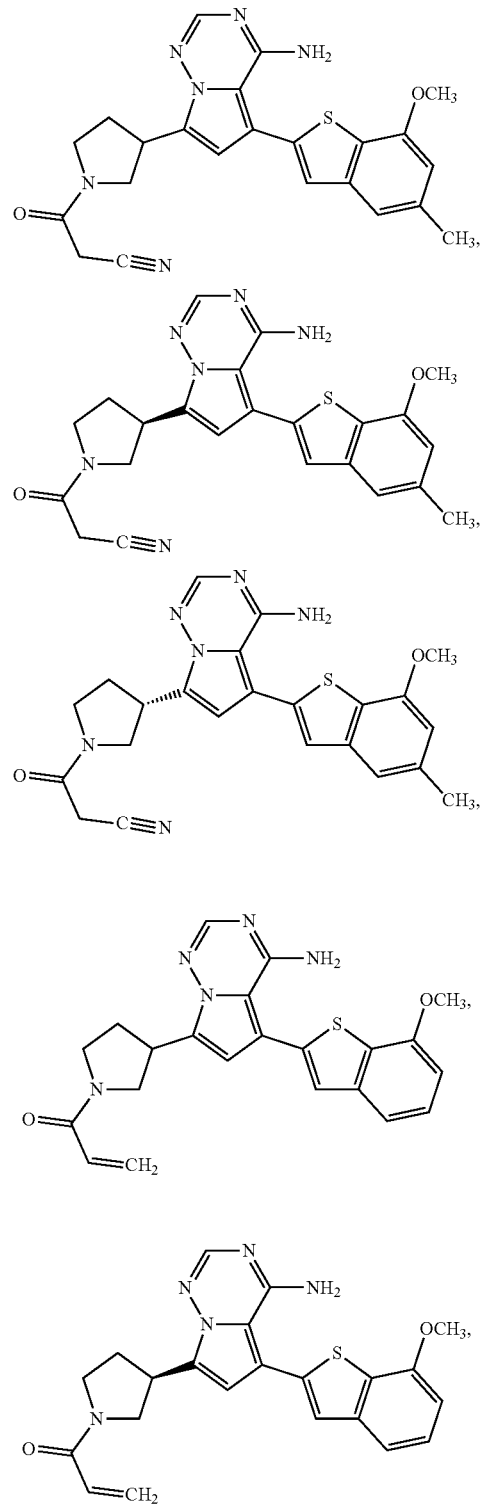

-continued
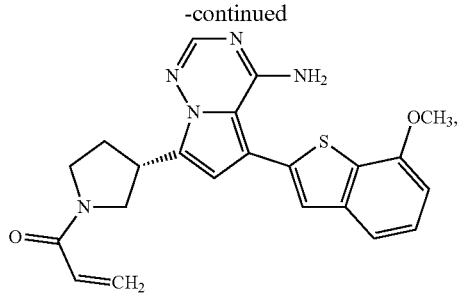
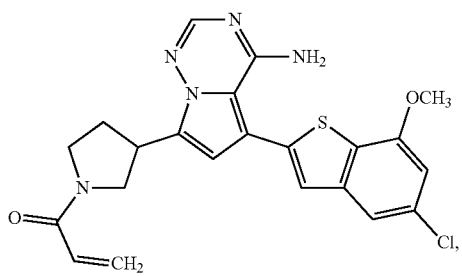
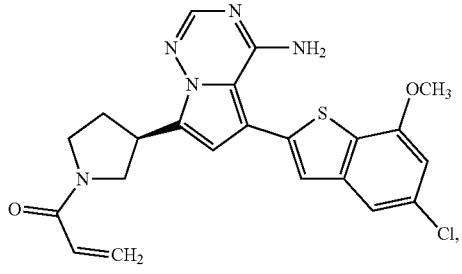
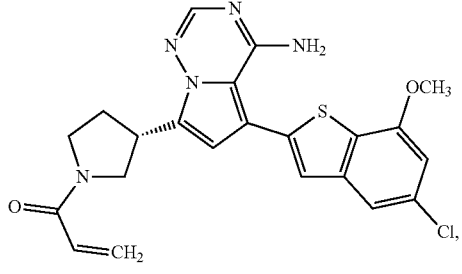
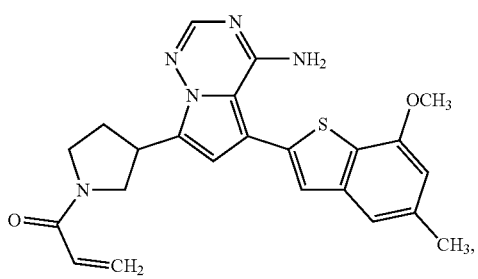
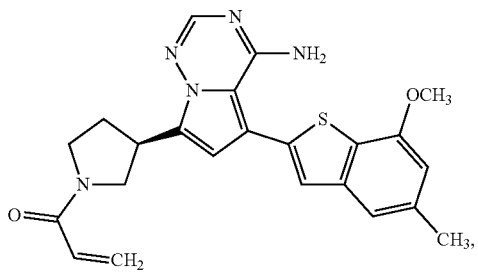
-continued
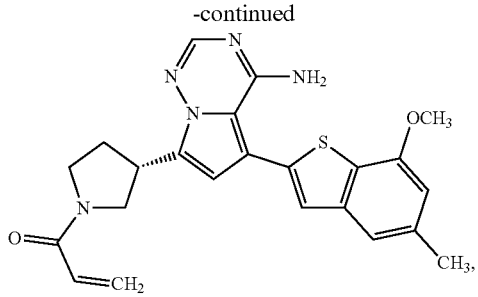
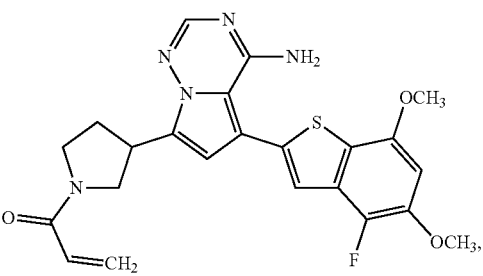
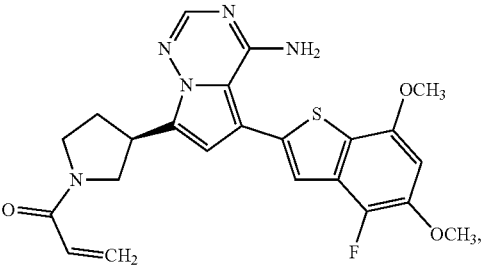
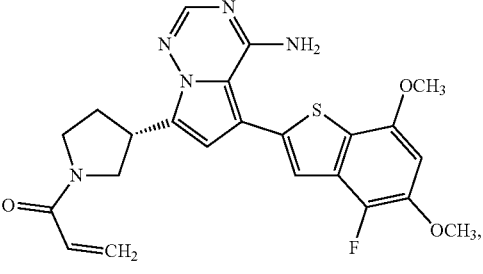
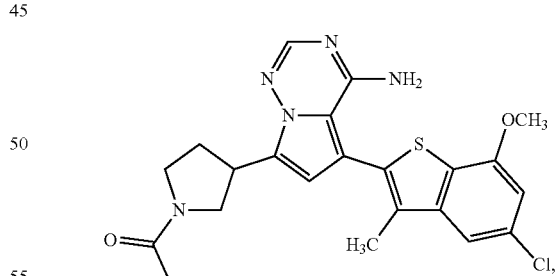
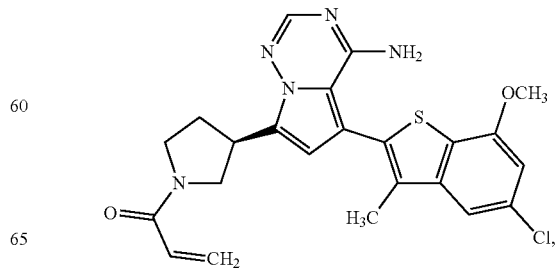

81
-continued
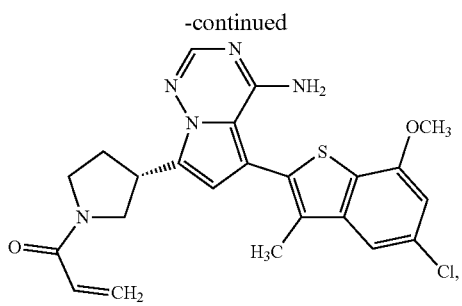
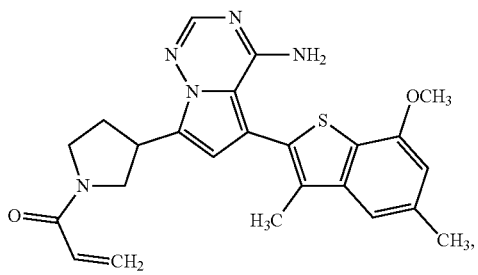
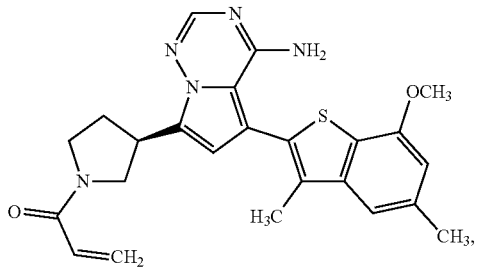
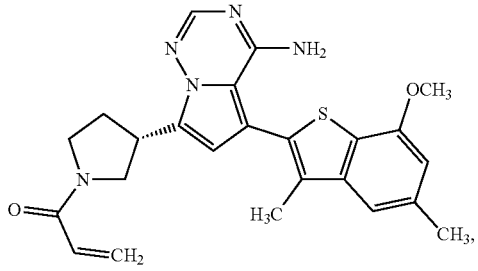
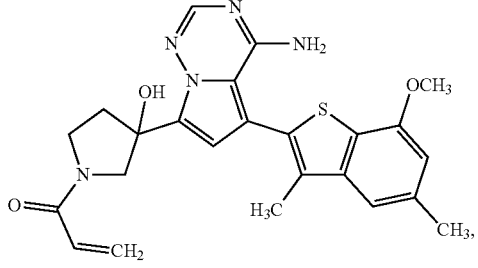
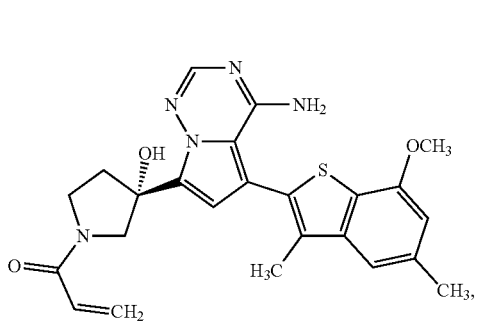
82
-continued
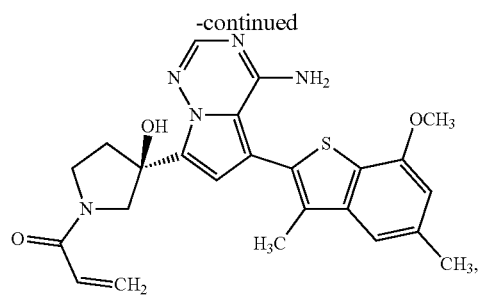
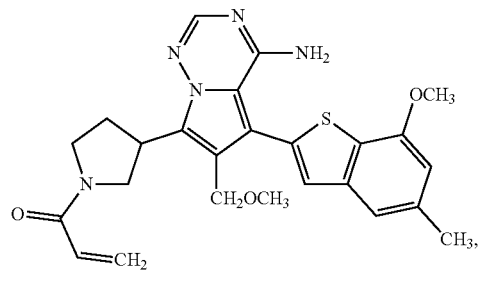
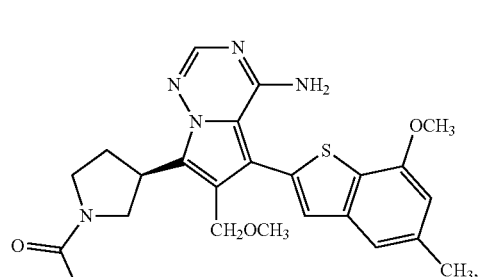
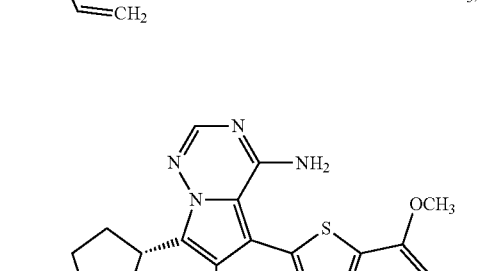
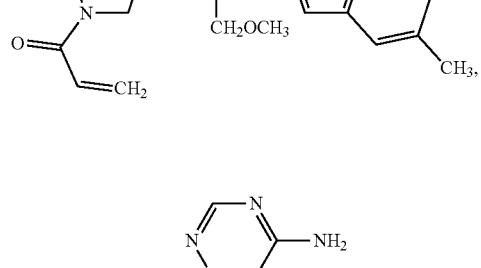
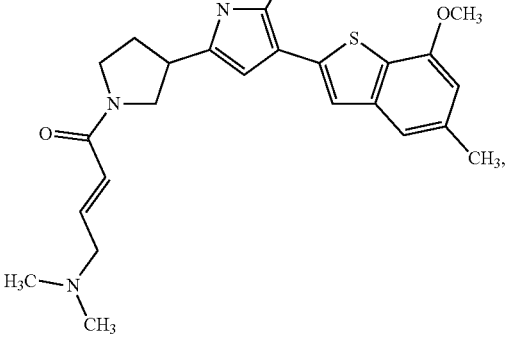

83
-continued
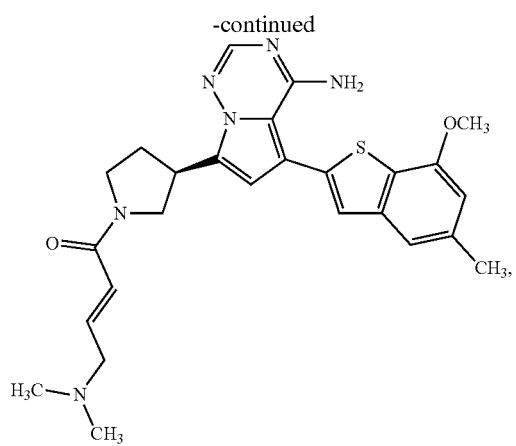
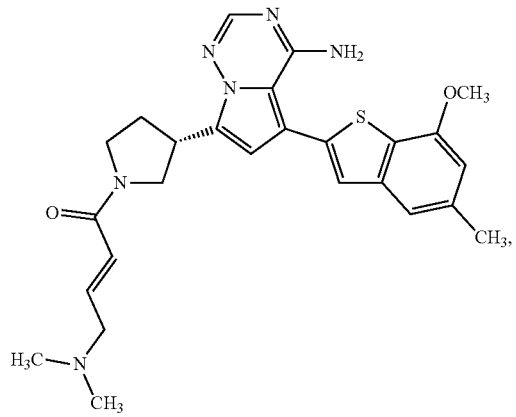
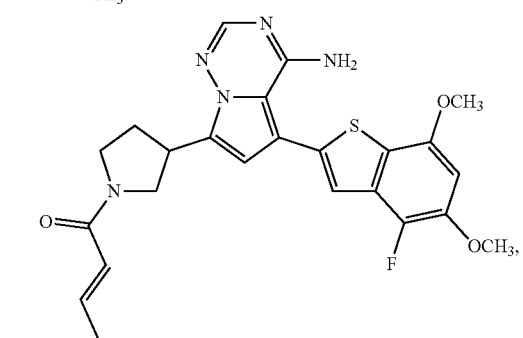
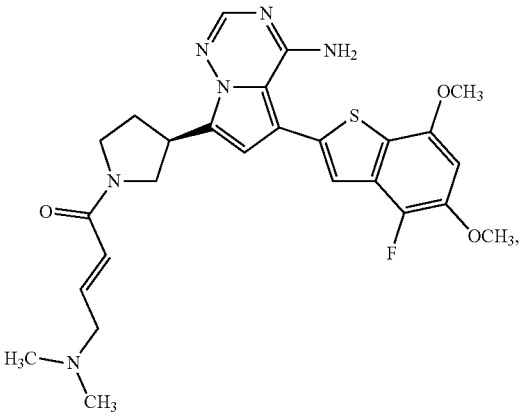
84
-continued
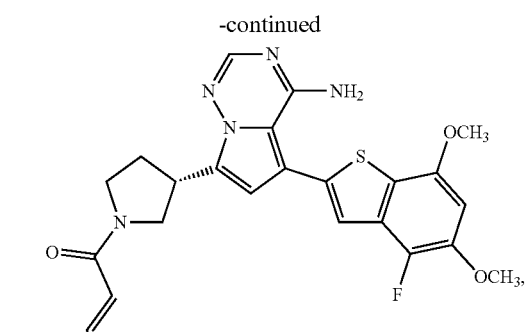
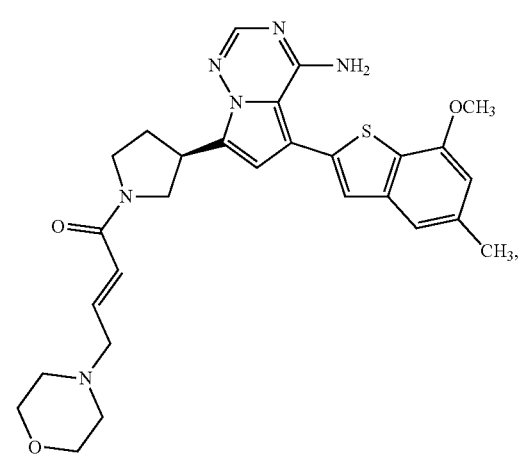

-continued
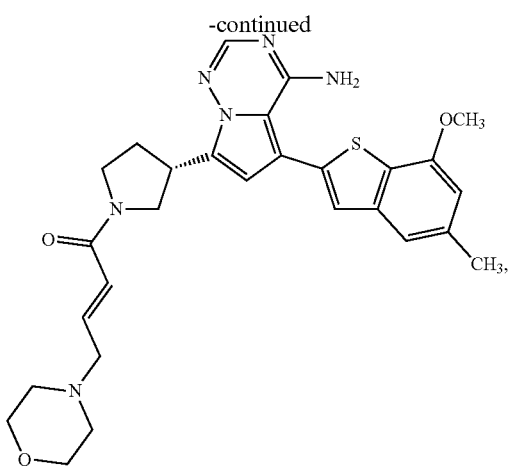
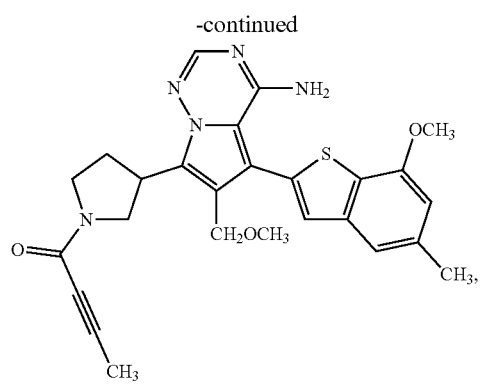
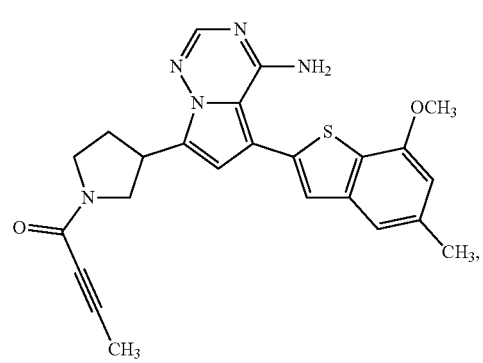
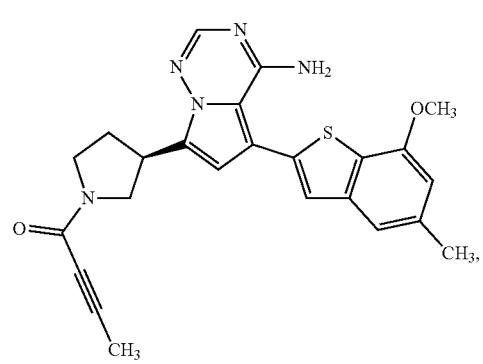
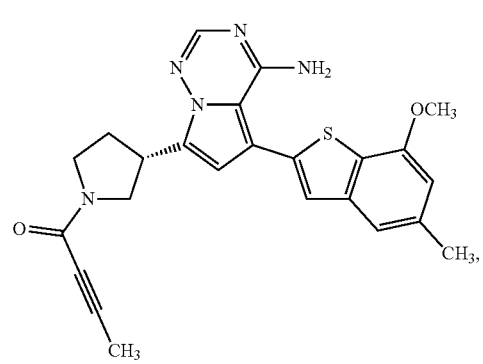
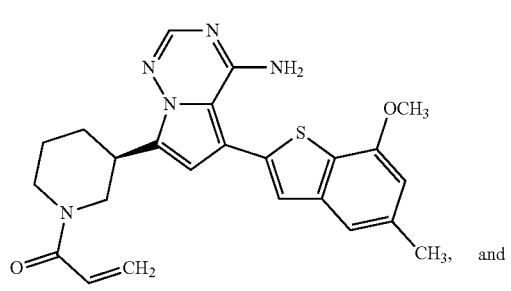
and -continued

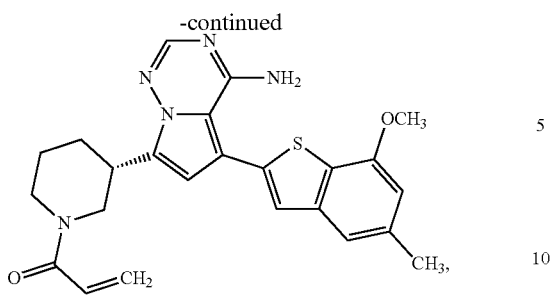

or a pharmaceutically acceptable salt thereof.

18. A pharmaceutical composition comprising a pharmaceutically acceptable carrier and the compound according to claim 1, or a pharmaceutically acceptable salt or stereoisomer thereof.

19. A method for inhibiting fibroblast growth factor receptor activity in a subject, wherein the method comprises administering to the subject in need thereof a therapeutically effective amount of the compound according to claim 1, or a pharmaceutically acceptable salt or stereoisomer thereof.

20. The method according to claim 19, wherein the subject has a solid tumor.

* * * * *

UNITED STATES PATENT AND TRADEMARK OFFICE
CERTIFICATE OF CORRECTION

PATENT NO. : 11,236,094 B2
APPLICATION NO. : 16/639442
DATED : February 1, 2022
INVENTOR(S) : Yikai Wang et al.

It is certified that error appears in the above-identified patent and that said Letters Patent is hereby corrected as shown below:

On the Title Page

Item (73) should read:
(73) CSPC ZHONGQI PHARMACEUTICAL TECHNOLOGY (SHIJIAZHUANG) CO., LTD.

Signed and Sealed this
Fourteenth Day of March, 2023

Katherine Kelly Vidal
*Director of the United States Patent and Trademark Office*